US009206426B2

(12) United States Patent
Manley et al.

(10) Patent No.: US 9,206,426 B2
(45) Date of Patent: Dec. 8, 2015

(54) INHIBITORY RNAS TO RNA BINDING PROTEINS HNRNPA1, HNRNPA2 AND PTB AND USES THEREOF

(75) Inventors: James L. Manley, Greenlawn, NY (US); Mo Chen, New York, NY (US); Charles David, New York, NY (US); Jian Zhang, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 71 days.

(21) Appl. No.: 13/582,921

(22) PCT Filed: Mar. 7, 2011

(86) PCT No.: PCT/US2011/027430
§ 371 (c)(1),
(2), (4) Date: Apr. 18, 2013

(87) PCT Pub. No.: WO2011/109823
PCT Pub. Date: Sep. 9, 2011

(65) Prior Publication Data
US 2013/0203835 A1 Aug. 8, 2013

Related U.S. Application Data

(60) Provisional application No. 61/311,038, filed on Mar. 5, 2010.

(51) Int. Cl.
*A61K 31/70* (2006.01)
*C07H 21/02* (2006.01)
*C07H 21/04* (2006.01)
*C12N 15/113* (2010.01)
*A61K 31/7105* (2006.01)
*A61K 31/713* (2006.01)
*C12Q 1/68* (2006.01)

(52) U.S. Cl.
CPC .......... *C12N 15/1137* (2013.01); *A61K 31/713* (2013.01); *A61K 31/7105* (2013.01); *C12N 15/113* (2013.01); *C12N 2310/14* (2013.01); *C12N 2310/531* (2013.01); *C12N 2320/31* (2013.01)

(58) Field of Classification Search
None
See application file for complete search history.

(56) References Cited

U.S. PATENT DOCUMENTS

| 5,994,062 | A | 11/1999 | Mulshine et al. |
| 6,165,789 | A | 12/2000 | Monia et al. |
| 6,358,683 | B1 | 3/2002 | Collins |
| 7,704,953 | B2 | 4/2010 | Herman et al. |
| 2004/0152648 | A1 | 8/2004 | Ullrich et al. |
| 2005/0153918 | A1 | 7/2005 | Chabot et al. |
| 2007/0248659 | A1 | 10/2007 | Shanahan et al. |
| 2008/0044833 | A1 | 2/2008 | Connors |
| 2009/0203055 | A1 | 8/2009 | Ngantung et al. |
| 2009/0325200 | A1 | 12/2009 | Beck et al. |

FOREIGN PATENT DOCUMENTS

WO  WO-2008/033285 A2  3/2008

OTHER PUBLICATIONS

David et al. Nature vol. 463:364-369, 2010.*
Akhtar, S. et al., "Nonviral delivery of synthetic siRNAs in vivo," The Journal of Clinical Investigation, vol. 117, No. 12, pp. 3623-3632 (Dec. 2007).
Akinc, A. et al., "Development of Lipidoid-siRNA Formulations for Systemic Delivery to the Liver," Molecular Therapy, vol. 17, No. 5, pp. 872-879 (May 2009).
Assanah, M. et al., "Glial Progenitors in Adult White Matter Are Driven to Form Malignant Gliomas by Platelet-Derived Growth Factor-Expressing Retroviruses," The Journal of Neuroscience, vol. 26, No. 25, pp. 6781-6790 (Jun. 21, 2006).
Beadle, C. et al., "The Role of Myosin II in Glioma Invasion of the Brain," Molecular Biology of the Cell, vol. 19, pp. 3357-3368 (Aug. 2008).
Biamonti, G. et al., "Human hnRNP Protein A1 Gene Expression: Structural and Functional Characterization of the Promoter," J. Mol. Biol., vol. 230, pp. 77-89 (1993).
Birney, E. et al., "Identification and analysis of functional elements in 1% of the human genome by the ENCODE pilot project," Nature, vol. 447, pp. 799-816 (Jun. 14, 2007).
Boutz, P. L. et al., "MicroRNAs regulate the expression of the alternative splicing facter nPTB during muscle development," Genes & Development, vol. 21, pp. 71-84 (2007).
Burd, C. G. et al., "RNA binding specificity of hnRNP A1: significance of hnRNP A1 high-affinity binding sites in pre-mRNA splicing," The EMBO Journal, vol. 13, No. 5, pp. 1197-1204 (1994).
Caplen, N. J. et al., "Specific inhibition of gene expression by small double-stranded RNAs in invertebrate and vertebrate systems," PNAS, vol. 98, No. 17, pp. 9742-9747 (Aug. 14, 2001).
Carpenter, B. et al., "Heterogeneous nuclear ribonucleoprotein K is over expressed, aberrantly localised and is associated with poor prognosis in colorectal cancer," British Journal of Cancer, vol. 95, pp. 921-927 (2006).
Castle, J.C. et al., "Differential expression of 24,426 human alternative splicing events and predicted cis regulation in 48 tissues and cell lines," Nat Genet., vol. 40, No. 12, pp. 1416-1425, 23 pages (Dec. 2008).
Chalk, A. M. et al., "siRNA specificity searching incorporating mismatch tolerance data," Bioinformatics, vol. 24, No. 10, pp. 1316-1317 (2008).
Chen, X. et al., "Integration of External Signaling Pathways with the Core Transcriptional Network in Embryonic Stem Cells," Cell, vol. 133, pp. 1106-1117 (Jun. 13, 2008).
Christofk, H.R. et al., "The M2 splice isoform of pyruvate kinase is important for cancer metabolism and tumor growth," Nature, vol. 452, pp. 230-233 (Mar. 13, 2008).

(Continued)

Primary Examiner — Sean McGarry
(74) Attorney, Agent, or Firm — Wilmer Cutler Pickering Hale and Dorr LLP

(57) ABSTRACT

Provided herein are methods to reduce or slow down cell growth, for example in a cancer cell comprising contacting a cell with an effective amount of a combination of inhibitory RNA molecules targeting hnRNPA1, hnRNPA2 and PTB. Provided are methods to identify agents which reduce the levels of hnRNPA1, hnRNPA2 or PTB. Provided are methods to identify agents which increase ratio of PKM1/PKM2 proteins, or reduce PKM2 levels, or increase PKM1 levels.

15 Claims, 79 Drawing Sheets

(56) References Cited

OTHER PUBLICATIONS

Christofk, H.R., et al., "Pyruvate kinase M2 is a phosphotyrosine-binding protein," Nature, vol. 452, pp. 181-186, 8 pages (Mar. 13, 2008).

Clower, C.V. et al., "The alternative splicing repressors hnRNP A1/A2 and PTB influence pyruvate kinase isoform expression and cell metabolism," PNAS, vol. 107, No. 5, pp. 1894-1899 (Feb. 2, 2010).

Dallas A, et al., "RNAi: A novel antisense technology and its therapeutic potential," Med Sci Monit., vol. 12, No. 4, pp. RA67-RA74 (2006).

Del Gatto-Konczak, F., et al., "hnRNP A1 Recruited to an Exon In Vivo Can Function as an Exon Splicing Silencer," Molecular and Cellular Biology, vol. 19, No. 1, pp. 251-260 (Jan. 1999).

Eilers, M. et al., "Myc's broad reach," Genes & Development, vol. 22, pp. 2755-2766 (2008).

Elbashir, S. M. et al., "Functional anatomy of siRNAs for mediating efficient RNAi in Drosophila melanogaster embryo lysate," The EMBO Journal, vol. 20, No. 23, pp. 6877-6888 (2001).

European Search Results issued by the European Patent Office for Application No. 11751510.6 dated Aug. 21, 2014 (7 pages).

Evans, J. R. et al., "Members of the poly (rC) binding protein family stimulate the activity of the c-myhzc internal ribosome entry segment in vitro and in vivo," Oncogene, vol. 22, pp. 8012-8020 (2003).

Fantin, V. R. et al., "Attenuation of LDH-A expression uncovers a link between glycolysis, mitochondrial physiology, and tumor maintenance," Cancer Cell, vol. 9, pp. 425-434 (Jun. 2006).

Fulham, M. J. et al., "Neuroimaging of Juvenile Pilocytic Astrocytomas: An Enigma," Radiology, vol. 189, pp. 221-225 (1993).

Furnari, F.B. et al., "Malignant astrocytic glioma: genetics, biology, and paths to treatment," Genes & Development, vol. 21, pp. 2683-2710 (2007).

Giacinti, C. et al., "RB and cell cycle progression," Oncogene, vol. 25, pp. 5220-5227 (2006).

Gribskov, M. et al., "Sequence Analysis Primer," Stockton Press, 7 pages (1991).

Hanamura, A. et al., "Regulated tissue-specific expression of antagonistic pre-mRNA splicing factors," RNA, vol. 4, pp. 430-44 (1998).

Harada, Y. et al., "Temporally Distinctive Changes of Alternative Splicing Patterns during Myogenic Differentiation of C2C12 Cells," J. Biochem., vol. 118, pp. 780-790 (1995).

He, X. et al., "Knockdown of Polypyrimidine-Tract Binding Protein (PTB) Suppresses Ovarian Tumor Cell Growth and Invasiveness In Vitro," Oncogene, vol. 26, No. 34, pp. 4961-4968, 15 pages (Jul. 26, 2007).

He Y., et al., "Roles of heterogeneous nuclear ribonucleoproteins A and B in cell proliferation," Journal of Cell Science, vol. 118, No. 14, pp. 3173-3183 (Apr. 20, 2005).

Holcik, M. et al., "Four highly stable eukaryotic mRNAs assemble 3' untranslated region RNA-protein complexes sharing cis and trans components," Proc. Natl. Acad. Sci. USA, vol. 94, pp. 2410-2414 (Mar. 1997).

Huricha, B. et al., "Delivery of Therapeutic RNAi by Nanovehicles," Chembiochem., vol. 10, Issue 15, pp. 2449-2454, 11 pages (Oct. 12, 2009).

Jin, W. et al., "Fibroblast Growth Factor Receptor-1 ∞-Exon Exclusion and Polypyrimidine Tract-binding Protein in Glioblastoma Multiforme Tumors," Cancer Research, vol. 60, pp. 1221-1224 (2000).

Jumaa, H. et al., "Regulated Expression and RNA Processing of Transcripts from the Srp20 Splicing Factor Gene during the Cell Cycle," Molecular and Cellular Biology, vol. 17, No. 6, pp. 3116-3124 (Jun. 1997).

Karni, R. et al., "The gene encoding the splicing factor SF2/ASF is a proto-oncogene," Nature Structural & Molecular Biology, vol. 14, No. 3, pp. 185-193 (Mar. 2007).

Kashima, T. et al., "hnRNP A1 functions with specificity in repression of SMN2 exon 7 splicing," Human Molecular Genetics, vol. 16, No. 24, pp. 3149-3159 (Sep. 19, 2007).

Keller, Michael, "Nanomedicinal delivery approaches for therapeutic siRNA," International Journal of Pharmaceutics, vol. 379, No. 2, pp. 210-211 (2009).

Kidder, B.L. et al., Embryonic Stem Cells Contribute to Mouse Chimeras in the Absence of Detectable Cell Fusion, Cloning and Stem Cells, vol. 10, No. 2, pp. 231-248 (2008).

Kim, J.W. et al., "Evaluation of myc E-box phylogenetic footprints in glycolytic genes by chromatin immunoprecipitation assays," Molecular and Cellular Biology, vol. 24, No. 13, pp. 5923-5936 (Jul. 2004).

Kortylewski, M. et al., "TLR agonist-Stat3 siRNA conjugates: cell-specific gene silencing and enhanced antitumor immune responses," Nature Biotechnology, vol. 27, No. 10, pp. 925-932 (Oct. 2009).

Krainer, A.R. et al., "Normal and Mutant Human β-Globin Pre-mRNAs Are Faithfully and Efficiently Spliced In Vitro," Cell, vol. 36, pp. 993-1005 (Apr. 1984).

Krummel, D.A. et al., "Crystal structure of human spliceosomal U1 snRNP at 5.5 a resolution," Nature, vol. 458, pp. 475-480, 13 pages (Mar. 26, 2009).

Liu, G. et al., "Development of new RNAi therapeutics," Histol Histophathol, vol. 22, pp. 211-217 (2007).

Lu, P. Y. et al., "Delivering Small Interfering RNA for Novel Therapeutics," Methods in Molecular Biology, vol. 437: Drug Delivery Systems, pp. 93-107 (2008).

Lu, P. Y. et al., "In Vivo Application of RNA Interference: From Functional Genomics to Therapeutics," Advances in Genetics, vol. 54, pp. 117-142, 27 pages (2005).

López-Fraga, M. et al., "RNA Interference Technologies and Therapeutics: From Basic Research to Products," Biodrugs, vol. 23, No. 5, pp. 305-332 (2009).

Marinescu, V. et al., "Regulation of Retention of FosB Intron 4 by PTB," PLoS One, Issue 9, No. e828, 10 pages (Sep. 2007).

Marjanovic, S. et al., "Expression of a new set of glycolytic isozymes in activated human peripheral lymphocytes," Biochimica et Biophysica Acta, vol. 1087, pp. 1-6 (1990).

Martinez-Contreras, R. et al., "Intronic Binding Sites for hnRNP A/B and hnRNP F/H Proteins Stimulate Pre-mRNA Splicing," PLoS Biology, vol. 4, Issue 2, e21, 0172-0185 (Feb. 2006).

Mathupala, Saroj P., "Delivery of small-interfering RNA (siRNA) to the brain," Expert Opinion on Therapeutic Patents, vol. 19, No. 2, pp. 137-140, 6 pages (Feb. 2009).

Mazurek, S. et al., "Pyruvate kinase type M2 and its role in tumor growth and spreading," Seminars in Cancer Biology, vol. 15, pp. 300-308 (2005).

Meade B. R. et al., "The Road to Therapeutic RNA Interference (RNAi): Tackling the 800 pound siRNA Delivery Gorilla," Discovery Medicine, vol. 8, No. 43, pp. 253-256 (Dec. 2009).

Michaud, S. et al., "A functional association between the 5' and 3' splice site is established in the earliest prespliceosome complex (E) in mammals," Genes & Development, vol. 7, pp. 1008-1020 (1993).

Moumen, A. et al., "hnRNP K: An HDM2 Target and Transcriptional Coactivator of p53 in Response to DNA Damage," Cell, vol. 123, pp. 1065-1078 (Dec. 16, 2005).

O'Connell, B.C. et al., "A Large Scale Genetic Analysis of c-Myc-regulated Gene Expression Patterns," The Journal of Biological Chemistry, vol. 278, pp. 12563-12573 (2003).

Pardridge, William M., "shRNA and siRNA Delivery to the Brain," Advanced Drug Delivery Reviews, vol. 59, Issues 2-3, pp. 141-152, 20 pages (Mar. 30, 2007).

Patry, C. et al., "Small interfering RNA-mediated reduction in heterogeneous nuclear ribonucleoparticule A1/A2 proteins induces apoptosis in human cancer cells but not in normal mortal cell lines," Cancer Research, vol. 63, No. 22, pp. 7679-7688 (Nov. 15, 2003).

Planck, S.R. et al., "Modulation of hnRNP A1 protein gene expression by epidermal growth factor in Rat-1 cells," Nucleic Acids Research, vol. 16, No. 24, pp. 11663-11673 (1988).

Sauliere, J. et al., "The Polypyrimidine Tract Binding Protein (PTB) Represses Splicing of Exon 6B from the β-Tropomyosin Pre-mRNA by Directly Interfering with the Binding of the U2AF65 Subunit," Molecular and Cellular Biology, vol. 26, No. 23, pp. 8755-8769 (Dec. 2006).

(56) References Cited

OTHER PUBLICATIONS

Schlosser, I. et al., "Dissection of transcriptional programmes in response to serum and c-Myc in a human B-cell line," Oncogene, vol. 24, pp. 520-524 (2005).

Schramm et al., "siRNA design including secondary structure target site prediction," Nature Methods, 2 pages (Jul. 21, 2005).

Shiio, Y. et al., "Quantitative proteomic analysis of Myc oncoprotein function," The EMBO Journal, vol. 21, No. 19, pp. 5088-5096 (2002).

Shim, H. et al., "c-Myc transactivation of LDH-A: Implications for tumor metabolism and growth," Proc Natl Acad Sci USA, vol. 94, pp. 6658-6663 (Jun. 1997).

Shimada, N. et al., "Modulation of M2-type pyruvate kinase activity by the cytoplasmic PML tumor suppressor protein," Genes to Cells, vol. 13, No. 3, pp. 245-254 (Mar. 2008).

Spellman, R. et al., "Crossregulation and Functional Redundancy between the Splicing Regulator PTB and Its Paralogs nPTB and ROD1," Molecular Cell, vol. 27, No. 3, pp. 420-434, 23 pages (Aug. 3, 2007).

Spellman, R. et al., "Novel modes of splicing repression by PTB," TRENDS in Biochemical Sciences, vol. 31, No. 2, pp. 73-76 (Feb. 2006).

Spellman, R. et al., "Regulation of alternative splicing by PTB and associated factors," Biochemical Society Transactions, vol. 33, Part 3, pp. 457-460 (Jun. 2005).

Takenaka, M. et al., "Alternative splicing of the pyruvate kinase M gene in a minigene system," Eur J Biochem, vol. 235, pp. 366-371 (1996).

Vander Heiden, M.G. et al., "Understanding the Warburg Effect: The Metabolic Requirements of Cell Proliferation," Science, vol. 324, No. 5930, pp. 1029-1033, 12 pages (May 22, 2009).

Wang, E. T. et al., "Alternative Isoform Regulation in Human Tissue Transcriptomes," Nature, vol. 456, No. 7221, pp. 470-476, 15 pages (Nov. 27, 2008).

Wang, T. et al., "Aerobic glycolysis during lymphocyte proliferation," Nature, vol. 261, No. 5562, pp. 702-705 (Jun. 27, 1976).

Warburg, Otto, "On the Origin of Cancer Cells," Science, vol. 123, No. 3191, pp. 309-314 (Feb. 24, 1956).

Watermann, D. O. et al., "Splicing Factor Tra2-$\beta$1 Is Specifically Induced in Breast Cancer and Regulates Alternative Splicing of the CD44 Gene," Cancer Research, vol. 66, pp. 4774-4780 (2006).

Wu, K. J. et al., "c-MYC activates protein kinase A (PKA) by direct transcriptional activation of the PKA catalytic subunit beta (PKA-C$\beta$) gene," Oncogene, vol. 21, pp. 7872-7882 (2002).

Yamada, K. et al., "Nutrient and hormonal regulation of pyruvate kinase gene expression," Biochem J, vol. 337, Part 1, pp. 1-11 (1999).

Zeller, K. I. et al., "An integrated database of genes responsive to the Myc oncogenic transcription factor: identification of direct genomic targets," Genome Biology, vol. 4, R69, 10 pages (Sep. 11, 2003).

Zerbe, L. K. et al., "Relative Amounts of Antagonistic Splicing Factors, hnRNP A1 and ASF/SF2, Change During Neoplastic Lung Growth: Implications for Pre-mRNA Processing," Molecular Carcinogenesis, vol. 41, pp. 187-196 (2004).

Zheng, H. et al., "p53 and Pten control neural and glioma stem/progenitor cell renewal and differentiation," Nature, vol. 455, Issue 7216, pp. 1129-1133 (Oct. 23, 2008).

Zhou, J. et al., "Differential expression of the early lung cancer detection marker, heterogeneous nuclear ribonucleoprotein-A2/B1 (hnRNP-A2/B1) in normal breast and neoplastic breast cancer," Breast Cancer Research and Treatment, vol. 66, pp. 217-224 (2001).

David et al., "HnRNP proteins controlled by cMyc deregulate pyruvate kinase mRNA splicing in cancer," Nature, vol. 463, pp. 364-368; Abstract, 2007.

Wilson et al., Genbank: AA702890.1, 1997 retrieved on Jun. 1, 2011, from the internet <URL:http://www.ncbi.nlm.nih.gov/nucest/AA702890>.

International Search Report and Written Opinion mailed on Jun. 15, 2011, for International Application No. PCT/US11/27430 filed Mar. 7, 2011 (9 pages).

\* cited by examiner

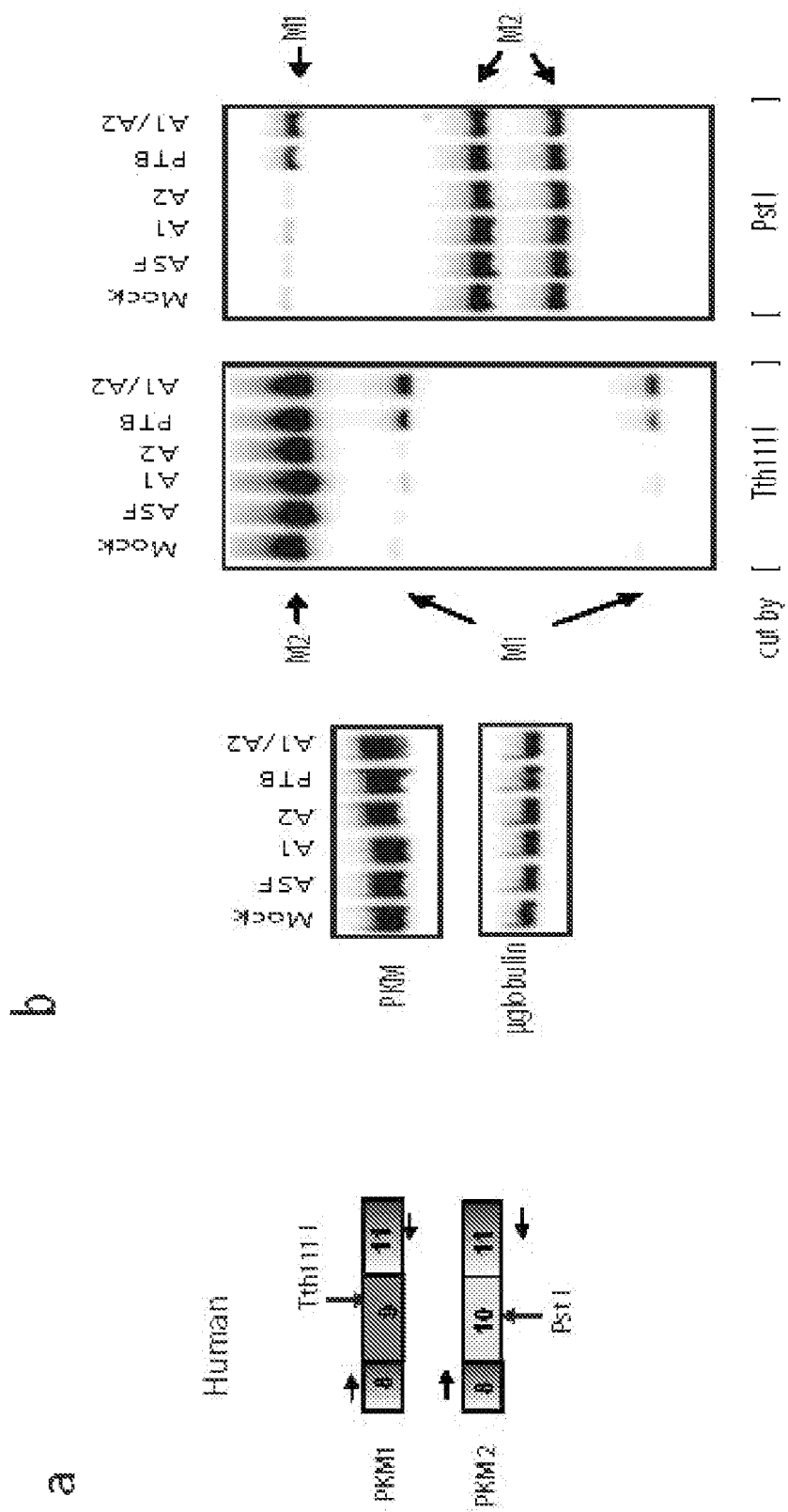
Figure 2a-b

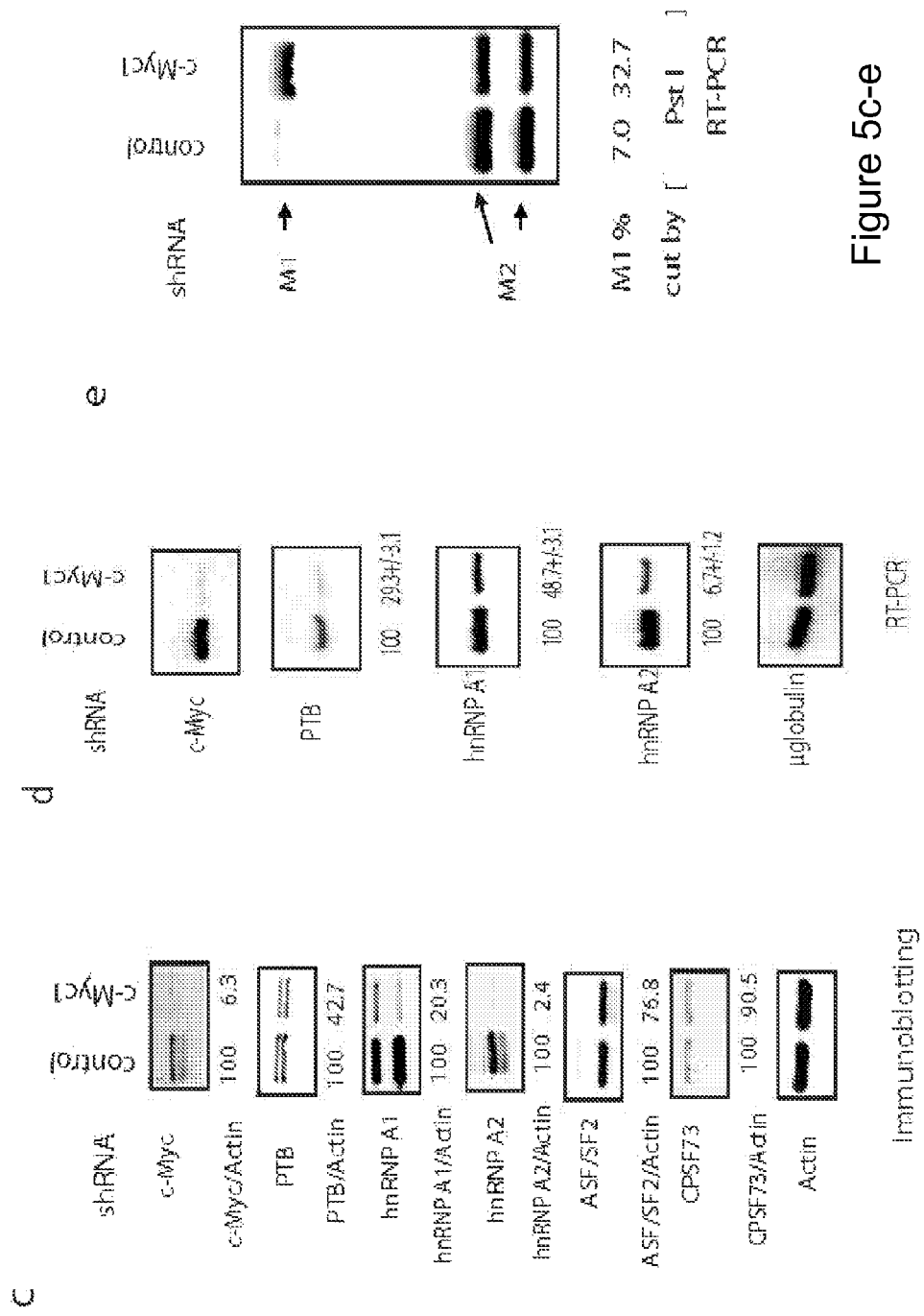

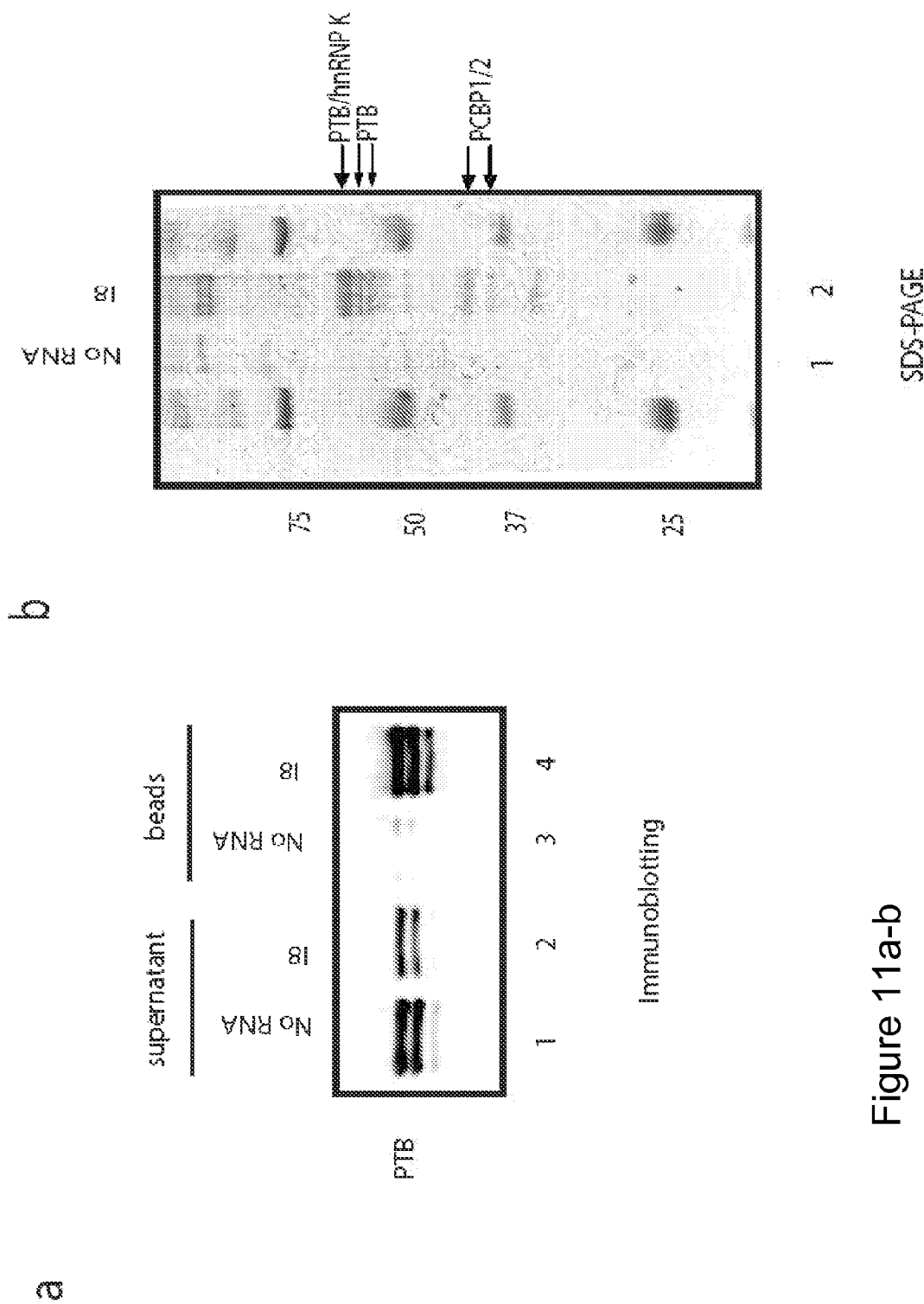
Figure 11a-b

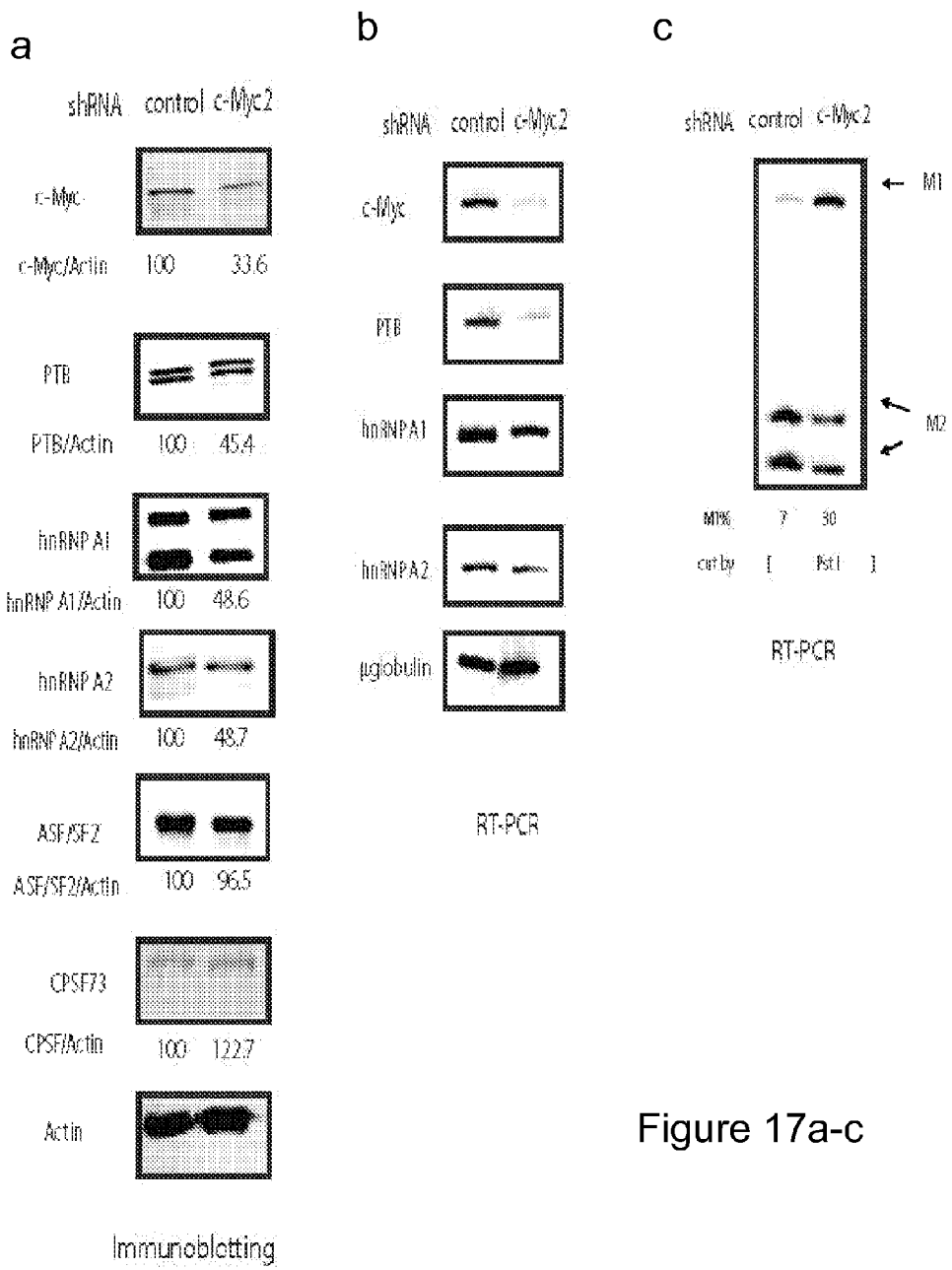
Figure 17a-c

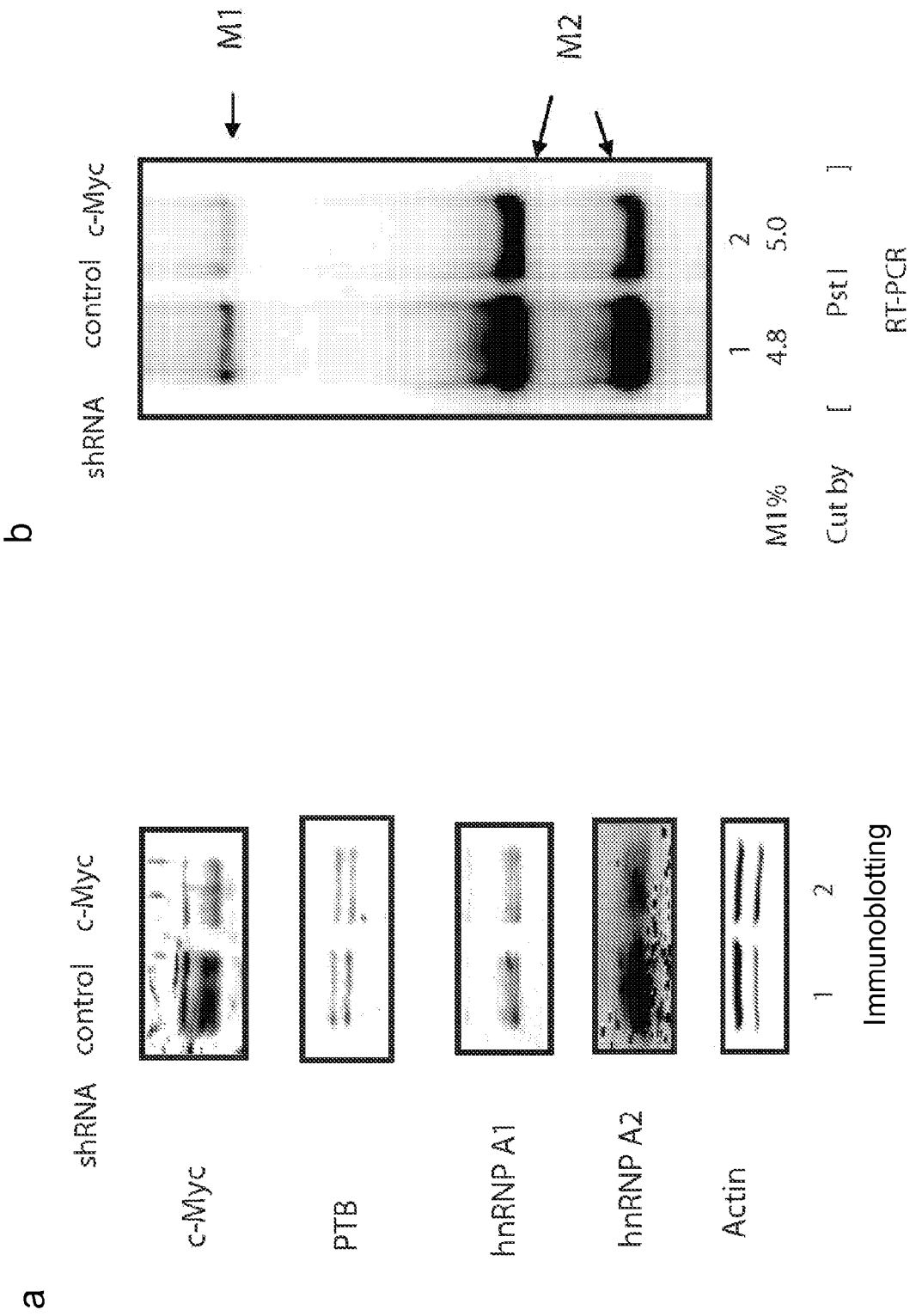
Figure 18a-b

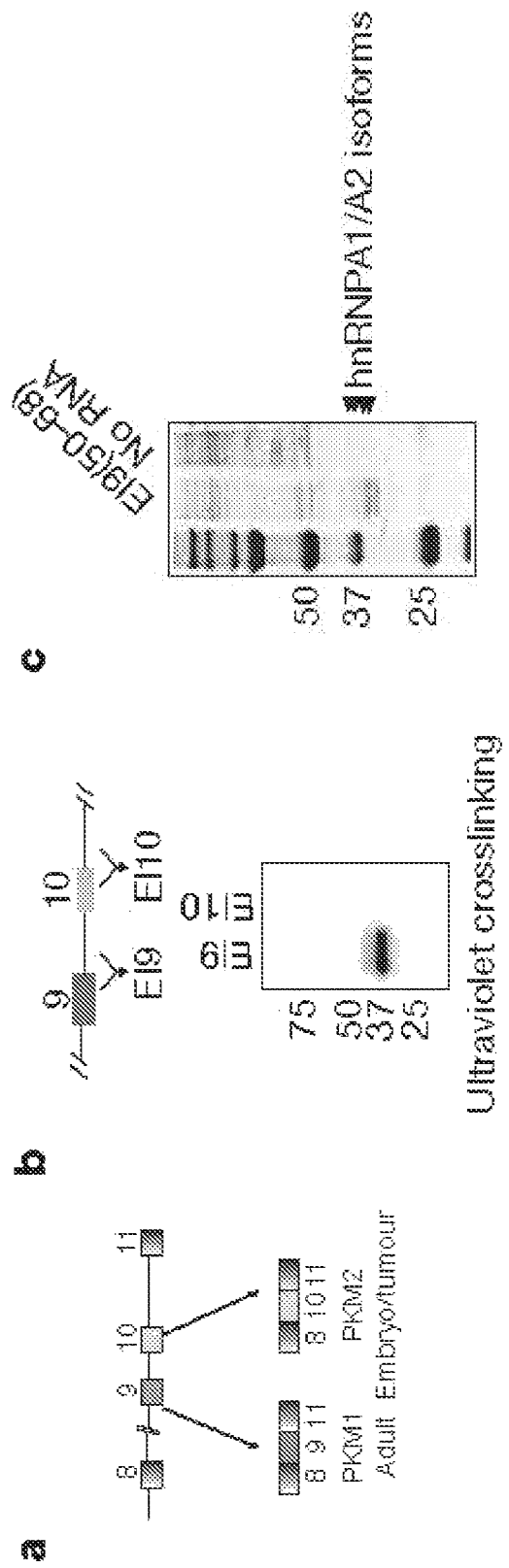
Figure 20 a-c

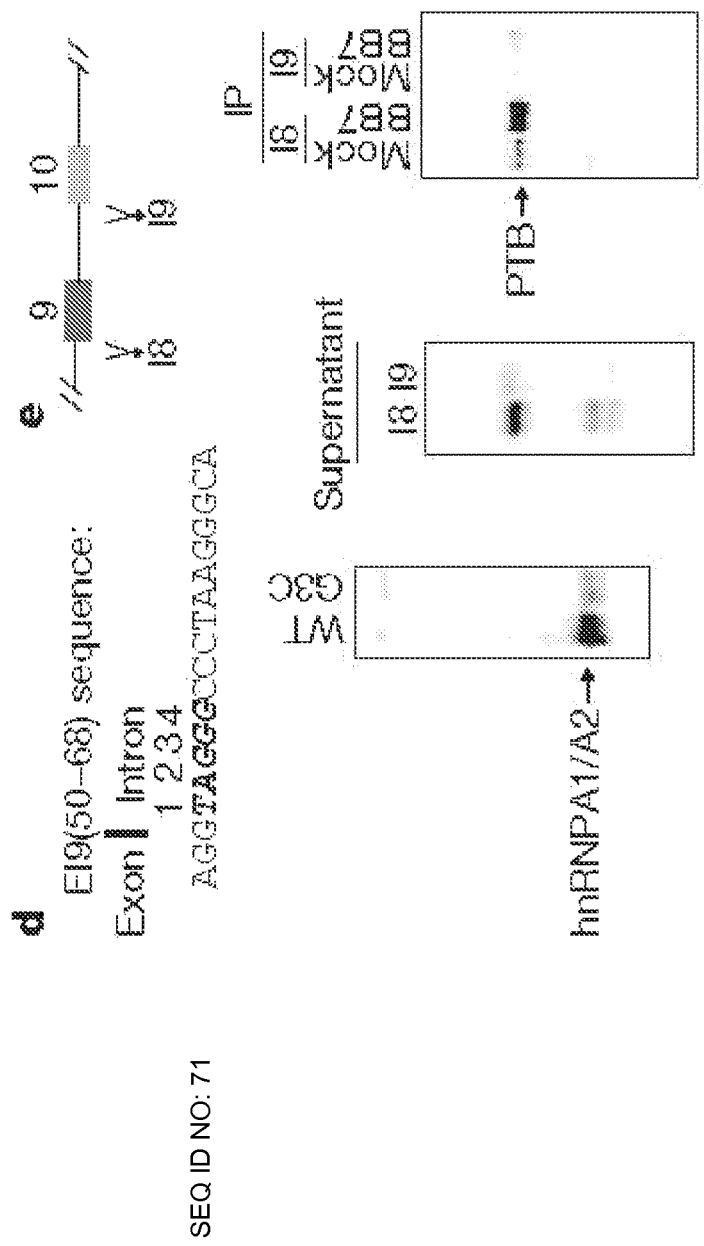
Figure 20 d-e

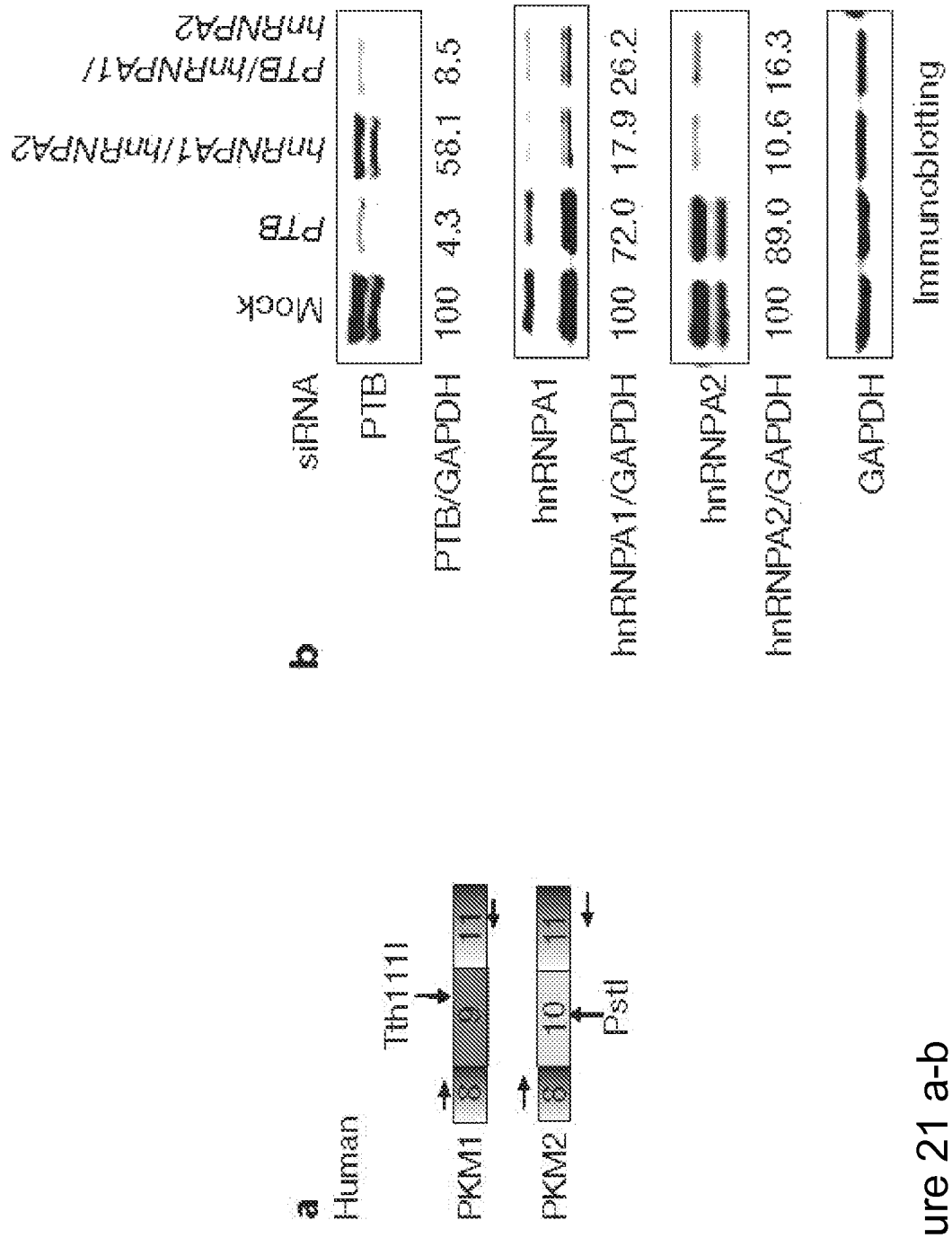
Figure 21 a-b

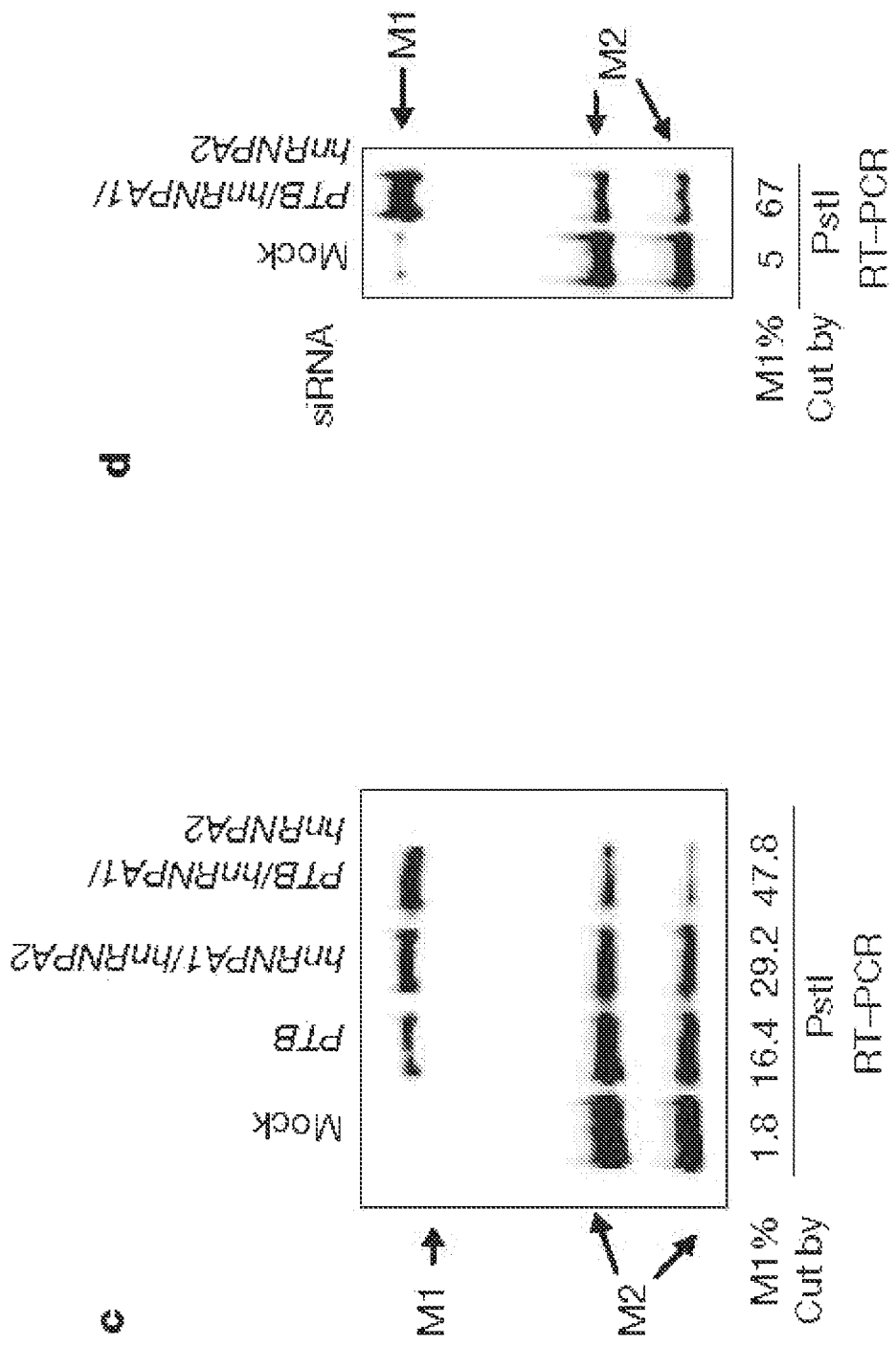
Figure 21 c-d

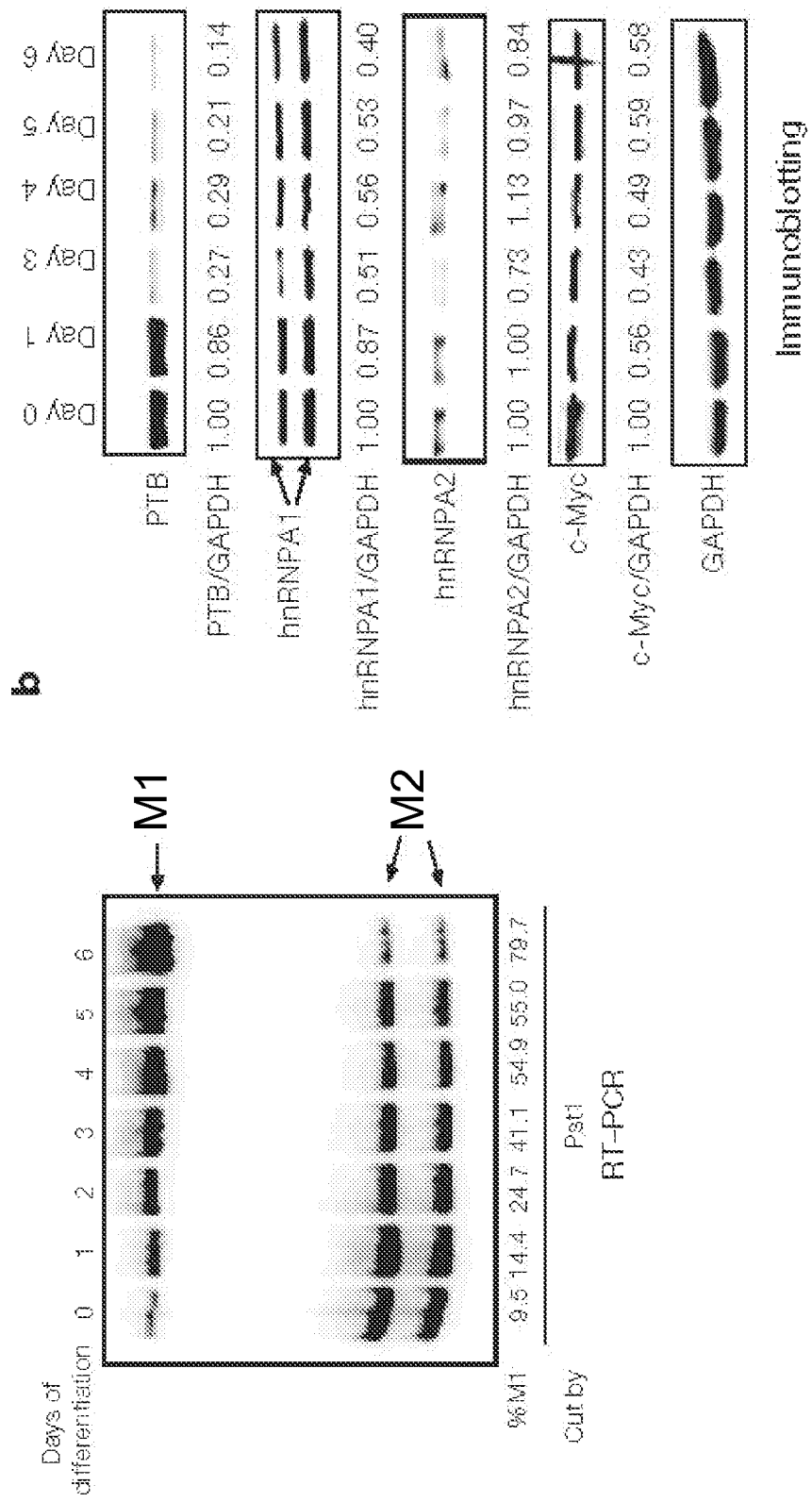
Figure 22 a-b

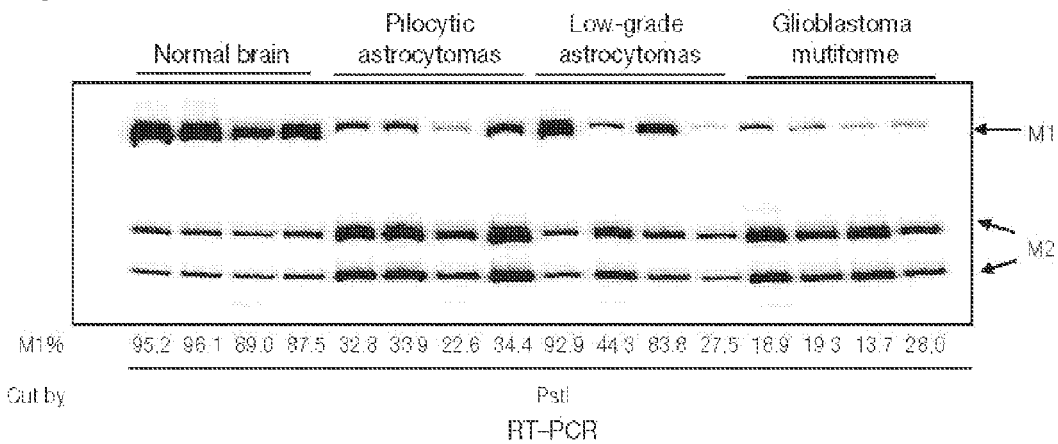
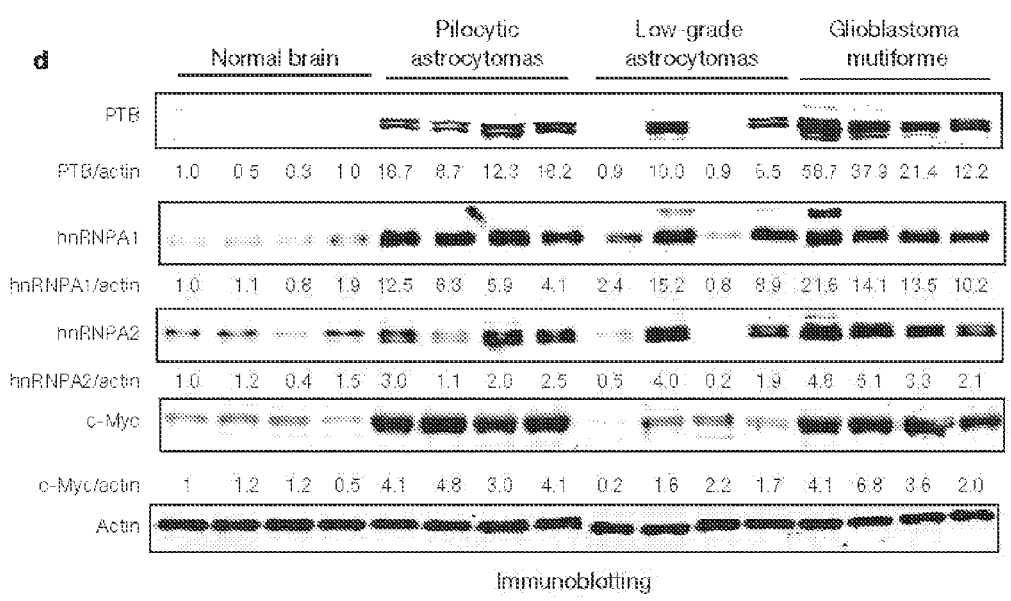
Figure 22 c-d

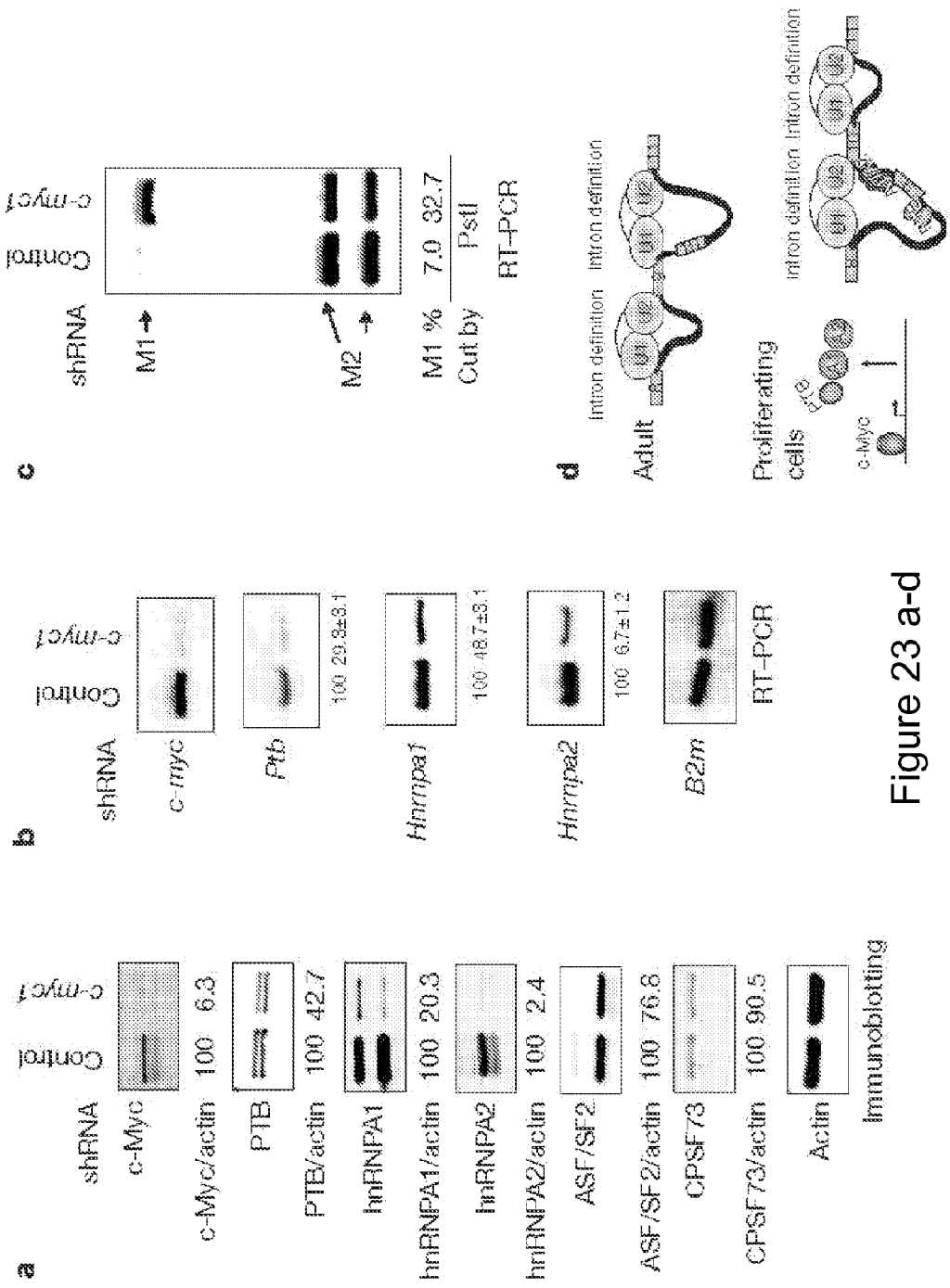
Figure 23 a-d

Figure 38A and B

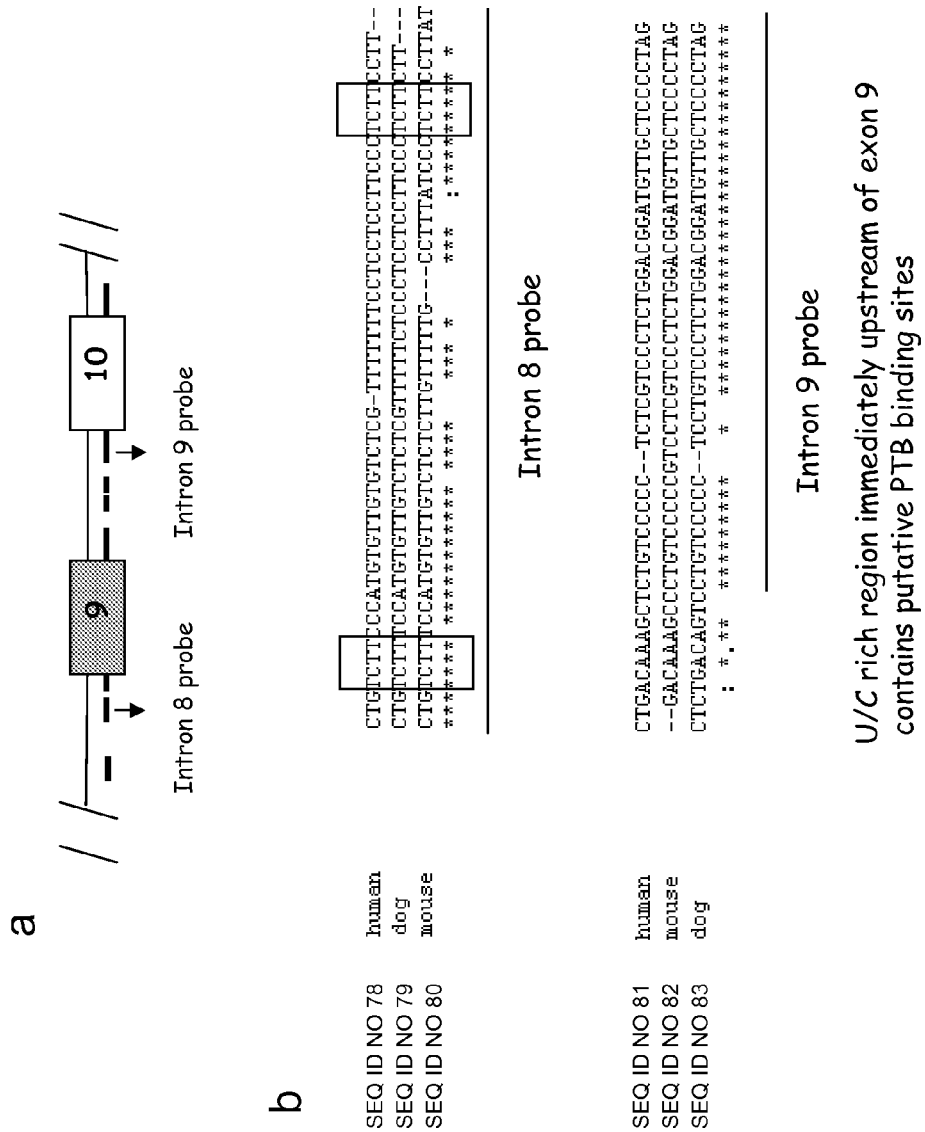
Figure 53 a-b

```
                       SEQUENCE LISTING

<160> NUMBER OF SEQ ID NOS: 90

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcggatcct tcttataagt gtttagcagc agct                              34

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggaattcac tgagccacag gacccttg                                     29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcggatccc tccttcaagt gctgcagtg                                    29

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggaatcctg ggcccaggga agggg                                        25
```

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccaagctta aattccccat tctgtcttcc catg                                   34

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggatccct gccagactcc gtcagaact                                         29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccaagcttc tgtccggtga ctcttcccc                                         29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgggatccct gccagacttg gtgaggacg                                         29

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cagcugagga agcucuuca                                                    19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaacaguuc cguaagcuc                                                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
gccucaacgu caaguacaa                                                        19

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
gatccgaggc ttcttataag tgtttactcg agtaaacact tataagaagc ctcttttta           59

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
gatcccatcc tatgttgcgg tcgctactcg agtagcgacc gcaacatagg atgttttta           59

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
gatcccggac acacaacgtc ttggaactcg agttccaaga cgttgtgtgt ccgttttta           59

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15 gatcccata atgtaaactg cctcaactcg agttgaggca gtttacatta tggttttta            59

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ctgaaggcag tgatgtggcc                                                      20

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acccggaggt ccacgtcctc                                                   20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caaggggact accctctgg                                                    19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acacgaaggt cgacatcctc                                                   20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggctatccag cgtactccaa a                                                 21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggcaggcat actcatcttt tt                                                22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttctggtgct tgtctcactg a                                                 21

<210> SEQ ID NO 23
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cagtatgttc ggcttcccat tc                                              22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tggaagcaat tttggaggtg g                                               21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggttccgtgg tttagcaaag t                                               21

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aagaaatgca ggaagtccaa agt                                             23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctcctccata accagggcta c                                               21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agcagagact acactcgacc t                                               21

<210> SEQ ID NO 29
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctcctgcat acggagagg                                                    19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggcaggttc tggtattgga t                                                 21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggctcggaaa tggtagggg                                                    19

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgcggatcct tcttataagt gtttagcagc agct                                   34

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cggaattcac tgagccacag gaccctttg                                         29

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgcggatccc tccttcaagt gctgcagtg                                         29

<210> SEQ ID NO 35
<211> LENGTH: 25
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 35
cggaatcctg ggcccaggga agggg    25

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
cccaagctta aattccccat tctgtcttcc catg    34

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
cgggatccct gccagactcc gtcagaact    29

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cccaagcttc tgtccggtga ctcttcccc    29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cgggatccct gccagacttg gtgaggacg    29

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
cagcugagga agcucuuca    19

<210> SEQ ID NO 41
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 41
ggaacaguuc cguaagcuc                                                    19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gccucaacgu caaguacaa                                                    19

<210> SEQ ID NO 43
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gatccgaggc ttcttataag tgtttactcg agtaaacact tataagaagc ctcttttta        59

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gatcccatcc tatgttgcgg tcgctactcg agtagcgacc gcaacatagg atgttttta        59

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gatcccggac acacaacgtc ttggaactcg agttccaaga cgttgtgtgt ccgttttta        59

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gatccccata atgtaaactg cctcaactcg agttgaggca gtttacatta tggttttta        59

<210> SEQ ID NO 47
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 47
ctgaaggcag tgatgtggcc                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acccggaggt ccacgtcctc                                               20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caaggggact accctctgg                                                19

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acacgaaggt cgacatcctc                                               20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggctatccag cgtactccaa a                                             21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cggcaggcat actcatcttt tt                                            22

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 53
ttctggtgct tgtctcactg a                                              21

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cagtatgttc ggcttcccat tc                                             22

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tggaagcaat tttggaggtg g                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggttccgtgg tttagcaaag t                                              21

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aagaaatgca ggaagtccaa agt                                            23

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctcctccata accagggcta c                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 59
agcagagact acactcgacc t                                             21

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gctcctgcat acggagagg                                                19

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gggcaggttc tggtattgga t                                             21

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggctcggaaa tggtagggg                                                19

<210> SEQ ID NO 63
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccaaagcctc tttattctct tctcgagaag agaataaaga ggctttggtt ttt          53

<210> SEQ ID NO 64
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gccacaactg tgaagtaaga actcgagttc ttacttcaca gttgtggctt ttt          53

<210> SEQ ID NO 65
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 65
gtcacaatgc agaagttaga actcgagttc taacttctgc attgtgactt ttt    53

<210> SEQ ID NO 66
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
caacaagatg aagagcacca actcgagttg gtgctcttca tcttgttgtt ttt    53

<210> SEQ ID NO 67
<211> LENGTH: 19
<212> TYPE: DNA
<213> ORGANISM: Homo sapiens

<400> SEQUENCE: 67
aggtagggcc ctaagggca    19

<210> SEQ ID NO 68
<211> LENGTH: 49
<212> TYPE: DNA
<213> ORGANISM: Homo sapiens

<400> SEQUENCE: 68
aaagctctgt cccctctcg tccctctgga cggatgttgc tcccctag    49

<210> SEQ ID NO 69
<211> LENGTH: 48
<212> TYPE: DNA
<213> ORGANISM: Homo sapiens

<400> SEQUENCE: 69
tcctcctcct tccctcttcc ttgcccctc ttcccctaaa ccttacag    48

<210> SEQ ID NO 70
<211> LENGTH: 48
<212> TYPE: DNA
<213> ORGANISM: Homo sapiens

<400> SEQUENCE: 70
tcctcctcct tcctgttcc ttgcccctg ttcccctaaa ccttacag    48

<210> SEQ ID NO 71
<211> LENGTH: 19
<212> TYPE: DNA
<213> ORGANISM: Homo sapiens

<400> SEQUENCE: 71
aggtagggcc ctaagggca    19

<210> SEQ ID NO 72
<211> LENGTH: 49
<212> TYPE: DNA
<213> ORGANISM: Homo sapiens

<400> SEQUENCE: 72
aaagctctgt cccctctcg tccctctgga cggatgttgc tcccctag    49

<210> SEQ ID NO 73

-continued

<210> SEQ ID NO 73
<211> LENGTH: 48
<212> TYPE: DNA
<213> ORGANISM: Homo sapiens

<400> SEQUENCE: 73
tcctcctcct tccctcttcc ttgccccctc ttcccctaaa ccttacag                48

<210> SEQ ID NO 74
<211> LENGTH: 48
<212> TYPE: DNA
<213> ORGANISM: Homo sapiens

<400> SEQUENCE: 74
tcctcctcct tccctgttcc ttgccccctg ttcccctaaa ccttacag                48

<210> SEQ ID NO 75
<211> LENGTH: 19
<212> TYPE: DNA
<213> ORGANISM: Homo sapiens

<400> SEQUENCE: 75
aggtagggcc ctaagggca                                                19

<210> SEQ ID NO 76
<211> LENGTH: 45
<212> TYPE: DNA
<213> ORGANISM: Homo sapiens

<400> SEQUENCE: 76
ctgtcttccc atgtgttgtg tctcgttttt ttcctcctcc ttccc                   45

<210> SEQ ID NO 77
<211> LENGTH: 42
<212> TYPE: DNA
<213> ORGANISM: Homo sapiens

<400> SEQUENCE: 77
ctgtccccct ctcgtccctc tggacggatg ttgctcccct ag                      42

<210> SEQ ID NO 78
<211> LENGTH: 53
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
ctgtcttccc atgtgttgtg tctcgttttt ttcctcctcc ttccctcttc ctt          53

<210> SEQ ID NO 79
<211> LENGTH: 53
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
ctgtctttcc atgtgttgtc tctcgttttt ctccctcctc cttccctctt ctt          53

<210> SEQ ID NO 80
<211> LENGTH: 53
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 80
ctgtctttcc atgtgttgtc tctcttgttt ttgcctttat ccctcttcct tat            53

<210> SEQ ID NO 81
<211> LENGTH: 53
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
ctgacaaagc tctgtccccc tctcgtccct ctggacggat gttgctcccc tag            53

<210> SEQ ID NO 82
<211> LENGTH: 53
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
gacaaagccc tgtcccccgt cctcgtccct ctggacggat gttgctcccc tag            53

<210> SEQ ID NO 83
<211> LENGTH: 53
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ctctgacagt cctgtccccc tcctgtccct ctggacggat gttgctcccc tag            53

<210> SEQ ID NO 84
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ttttgccttt atccctcttc cttatccctc ctaccctaaa ccttacag                  48

<210> SEQ ID NO 85
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
tcctcctcct tccctcttcc ttgccccctc ttccctaaa ccttacag                   48

<210> SEQ ID NO 86
<211> LENGTH: 48
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 86
agccctgtcc cccgtcctcg tccctctgga cggatgttgc tcccctag                    48

<210> SEQ ID NO 87
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
aaagctctgt cccctctcg tccctctgga cggatgttgc tcccctag                     48

<210> SEQ ID NO 88
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tcctcctcct tccctcttcc ttgcccctc ttccctaaa ccttacag                      48

<210> SEQ ID NO 89
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tcctcctcct tccctgttcc ttgcccctg ttccctaaa ccttacag                      48

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aaagctctgt cccctctcg tccctctgga cggatgttgc tcccctag                     48
```

US 9,206,426 B2

INHIBITORY RNAS TO RNA BINDING PROTEINS HNRNPA1, HNRNPA2 AND PTB AND USES THEREOF

The invention disclosed herein was made with U.S. Government support under NIH GM 48259. Accordingly, the U.S. Government has certain rights in this invention.

This application is a U.S. National Stage of International Patent Application No. PCT/US11/27430, filed Mar. 7, 2011, which claims priority to U.S. Ser. No. 61/311,038 filed Mar. 5, 2010, the contents of both applications are hereby incorporated by reference in their entireties.

All patents, patent applications and publications cited herein are hereby incorporated by reference in their entirety. The contents of all of these publications in their entireties are hereby incorporated by reference into this application in order to more fully describe the state of the art as known to those skilled therein as of the date of the invention described and claimed herein.

BACKGROUND

PKM2 and the adult isoform PKM1 are produced from the same gene Pyruvate Kinase M, and differ by a single mutually exclusive exon. Cancer cells take up glucose and convert it to lactate while avoiding oxidative phosphorylation, which is critical for maximal tumorigenicity. This is in part explained by the observation, that almost universally, tumors revert to express the embryonic PKM2.

SUMMARY

The invention provides the discovery that three proteins, PTB, hnRNPA1, hnRNPA2 bind to specific RNA sequences flanking an adult specific exon in Pyruvate Kinase M gene pre-mRNA. This binding prevents the production of adult isoform PKM1 and promotes the production of the cancer isoform PKM2. The invention also provides that siRNA knockdown of these three proteins leads to a dramatic increase in the level of PKM1 in cancer cells, as well as a cessation of growth. The invention also provides that the oncogenic transcription factor c-Myc is capable of regulating the expression of PTB, hnRNPA1, hnRNPA2 to promote expression of the cancer-associated PKM2 isoform. The invention provides methods for reverting the PKM isoform in cancer cells from PKM2 to the adult isoform PKM1, which does not support growth as well as PKM2. In certain aspects, the invention provides a method to treat cancer comprising administering to a subject in need thereof an effective amount of a combination of inhibitory RNA molecules targeting hnRNPA1, hnRNPA2 and PTB mRNAs.

In certain aspects, the invention provides a method to reduce cell growth of a cancer cell comprising contacting a cancer cell with an effective amount of a composition comprising, consisting essentially of, consisting a combination of inhibitory RNA molecules targeting hnRNPA1, hnRNPA2 and PTB, whereby cancer is treated.

In certain embodiments of the methods, the combination of inhibitory RNA molecules target hnRNPA1, hnRNPA2 and PTB so as to reduce or inhibit the expression of hnRNPA1, hnRNPA2 and PTB, wherein reducing or inhibiting the expression of hnRNPA1, hnRNPA2 and PTB is thereby reducing the levels of PKM2 and increasing the levels of PKM1, and is reducing the growth of a cell, including a cancel cell.

In certain aspects, the invention provides a method to treat cancer comprising contacting a cell with an effective amount of a combination of inhibitory RNA molecules targeting hnRNPA1, hnRNPA2 and PTB.

In certain aspects, the invention provides a method to reduce or slow down cell growth in a cell comprising contacting a cell with an effective amount of a combination of inhibitory RNA molecules targeting hnRNPA1, hnRNPA2 and PTB.

In certain aspects, the invention provides a method to reduce the levels of RNA binding proteins hnRNPA1, hnRNPA2 and PTB in a cell comprising contacting a cell with an effective amount of a combination of inhibitory RNA molecules targeting hnRNPA1, hnRNPA2 and PTB.

In certain aspects, the invention provides a method to reduce the amount of hnRNPA1, hnRNPA2 and PTB protein bound to pyruvate kinase pre-mRNA in a cell, comprising contacting a cell with an effective amount of a combination of inhibitory RNA molecules targeting hnRNPA1, hnRNPA2 and PTB.

In certain aspects, the invention provides a method to reduce levels of PKM2 RNA or protein in a cell, comprising contacting a cell with an effective amount of a combination of inhibitory RNA molecules targeting hnRNPA1, hnRNPA2 and PTB.

In certain aspects, the invention provides a method to increase levels of PKM1 RNA or protein in a cell, comprising contacting a cell with an effective amount of a combination of inhibitory RNA molecules targeting hnRNPA1, hnRNPA2 and PTB.

In certain aspects, the invention provides a method to alter the ratio of PKM2/RKM1 RNA or protein in a cell, comprising contacting a cell with an effective amount of a combination of inhibitory RNA molecules targeting hnRNPA1, hnRNPA2 and PTB. In certain aspects, the invention provides a method to reduce the ratio of PKM2/RKM1 RNA or protein in a cell, comprising contacting a cell with an effective amount of a combination of inhibitory RNA molecules targeting hnRNPA1, hnRNPA2 and PTB.

In certain embodiments, the inhibitory RNA molecule, which targets hnRNPA1, hnRNPA2 or PTB mRNAs, have sequences as described herein, or have sequences which are functional variants or equivalents of the sequences described herein. In certain embodiments, the inhibitory RNA molecule, which targets hnRNPA1, hnRNPA2 or PTB mRNAs, is a siRNA. In certain embodiments, the inhibitory RNA molecule, which targets hnRNPA1, hnRNPA2 or PTB mRNAs, is a shRNA. In certain embodiments, the shRNA is comprised in an RNAi expression vector. In certain embodiments, the inhibitory RNA is adapted for delivery to the desired tissue or cell.

In certain embodiments, the inhibitory RNA molecule against hnRNPA1 comprise, consist essentially of, consists of SEQ ID NO: 9 or 64, the inhibitory RNA molecule against hnRNPA2 comprise, consist essentially of, consists of SEQ ID NO: 10 or 65, and the inhibitory molecule against PTB comprise, consist essentially of, consists of SEQ ID NO: 11 or 63.

In certain embodiments, the cell is a cancer cell. In certain embodiments, the cell is brain tumor cell or any other cancer cell, including but not limited to cancer cells described herein. In certain embodiments, the cell is a glioma tumor cell. In certain embodiments, the cell is a breast cancer cell. In certain embodiments, the cell expresses PKM2. In certain embodiments, the expression of PKM2 is developmentally inappropriate.

In certain aspects, the invention provides a method to identify a therapeutic or an inhibitory agent which reduce the levels of hnRNPA1, hnRNPA2 or PTB mRNAs or proteins comprising contacting a cell or tissue with an agent and determining the levels of hnRNPA1, hnRNPA2 or PTB mRNAs or proteins in the presence or absence of the agent, wherein an agent which reduced the levels of hnRNPA1, hnRNPA2 or PTB mRNAs or protein is an inhibitory agent.

In certain aspects, the invention provides a method to identify a therapeutic agent which increases the ratio of PKM1/PKM2 proteins comprising contacting a cell or tissue with an agent and determining the levels of PKM1 and PKM2 proteins in the presence or absence of the agent, wherein an agent which increases the level of PKM1 or decreases the level of PKM2 protein is a therapeutic agent.

In certain embodiments, the cell or tissue is a normal cell which is not affected by disease or disorder. In certain embodiments, wherein the cell or tissue is a cell which is affected by disease or disorder as described herein. In certain embodiments, determining is carried out by any suitable method known in the art or described herein. In certain embodiments, PKM2 is overexpressed. In certain embodiments, PKM2 expression is developmentally inappropriate. In certain embodiments, hnRNPA1, hnRNPA2 or PTB are overexpressed. In certain embodiments, the cells overexpress c-Myc, hnRNPA1, hnRNPA2 or PTB.

BRIEF DESCRIPTION OF THE DRAWINGS

FIG. 5: c-Myc upregulates PTB/A1/A2 alters PKM splicing. a, c-Myc mRNA (left) and protein (right) levels in differentiating C2C12 cells determined by RT-PCR and immunoblotting. b, Immunoblotting for c-Myc using normal brain and glioma samples. Samples were loaded in the same order as in FIG. 4. Bands were quantified and normalized to actin. c, Immunoblotting using NIH-3T3 cells stably expressing control or c-Myc-targeting shRNAs. Signals were quantified and normalized to actin, d, RT-PCR using RNA from cells stably expressing control or c-Myc-targeting shRNAs. Real-time RT-PCR was performed separately to quantify the relative levels of PTB/A1/A2 mRNAs in control and c-Myc knockdown cells, using RPL13A as a reference gene. Relative levels of each are shown below each panel, with standard deviation indicated (n=3). e, PKM1/2 ratios in control and c-Myc knockdown cells determined as in FIG. 3a.

FIG. 14: SRp20 knockdown does not affect the PKM1/2 mRNA ratio. a, Immunoblotting to detect SRp20 protein levels in HeLa cells treated with either control shRNA (lane 1) or SRp20-targeting shRNA (lane 2). b, PKM1/2 ratios in control and SRp20 knockdown cells determined as in FIG. 2a.

FIG. 17: A stable cell line expressing a second c-Myc-targeting shRNA also reduced PTB/A1/A2 and PKM2 mRNA levels. a, Immunoblotting using NIH-3T3 cells stably expressing control shRNA or c-Myc-targeting shRNA2. Signals were quantitated and normalized to actin. b, RT-PCR was used to determine relative mRNA levels in cells stably expressing control shRNA r c-Myc-targeting shRNA2. c, PKM1/2 ratios in control and c-Myc knockdown cells determined as in FIG. 3a.

FIG. 18: c-Myc knockdown in HeLa cells does not change PKM splicing. a, Immunoblotting using HeLa cells transiently expressing control or human c-Myc-targeting shRNAs. b, PKM1/2 ratios in control and c-Myc knockdown cells determined as in FIG. 2a.

FIG. 21: PTB, hnRNPA1, and hnRNPA2 are required for high PKM2:PKM1 mRNA ratios. a, Scheme for assaying PKM1/PKM2 ratios in human cells. b, Immunoblots showing protein levels after the indicated siRNA treatment. Protein bands were quantified after LI-COR Odyssey scanning and normalized to GAPDH. c, The indicated splicing factors were depleted by siRNA, followed by PKM splicing assay outlined in (a). Products corresponding to M1 and M2 are indicated with arrows. The PKM1 percentage is indicated below. d, PKM1/2 levels assayed after the indicated siRNA treatment in 293 cells.

FIG. 22: Expression of PTB/A1/A2 and c-Myc correlates with PKM2 expression in C2C12 cells and tumors. a, PKM splicing assay after the indicated number of days of C2C12 differentiation. b, Immunoblots for the indicated proteins were performed throughout differentiation, and normalized to GAPDH (Day 0=1). c, RNA was extracted from brain tissue or tumor samples and assayed for PKM mRNA isoforms. d, Lysates were immunoblotted for PTB, hnRNPA1, hnRNPA2 or c-Myc and normalized to Actin. Sample order is the same for RT-PCR and immunoblotting.

FIG. 23: c-Myc upregulates PTB/A1/A2 alters PKM splicing. a, Immunoblotting using NIH-3T3 cells stably expressing control or c-Myc-targeting shRNAs. Signals were quantified and normalized to actin. b, RT-PCR using the same cell lines as in (a). Realtime RT-PCR was performed separately to quantify the relative levels of PTB/A1/A2 mRNAs in control and c-Myc knockdown cells, using RPL13A as a reference gene. Relative levels of each are shown below each panel, with s.d. indicated (n=3). c, PKM1/2 ratios in control and c-Myc knockdown cells determined as in FIG. 2a, d, A model for PKM splicing regulation. Top, in adult tissues, low expression of PTB/A1/A2 allows for recognition of E9 by the splicing machinery and disrupts intronic structures favorable for E10 inclusion. Bottom, in embryonic and cancer cells, PTB/A1/A2 are upregulated, bind to splicing signals flanking E9 and repress its inclusion. Binding of these proteins around E9 and possibly to other sites creates an intronic structure favorable to E10 inclusion.

DETAILED DESCRIPTION

Figures 1A, 1B, 1C, 1D:
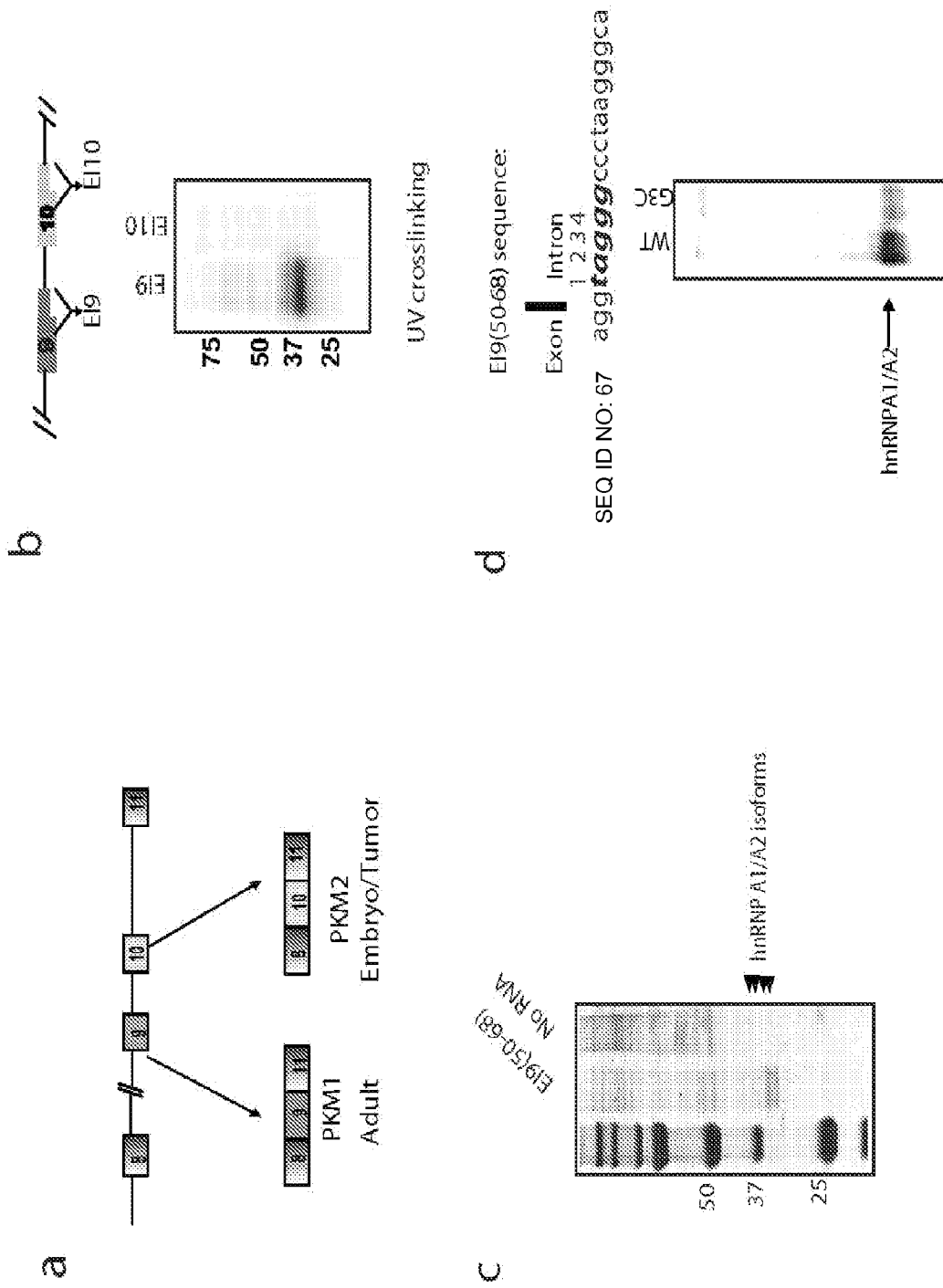
FIG. 1: hnRNP proteins bind specifically to sequences flanking E9. a, Schematic diagram of PKM splicing. b, Position of probes spanning the E9 or E10 5' splice sites is indicated (top). After UV crosslinking, proteins were resolved by SDS-PAGE and detected by autoradiography (bottom). c, RNA affinity chromatography using a 19 nt biotinylated RNA corresponding to the mapped site of strong crosslinking. Bound proteins were separated by SDS-PAGE and Coomassie stained. Positions of bands excised for mass spectrometry are indicated. d, Sequence of EI9(50-68), putative hnRNP A1/A2 binding site indicated in bold italics (top). UV crosslinking with wild-type RNA, or an RNA with a mutation in the putative hnRNP A1/A2 binding site (bottom). e, Position of probes spanning the E9 or E10 3' splice site. UV crosslinking using I8E9 or I9E10 substrates. f, After UV crosslinking as in panel (e) reactions were IPed with either α-PTB (BB7) or α-HA antibodies. g, UV crosslinking with short RNAs corresponding to the final 48 nt of intron 8 (I8) or intron 9 (I9), sequences indicated above, lanes 1 and 2. Putative PTB binding sites in I8 are underlined, and the indicated mutations were introduced in I8mu. UV crosslinking was performed as above (lanes 3 and 4).

The terms "treatment" or "treat" as used herein include treating, preventing, ameliorating, and/or decreasing the severity of the symptoms of a disease or disorder, or improving prognosis for recovery.

The term "nucleotide" refers to a ribonucleotide or a deoxyribonucleotide. In certain embodiment the nucleotide is a modified form thereof, or an analog thereof. Nucleotides may include species that comprise purines, e.g., adenine, hypoxanthine, guanine, and their derivatives and analogs, as well as pyrimidines, e.g., cytosine, uracil, thymine, and their derivatives and analogs.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

In certain embodiments, modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. Other examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide may also include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group. Further, in certain embodiments the term nucleotide also includes those species that have a detectable label, such as for example a radioactive or fluorescent moiety, or mass label attached to the nucleotide.

In certain aspects, the invention provides a combination of inhibitory RNAs against hnRNPA1, hnRNPA2 and PTB. In certain embodiments, the combination of inhibitory RNAs against hnRNPA1, hnRNPA2 and PTB has a therapeutic effect. In certain embodiments, the therapeutic effect is observed as, for example but not limited, reduced cell growth of cancer cells which express PKM2. In certain aspects, the invention provides a composition comprising inhibitory RNAs against hnRNPA1, hnRNPA2 and PTB. In certain aspects, the invention provides a composition consisting essentially of inhibitory RNAs against hnRNPA1, hnRNPA2 and PTB. In certain aspects, the invention provides a composition consisting of inhibitory RNAs against hnRNPA1, hnRNPA2 and PTB. In certain aspects, the invention provides a composition comprising inhibitory RNAs against hnRNPA1, and hnRNPA2. In certain aspects, the invention provides composition consisting essentially of inhibitory RNAs against hnRNPA1, and hnRNPA2. In certain aspects, the invention provides composition consisting of inhibitory RNAs against hnRNPA1, and hnRNPA2. The compositions of the inventions can be used in any of the methods described herein.

In certain aspects, the invention is directed to methods comprising, consisting essentially of, or consisting of a step of inhibiting or reducing the expression of PKM2 in cells or tissues that express PKM2, the methods comprising, consisting essentially of, or consisting of contacting the cells or tissues with compositions comprising inhibitory RNAs against hnRNPA1, hnRNPA2 and PTB, whereby hnRNPA1, hnRNPA2 and PTB are reduced or depleted.

In certain embodiments, the expression of PKM2 is developmentally inappropriate, for example, but not limited to PKM2 expression in cancer cells. In certain embodiments, the invention does not include methods which use inhibitory RNAs against the individual targets hnRNPA1, hnRNPA2 or PTB. Thus in certain embodiments, the invention provides methods which use a combination of at least two inhibitory RNA molecules targeting any combination of hnRNPA1, hnRNPA2 or PTB, whereby the targeted mRNA (protein) is reduced or depleted. The inventors have discovered that the simultaneous knockdown of all three proteins hnRNPA1, hnRNPA2 and PTB leads to the largest increases in PKM1/2 ratio. In other embodiments, the invention provides methods which use a combination of three inhibitory RNA molecules targeting hnRNPA1, hnRNPA2 and PTB, whereby the targeted mRNAs (protein) are reduced or depleted.

Also provided are methods of treating diseases, disorders, or conditions associated with elevated or developmentally inappropriate expression of PKM2 comprising, consisting essentially of, or consisting of administering to a subject in need thereof, or a cell, or a tissue, an effective amount of any of the compositions of the instant invention. In yet another embodiment, the instant invention is directed to methods of treating PKM2-expressing cancers, using a combination of inhibitory RNA molecules against hnRNPA1, hnRNPA2 and/or PTB as described herein. The invention is also directed to methods for inhibiting cell growth of cancer cells which inappropriately express PKM2.

In certain embodiments, the methods of the invention comprise the step of delivering to a subject or cell an effective amount of any of the compositions of the invention. In another embodiment, the methods of the invention consist essentially of the step of delivering to a subject or cell an effective amount of any of the compositions of the invention. In another embodiment, the methods of the invention consist of the step of delivering to a subject or cell an effective amount of any of the compositions of the invention.

Knock Down of hnRNPA1, hnRNPA2 and/or PTB

Gene silencing mechanisms, including RNAi mechanisms and its use as a tool for therapeutic applications are known in the art. See eg. López-Fraga M, Martinez T, Jiménez A. "RNA interference technologies and therapeutics: from basic research to products." *BioDrugs.* 2009; 23(5):305-32 and references cited therein; Lu P Y, Xie F, Woodle M C "In vivo application of RNA interference: from functional genomics to therapeutics." *Adv Genet.* 2005; 54:117-42; Liu G, Wong-Staal F, Li Q X. "Development of new RNAi therapeutics." *Histol Histopathol.* 2007 February; 22(2):211-7; Dallas A, Vlassov A V. "RNAi: a novel antisense technology and its therapeutic potential." *Med Sci Monit.* 2006 April; 12(4): RA67-74;

Antisense nucleotide technology has been a described approach in protocols to achieve gene-specific interference, and is known in the art. In certain embodiments, an RNA interference (RNAi) technology is used to decrease or inhibit expression of the nucleic acid against which the RNAi is directed.

Methods to design and make inhibitory RNAs against a specific target are known in the art. A non-limiting example of such method is described in Schramm & Ramey, "siRNA design including secondary structure target site prediction", *Nature Methods* 2, (2005); Chalk and Sonnhammer, "siRNA specificity searching incorporating mismatch tolerance data" *Bioinformatics* 2008 24(10):1316-1317 Inhibitory RNA may be synthesized either in vivo or in vitro. Once made, the siRNA can be introduced directly into a cell to mediate RNA interference. The siRNAs can also be introduced into cells via transient or stable transfection.

An RNAi expression vector can be a replicable nucleic acid construct used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell or tissue. In general, expression vectors of utility in recombinant DNA techniques are often in the form of "plasmids" which refer to circular double stranded DNA loops which, wherein the vector may or may not become integrated in the chromosome. In the present specification, "plasmid" and "vector" are used interchangeably as the plasmid is the most commonly used form of vector. The invention contemplates other forms of expression vectors which serve equivalent functions and which become known in the art subsequently.

A number of expression vectors have also been developed to continually express siRNAs in transiently and stably transfected mammalian cells. Some of these vectors have been engineered to express small hairpin RNAs (shRNAs), which get processed in vivo into siRNA-like molecules capable of carrying out gene-specific silencing. In certain embodiments, an shRNA contains plasmid under the control of a promoter, for example a U6 promoter. Another type of siRNA expression vector encodes the sense and antisense siRNA strands under control of separate pol III promoters. The siRNA strands from this vector, like the shRNAs of the other vectors, have 3' thymidine termination signals. The shRNA gene can be delivered via a suitable vector system, e.g., adenovirus, adeno-associated virus (AAV), or retrovirus. In certain embodiments, the invention contemplates use of RNAi vectors which permit stable transfection, and continuous reduction or inhibition of the function of the target protein.

In certain embodiments, the RNA may comprise one or more strands of polymerized ribonucleotide. It may include modifications to either the phosphate-sugar backbone or the nucleoside. For example, the phophodiester linkages of natural RNA may be modified to include at least one of a nitrogen or sulfur heteroatom. Modifications in RNA structure may be tailored to allow specific genetic inhibition while avoiding a general panic response in some organisms which can be generated by dsRNA. Likewise, bases may be modified to block the activity of adenosine deaminase. RNA may be produced enzymatically or by partial/total organic synthesis; any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). In certain embodiments, RNA containing a nucleotide sequences identical to a portion of the target gene are suitable for attenuation and/or inhibition target protein activity. In certain embodiments, RNA sequences with insertions, deletions, and single point mutations relative to the target sequence can be effective for inhibition. Thus, one hundred percent sequence identity between the RNA and the target sequence is not required to attenuate and/or inhibit target activity. Sequence identity between the iRNA and the target of about 99%, 98%, 97%, 96%, 95%, 94%, 93%, 92% or 91% is contemplated of the antagonists and the methods of the present invention. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

In certain embodiments, the iRNAs are "small interfering RNAs" or "siRNAs," which are known and described in the art. The siRNA may be double stranded, and may include short overhangs at each end. The overhangs are 1-6 nucleotides in length at the 3' end. It is known in the art that the siRNAs can be chemically synthesized, or derived from a longer double-stranded RNA or a hairpin RNA. The siRNAs have significant sequence similarity to a target RNA so that the siRNAs can pair to the target RNA and result in sequence-specific degradation of the target RNA through an RNA interference mechanism. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described herein. In certain embodiments, the siRNA constructs can be generated by processing of longer double-stranded RNAs, for example, in the presence of the enzyme dicer. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In other embodiments, the antisense construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the deleterious effects are preferred.

In certain embodiments, the RNAi construct is in the form of a hairpin structure (i.e., hairpin RNA). The hairpin RNAs can be synthesized exogenously or can be formed by transcribing from RNA polymerase III promoters in vivo. In certain embodiments, such hairpin RNAs are engineered in cells or in an animal to ensure continuous and stable suppression of a desired gene. It is known in the art that siRNAs can be produced by processing a hairpin RNA in the cell.

Provided herein are inhibitory RNAs directed to hnRNPA1, hnRNPA2 or PTB. In one embodiment the inhibitory RNAs are described in Example 1. Antisense modulators of hnRNPA1 are provided in USPatent 6165789. The sequences of hnRNPA1, hnRNPA2 and PTB are known in the art and available in public sequence databases.

Methods of Delivering Inhibitory RNAs.

A therapeutically effective amount or dose refers to that amount of an inhibitory RNA, as an active ingredient, designed to inhibit the expression of a target gene. In certain embodiments, the inhibitory RNA is useful to treat, prevent and/or ameliorate pathological conditions. In certain embodiments, the pathological condition is associated with PKM2 expression. In certain embodiments, the pathological condition is associated with of hnRNPA1, hnRNPA2 and PTB. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact amount will be determined by the practitioner, in light of factors related to the subject that requires treatment. Amount and administration are adjusted to provide sufficient levels of the active ingredient or to maintain the desired effect. Factors that may be taken into account include the severity of the disease state, location of the affected tissue or cells within the body, general health of the subject, age, weight, and gender of the subject, diet, time and frequency of administration, drug combination(s), reaction sensitivities, and tolerance/response to therapy.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ formulations suitable for the inhibitory RNAs of the invention.

Delivery methods of the inhibitory RNAs can be tailored to particular cells or tissues, disease or conditions, locations of tumors, and other relevant factors.

Various methods for delivery of RNAi therapeutics, including cell and tissue specific delivery have been described. See e.g., Lu P Y, Woodle M C.: "Delivering small interfering RNA for novel therapeutics" Methods Mol. Biol. 2008; 437:93-107, and references cited therein; Saghir Akhtar and Ibrahim F. Benter: "Nonviral delivery of synthetic siRNAs in vivo" *J. Clin. Invest.* 117(12): 3623-3632 (2007); Huricha Baigude, Dr., Tariq M. Rana "Delivery of Therapeutic RNAi by Nanovehicles", *ChemBioChem.* Volume 10 Issue 15, Pages 2449-2454; Keller M. "Nanomedicinal delivery approaches for therapeutic siRNA." Int J. Pharm. 2009 Sep. 11; 379(2):210-1; Meade B R, Dowdy S F. "The road to therapeutic RNA interference (RNAi): Tackling the 800 pound siRNA delivery gorilla." Discov Med. 2009 December; 8(43):253-6.

In non-limiting examples, the inhibitory RNAs may be delivered by suitable vectors which comprise shRNAs encoding the inhibitory RNAs. In other embodiments, delivery of the inhibitory RNAs is lipid and lipid-like materials mediated. See e.g., Akin Akinc et al. "Development of Lipidoid-siRNA Formulations for Systemic Delivery to the Liver", *Molecular Therapy* (2009) 17 5, 872-879. In other embodiments, the inhibitory RNAs are delivered as chemically modified or otherwise modified molecules, such that their in vivo targeting and/or stability is improved.

In certain embodiments, the RNAi therapeutic compositions of the invention are used for treatment of brain tumors. For methods of delivery of inhibitory RNAs to the brain, see e.g. William M. Pardridge "shRNA and siRNA delivery to the brain" *Advanced Drug Delivery Reviews*, Volume 59, Issues 2-3, 30 Mar. 2007, Pages 141-152; Saroj P Mathupala, "Delivery of small-interfering RNA (siRNA) to the brain" *Expert Opinion on Therapeutic Patents*, February 2009, Vol. 19, No. 2, Pages 137-140; PCT Publication WO2008033285.

In a non-limiting example, U.S. Ser. No. 11/627,863 describes methods for the delivery of compounds with pharmacological and biological activity, including siRNAs, using targeting peptides that have preferential binding affinity for lung tissue. For methods of RNAi delivery to immune cells, see Kortylewski et al., "In vivo delivery of siRNA to immune cells by conjugation to a TLR9 agonist enhances antitumor immune responses" Nature Biotechnology 27, 925-932 (2009); Published online: 13 Sep. 2009.

The terms tumor and cancer are used interchangeably. In certain embodiments, the tumor is a tumor of neuroectodermal origin. The tumor of neuroectodermal origin can be a member of the group consisting of glioma, meningioma, ependymoma, medulloblastoma, neuroblastoma, ganglioma, pheochromocytoma, melanoma, peripheral primitive neuroectodermal tumor, small cell carcinoma of the lung, and Ewing's sarcoma. In certain embodiments a cancer or cancer cell which can be treated by any of the methods of the invention is a lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual or reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, chronic or acute leukemia, lymphocytic lymphomas, cancer of the bladder, cancer of the kidney, renal cell carcinoma, neoplasms of the central nervous system (CNS), neuroectodermal cancer, spinal axis tumors, glioma, meningioma, and pituitary adenoma.

EXAMPLES

Example 1 c-Myc Promotes Pyruvate Kinase M2 Alternative Splicing in Cancer Cells by Upregulation of Specific hnRNP Proteins Cancer cells take up glucose and convert it to lactate while avoiding oxidative phosphorylation. This phenomenon is critical for maximal tumorigenicty and is in part explained by the almost universal reversion of tumors to the embryonic form of pyruvate kinase, PKM2. PKM2 and the adult isoform, PKM1, are produced from the same gene, differing by a single mutually exclusive mRNA exon. Here we show that three hnRNP proteins, PTB, hnRNPA1 and hnRNPA2, control this splicing event, by binding repressively to sequences flanking the PKM1-specific exon, resulting in production of PKM2. We also demonstrate that the oncogenic transcription factor c-Myc upregulates PTB/A1/A2 expression, ensuring a high PKM2:PKM1 ratio. Establishing a relevance to cancer, we show that human gliomas overexpress c-Myc and PTB/A1/A2 in a manner that strongly correlates with PKM2 expression. Our results thus define a pathway that regulates an alternative splicing event required for tumor cell proliferation.

When oxygen is abundant, quiescent cells use glucose primarily for oxidative phosphorylation, while under the same conditions tumor cells convert most glucose to lactate, a phenomenon known as aerobic glycolysis, first described by Otto Warburg early last century[1]. Aerobic glycolysis is now thought to be a general characteristic of proliferating cells, and is important for cell growth[3-5]. Aerobic glycolysis, however, is a comparatively inefficient means of producing energy, and vertebrates have evolved mechanisms aimed at ensuring that aerobic glycolysis only occurs in growing cells, where it is necessary to support growth. One such mechanism hinges on tight control of pyruvate kinase (PK) isoform expression. PK is the glycolytic enzyme that produces pyruvate, the fate of which determines the glycolytic phenotype of the cell. Pyruvate produced by the fetal isoform, PKM2, is preferentially converted to lactate, a step necessary for the high rates of glycolysis observed in tumor cells, while pyruvate produced by the adult isoform, PKM1, is preferentially used for oxidative phosphorylation[4]. PKM2, but not PKM1 is regulated by the binding of tyrosine phosphorylated peptides, which results in release of the allosteric activator fructose 1-6 bisphosphate and inhibition of PK activity[6]. Because widespread tyrosine phosphorylation occurs as a result of many growth factor-initiated signaling pathways, this regulatory mechanism is proposed to allow cells stimulated by growth factors to use glycolytic intermediates in biosynthetic pathways essential for cell proliferations[5,6].

Consistent with a critical role in proliferation, re-expression of PKM2 in tumors is robust, occurring in all cancers examined[4,7]. The importance of this reversion was underscored by experiments in which replacement of PKM2 with PKM1 in tumor cells resulted in markedly reduced growth[4]. Proliferation associated switching from PKM1 to PKM2 occurs in stimulated lymphocytes[8] in a manner that precisely matches a switch to aerobic glycolysis in the same cell type[2], providing further evidence for an intimate link between cell growth, aerobic glycolysis, and PKM isoform switching.

PKM1 and PKM2 mRNAs are transcribed from the same gene, and differ only in inclusion of a single mutually exclusive exon, exon 9 (E9) in PKM1 and exon 10 (E10) in PKM2 (FIG. 1a), separated by a short (~400 nucleotide) intron in the pre-mRNA. Proliferation/quiescence associated PKM isoform switching is therefore the result of a remarkably tightly regulated alternative splicing (AS) event[4,8]. A quantitative genome-wide analysis of AS by deep sequencing indicated that while transcripts from almost all human genes undergo at least some AS, PKM is one of a very small number of mutually exclusively spliced genes that undergo near complete AS switching between cell types[9]. Such dramatic switching likely reflects important and opposing functions for PKM1 and PKM2 in determining the cell's metabolic phenotype, which makes it essential that the organism exclusively express the correct isoform in the appropriate cell type. Here we describe a pathway that results in tight proliferation-linked regulation of PKM AS, in which three critical hnRNP proteins, which can be upregulated by the oncogenic transcription factor c-Myc, simultaneously promote E9 repression and E10 inclusion, resulting in PKM2 expression in growing cells.

hnRNP Proteins Bind E9 Splicing Elements

Figure 7:
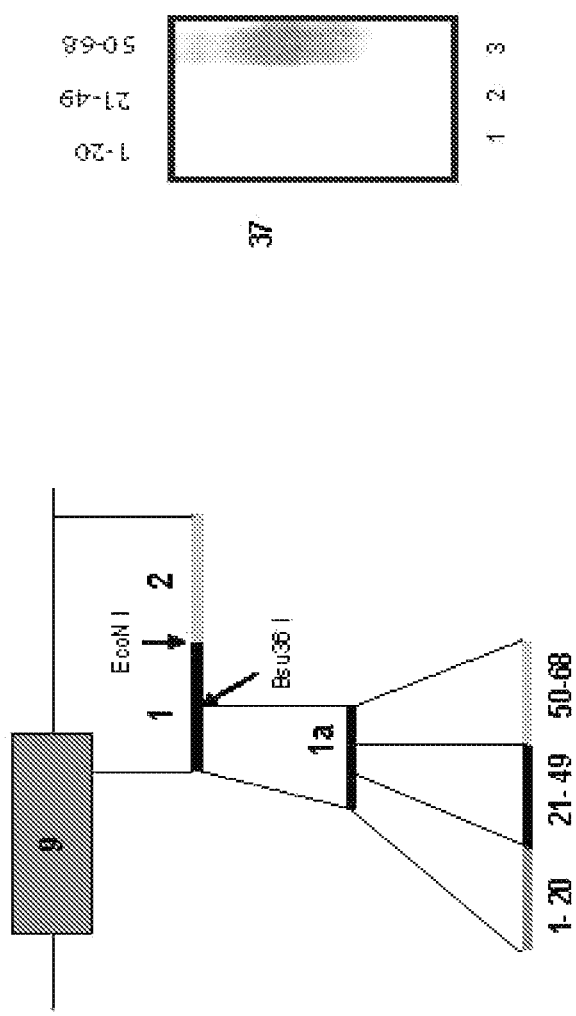
FIG. 7: Mapping of strong ~35-40 kDa crosslinking in the EI9 substrate. Truncations in EI9 were introduced with the indicated restriction enzymes (left). Strong crosslinking mapped to EI(1a). Sections of EI9(1a) were cloned and used for UV crosslinking in HeLa NE.
Figure 8:
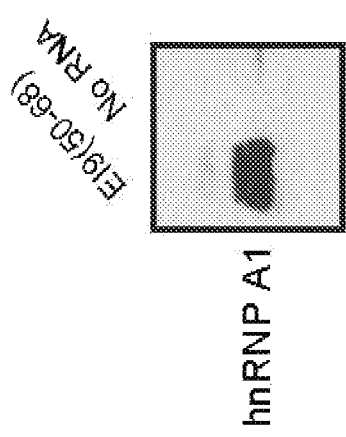
FIG. 8: hnRNP A1 binds to EI9(50-68). After RNA affinity chromatography using biotinylated EI9(50-68), protein samples from EI9(50-68) (lane 1) and no RNA control (lane 2) were separated on 10% SDS-PAGE and analyzed by immunoblotting using an anti-hnRNP A1 antibody.

We first set out to identify RNA binding proteins that might regulate PKM alternative splicing. To this end, we prepared an [α-$^{32}$P]-UTP labeled 250 nucleotide (nt) RNA spanning the E9 5' splice site (EI9), previously identified as inhibitory to E9 inclusion[10], as well as a labeled RNA from a corresponding region of E10 (EI10) (FIG. 1b), and used these in UV crosslinking assays with HeLa nuclear extracts (NE)[11]. After crosslinked, RNase-treated proteins were separated by SDS-PAGE, multiple intense bands from 35-40 kDa appeared using the EI9 substrate, while little evidence of binding was observed using the EI10 substrate (FIG. 1b). We mapped the tight binding of these proteins to a 19 nt region we named EI9(50-68) that spans the E9 5' splice site (FIG. 7). To identify the 35-40 kDa proteins, we performed RNA affinity chromatography using a 5' biotin-labeled 19 nt RNA oligonucleotide corresponding to the mapped binding site. After separation of bound proteins by SDS-PAGE and Coomassie staining, the pattern of specifically bound proteins closely matched that observed after UV crosslinking (FIG. 1c). The four indicated protein bands between 35-40 kDa were excised, and identified by mass spectrometry as isoforms of hnRNP A1 and hnRNP A2, RNA binding proteins with well established roles as sequence-specific repressors of splicing (e.g., refs. 11, 12). This result was confirmed by immunoblotting with antibodies against hnRNP A1 (FIG. 8).

Figure 9:
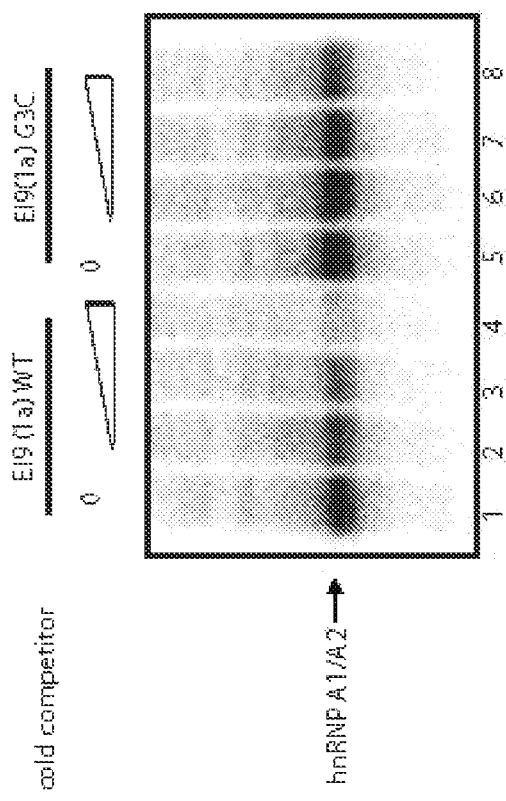
FIG. 9: hnRNP A1 binding to EI9(1a) is specifically decreased by G3C mutation. $^{32}$P-UTP labeled EI9(1a) RNA (see diagram in Supplementary FIG. 1) was incubated with HeLa NE, in the presence of increasing amount (0, 1.5, 3, 7.5 μM) of cold WT EI9(1a) RNA (lanes 1-4) or cold EI9(1a) G3C mutant RNA (lanes 5-8), followed by UV crosslinking.

The sequence immediately downstream of the E9 5' splice site contains a UAGGGC sequence identical to an hnRNP A1-dependent ESS found in the FGF receptor K-SAM exon[12], and is highly related to the consensus hnRNP A1 high affinity binding site identified by SELEX, UAGGG(A/U)[13] (FIG. 1d). Consistent with mutational studies of the K-SAM ESS[12], mutation of the G3 nucleotide of this motif to C led to a large decrease in hnRNP A1/A2 crosslinking (FIG. 1d). Reduced binding of A1/A2 to the mutant was confirmed in competition assays in which 7.5 µM wild type unlabeled competitor RNA reduced A1/A2 crosslinking to a radioactive wild-type probe by 70% while the same concentration of unlabeled G3C RNA reduced crosslinking by only 30% (FIG. 9). These data confirm the location of hnRNP A1/A2 binding as immediately downstream of the E9 5' splice site.

Figures 1E, 1F:
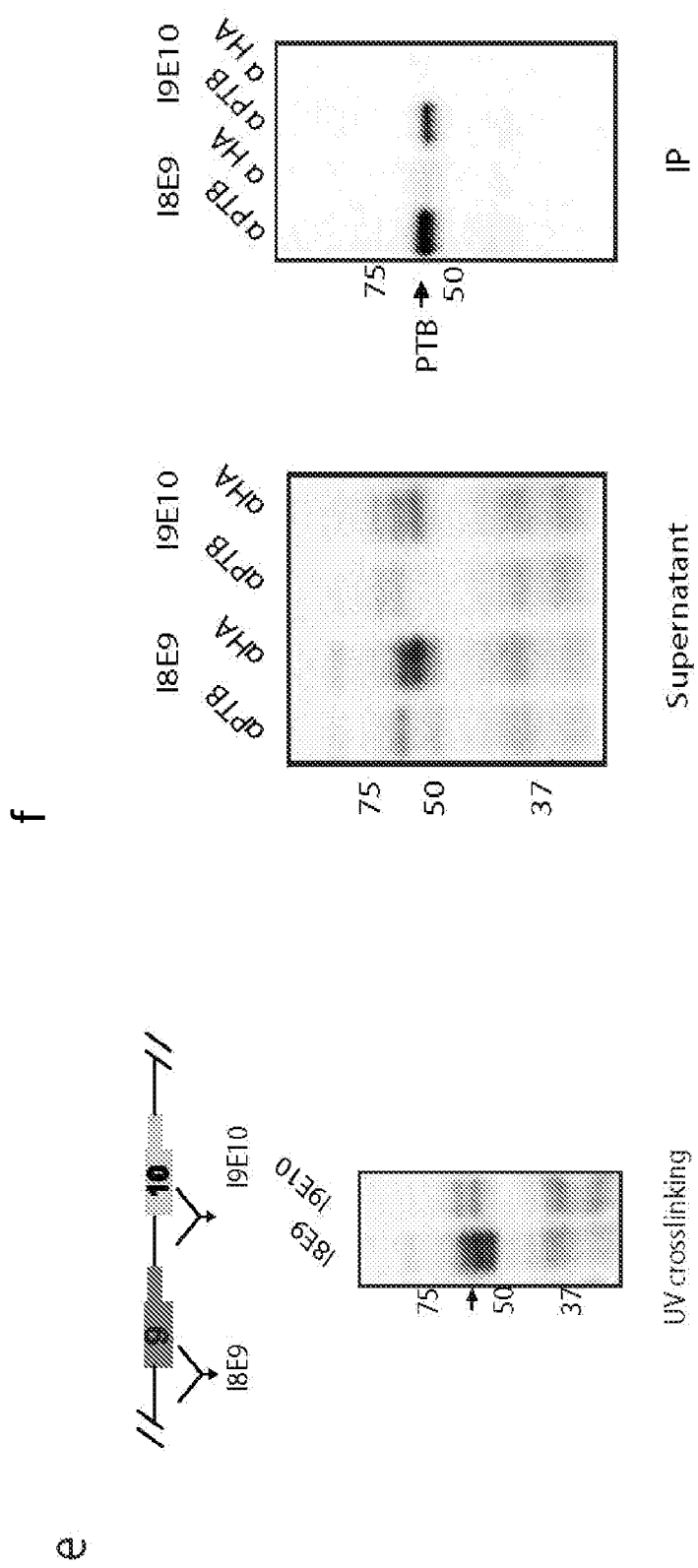
Figure 1G:
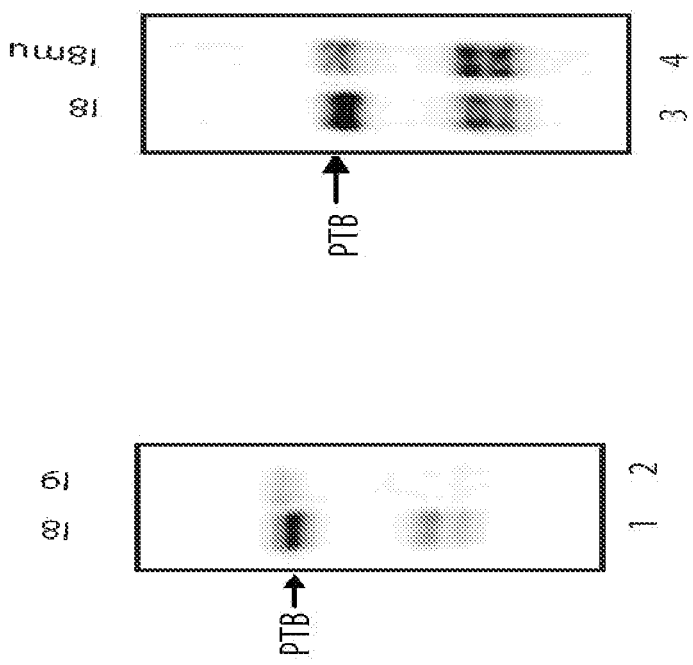
Figure 10:
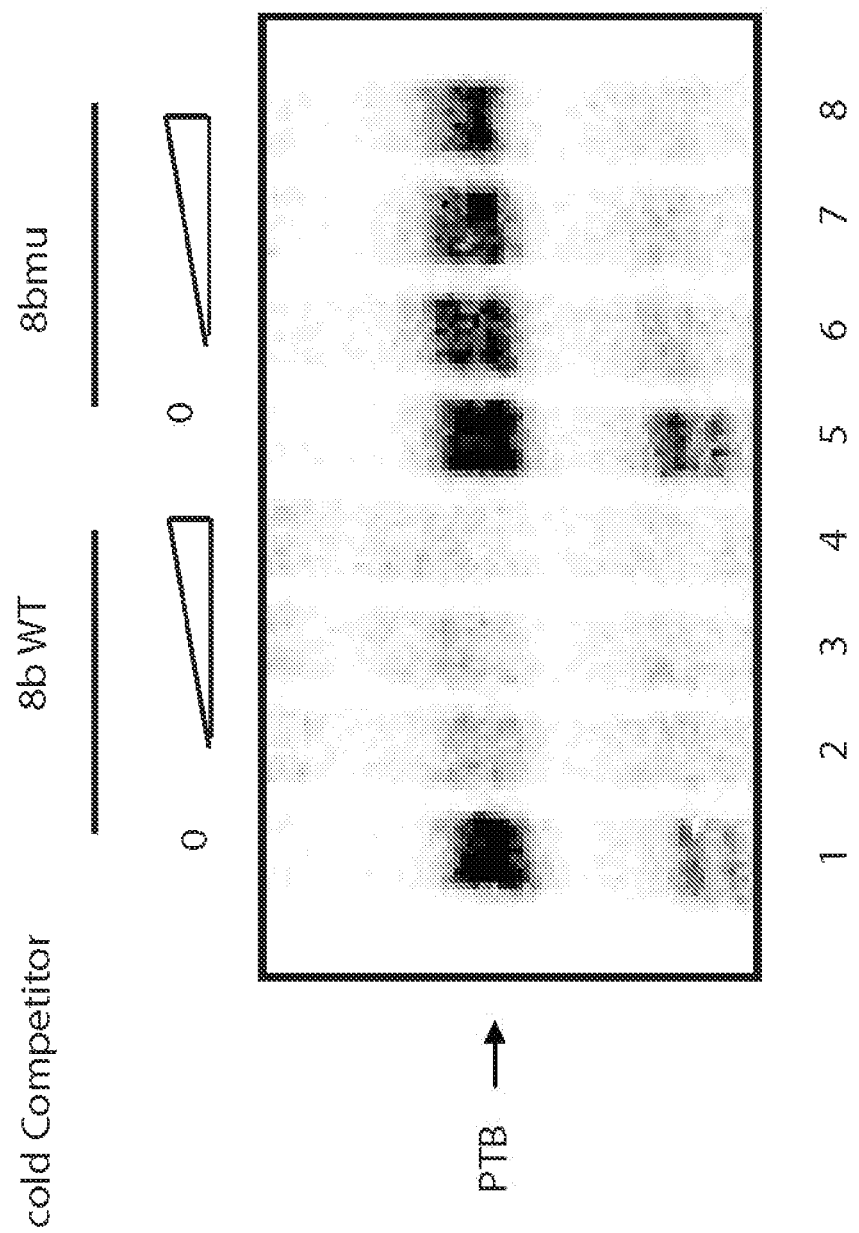
FIG. 10: PTB binding to I8 RNA is specifically abolished by a C to G mutation. $^{32}$P-UTP labeled I8 RNA (see sequence in FIG. 1) was incubated with HeLa NE in the presence of increasing amounts (0, 2, 3, 3 6 μM) of cold I8 WT RNA (lanes 1-4) or cold I8mu RNA (lanes 5-8), followed by UV crosslinking.

To explore the possibility that other splicing regulators bind upstream of E9 or E10, we constructed UV crosslinking substrates 225 nt in length spanning the 3' splice sites of E9 (probe I8E9) or E10 (probe I9E10) (FIG. 1e), and performed UV crosslinking as above. After separation by SDS-PAGE, a strong band at 55 kDa was observed using the I8E9 probe, while I9E10 showed much weaker crosslinking at 55 kDa (FIG. 1e). Inspection of the polypyrimidine tract upstream of E9 revealed two potential PTB binding sequences (UCUUC)[14] within 35 nucleotides of the intron/exon boundary, while no such sequence exists in close proximity of E10. PTB (polypyrimidine tract binding protein, or hnRNP I) frequently functions as a splicing repressor. PTB binding sites are often enriched upstream of exons upregulated in brain, skeletal muscle and heart[15], tissues that also display high PKM1/PKM2 ratios[16]. We therefore speculated that the 55 kDa crosslink observed using I8E9 is PTB. To confirm this, we carried out immunoprecipitation (IP) with anti-PTB antibodies. The 55 kDa strongly crosslinked I8E9 protein was specifically depleted from NE with PTB antibody while a much weaker crosslink obtained with I9E10 was also revealed to be PTB (FIG. 10. To identify more precise regions of PTB binding, we constructed shorter crosslinking substrates (48 nt) that span the polypyrimidine tract upstream of each exon. Using these RNAs, UV crosslinking showed strong PTB binding to the I8 RNA probe, but not to the I9 probe (FIG. 1g). Mutation of the two putative PTB binding sites from UCUUC to UGUUC significantly diminished crosslinking (FIG. 1g), and cold competitor RNA containing these mutations competed poorly with wild-type RNA for PTB binding (FIG. 10).

Figure 11C:
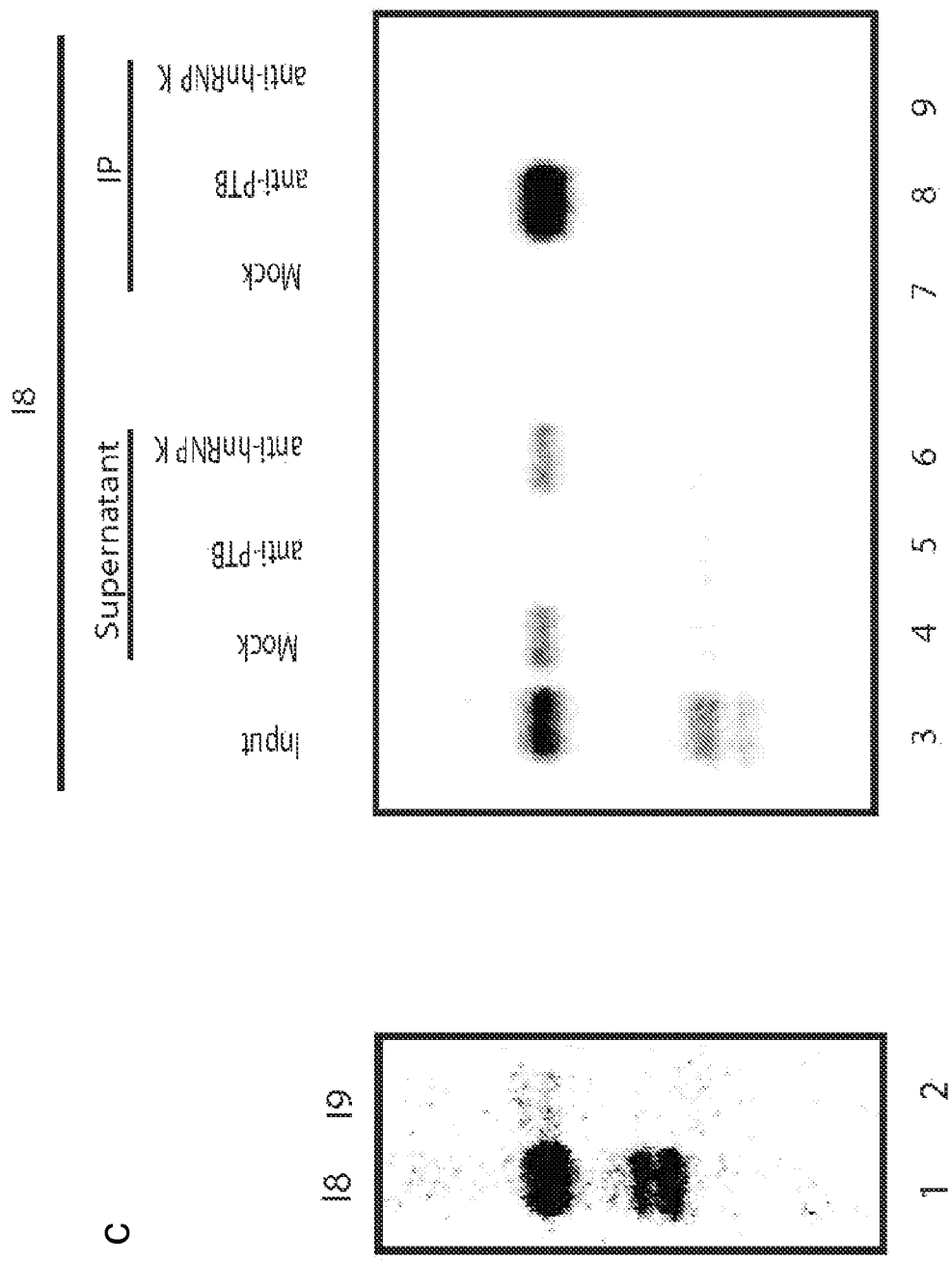
FIG. 11: a, PTB binds to biotinylated RNA oligo I8. After affinity chromatography using biotinylated I8 RNA supernatants (lanes 1 and 2) and protein samples bound to the beads from I8 (lane 4) and no RNA control (lane 3) were separated on 10% SDS-PAGE and analyzed by immunoblotting using an anti-PTB antibody (BB7). b, After RNA affinity chromatography using biotinylated I8, protein samples bound to the beads from I8 (lane 2) and no RNA control (lane 1) were separated on 10% SDS-PAGE and Coomassie stained. Positions of bands excised for mass spectrometry are indicated. c, Using [$^{32}$p]-CTP to label I8 and I9 substrates, crosslinking was performed. Using [$^{32}$p]-CTP labeled I8, crosslinked NE was IPed using the indicated antibodies.

We also used a biotinylated version of the I8 probe for RNA affinity purification. This approach confirmed strong binding of PTB to this sequence (FIG. 11a). RNA affinity chromatography followed by mass spectrometry identified PTB plus three additional proteins in splicing: poly(C) binding protein 1, poly(C) binding protein 2 (PCBP1 and PCBP2), and hnRNP K (FIG. 11b). Previous experiments have implicated these proteins in several cellular processes other than splicing[17-19]. Additionally, further crosslinking and mutational experiments suggested that PTB binds I8 RNA with significantly higher affinity than these proteins and we have therefore not pursued them further.

Figure 12:
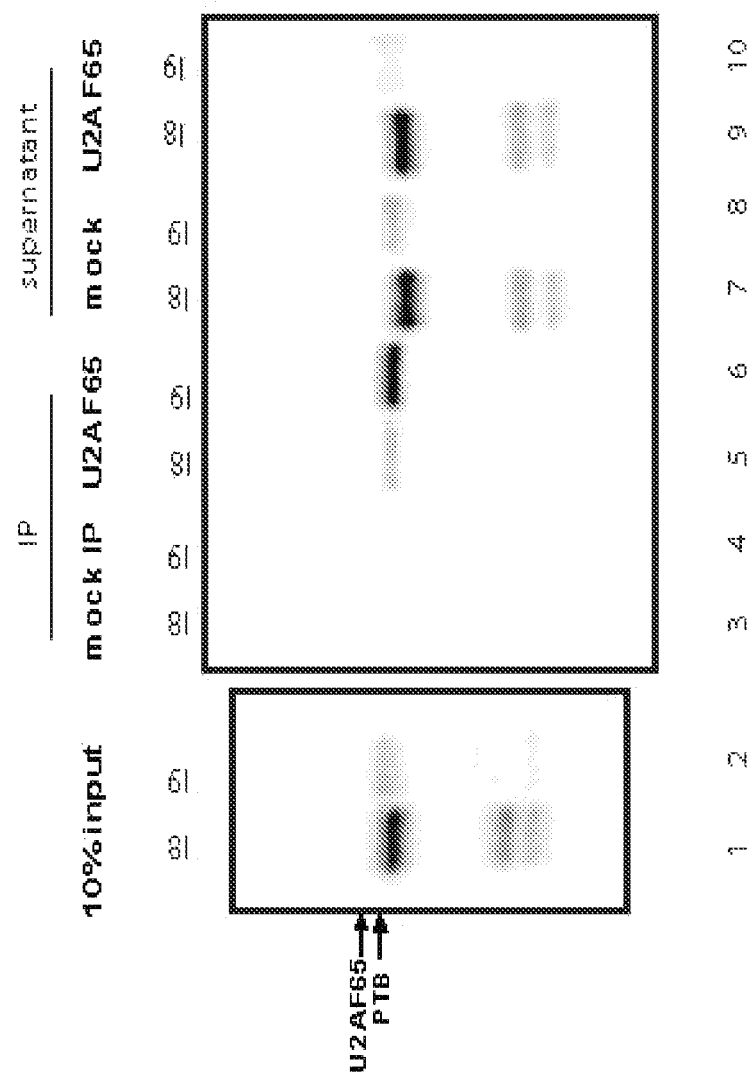
FIG. 12: U2AF65 binds poorly to the polypyrimidine tract of E9, but strongly to that of E10. Alignment of a short probe corresponding to the final 48 nt of human and mouse I8 and I9. UV crosslinking was performed as above. Immunoprecipitation with αU2AF65 antibodies confirmed the identity of the 65 kDa band as U2AF65 (lanes 5 and 6).

We also observed a UV crosslink at approximately 65 kDa with the I9 RNA (FIG. 1g). We speculated that this protein may be the essential splicing factor U2AF65, which binds to the polypyrimidine tract at an early step in spliceosome assembly[20]. To test this, after crosslinking, we performed IP using an α-U2AF65 antibody. The IP revealed significantly stronger binding of U2AF65 to the I9 probe than the I8 probe (FIG. 12). This suggests that PTB competes with U2AF65 for binding to I8, but not I9, reflecting a frequent mechanism of PTB splicing repression[21].

PTB/A1/A2 Promote PKM2 Expression

Figures 2C, 2D, 2E:
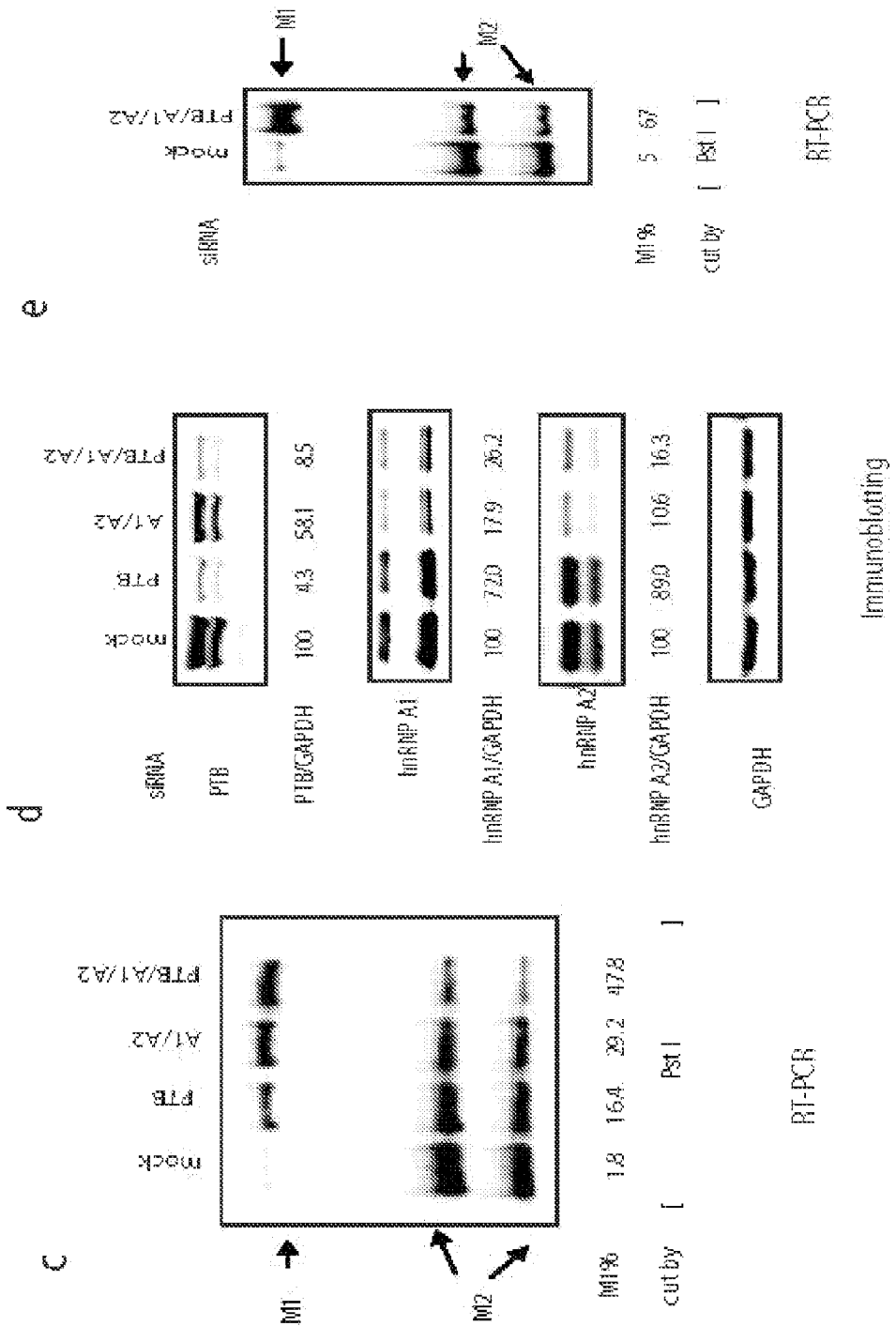
FIG. 2: PTB, hnRNP A1, and hnRNP A2 are required for high PKM2:PKM1 mRNA ratios. a, Scheme for assaying PKM1/PKM2 ratios in human cells. After PCR using primers in exons 8 and 11, products are digested by restriction enzymes specific for E9 (Tth111 I) or E10 (Pst I). b, The indicated splicing factors were depleted by siRNA, followed by RNA extraction and the RT-PCR PKM splicing assay outlined in (a). PCR products for the PKM amplicon and a load control, μglobulin, are displayed at left. The PKM amplicons after cutting with the indicated enzyme are shown in the middle and right panels. Products corresponding to M1 and M2 are indicated with arrows. c, Simultaneous knockdown of PTB/A1/A2 followed by PKM splicing assay. The PKM1 percentage is indicated below. d, Immunoblots showing protein levels after the indicated siRNA treatment. Protein bands were quantified after LI-COR Odyssey scanning and normalized to GAPDH. e, PKM1/2 levels assayed after the indicated siRNA treatment in 293 cells.
Figure 13:
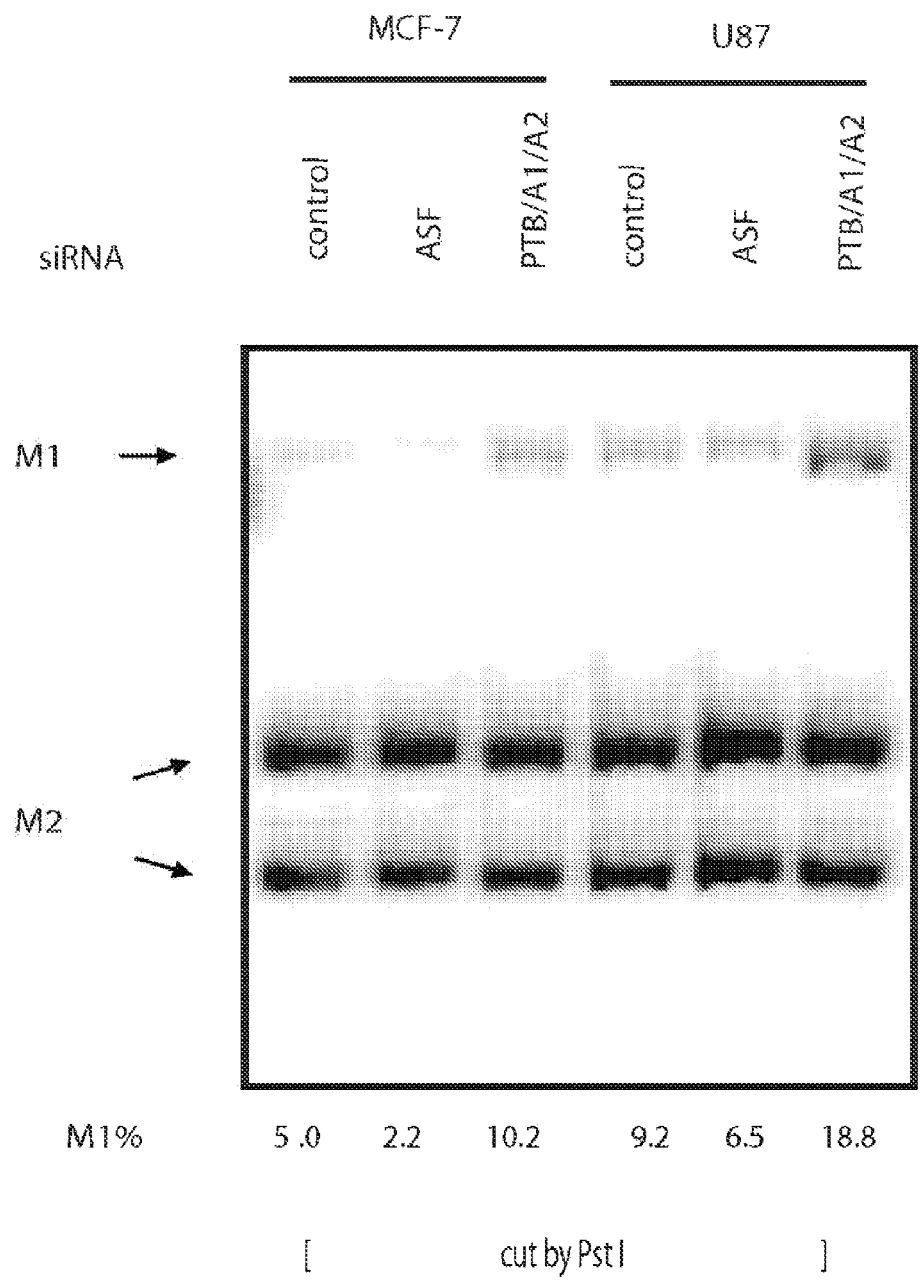
FIG. 13: Assay of PKM splicing after siRNA depletion of ASF/SF2, or simultaneous knockdown of PTB/A1/A2. siRNAs were transfected into human breast cancer cell line MCF-7 (lanes 1-3 and 7-9) and glioblastoma cell line U87 (lanes 3-6 and 10-12). Cells were collected after three days. Total RNA was extracted and PKM isoform ratio was estimated as described in FIG. 2.

Because the locations of hnRNP A1/A2 and PTB binding sites flanking E9 overlap elements critical to exon inclusion (the polypyrimidine tract for PTB[16], the site of U1-pre-mRNA base-pairing for A1/A2[22]), we speculated that these proteins are inhibitors of E9 inclusion. To examine this possibility, we used siRNA to deplete hnRNPA1, hnRNPA2 and/or PTB from HeLa cells. We assayed PKM isoforms using RT-PCR with [$\alpha$-$^{32}$P]-dCTP to amplify a region from E8 to E11, followed by digestion using a restriction endonuclease specific for E9 or E10 (FIG. 2a). After separation by PAGE and phosphorimager scanning, bands were quantified to calculate relative abundance of PKM1/2. Knockdown of hnRNP A1, hnRNP A2, or the SR protein ASF/SF2 in HeLa cells resulted in little change in splicing pattern (FIG. 2b). Because we have previously observed functional redundancy of hnRNP A1/A2[11], we simultaneously depleted both proteins. This resulted in no change in overall PKM transcript levels, but a sharp increase in PKM1 mRNA, and a concomitant decrease in PKM2 mRNA (FIG. 2b). Quantification indicated that upon A1/A2 double knockdown, the PKM1/2 ratio in HeLa cells increased from approximately 2% in the control to 29% in the double knockdown (FIG. 2c). In addition, PTB knockdown also increased the PKM1 isoform, to 16% (FIG. 2b, c). Next, we simultaneously depleted all three factors (FIG. 2d), which further increased PKM1 levels, to about 48% (FIG. 2c). Similar results were obtained using 293 cells, with the triple knockdown resulting in an increase from 5% to 67% PKM1 (FIG. 2e). Increases in PKM1 mRNA upon A1/A2/PTB knockdown were observed in all cell lines tested, including the breast cancer cell line MCF-7 and the glioblastoma cell line U87 (FIG. 13).

Figure 14:
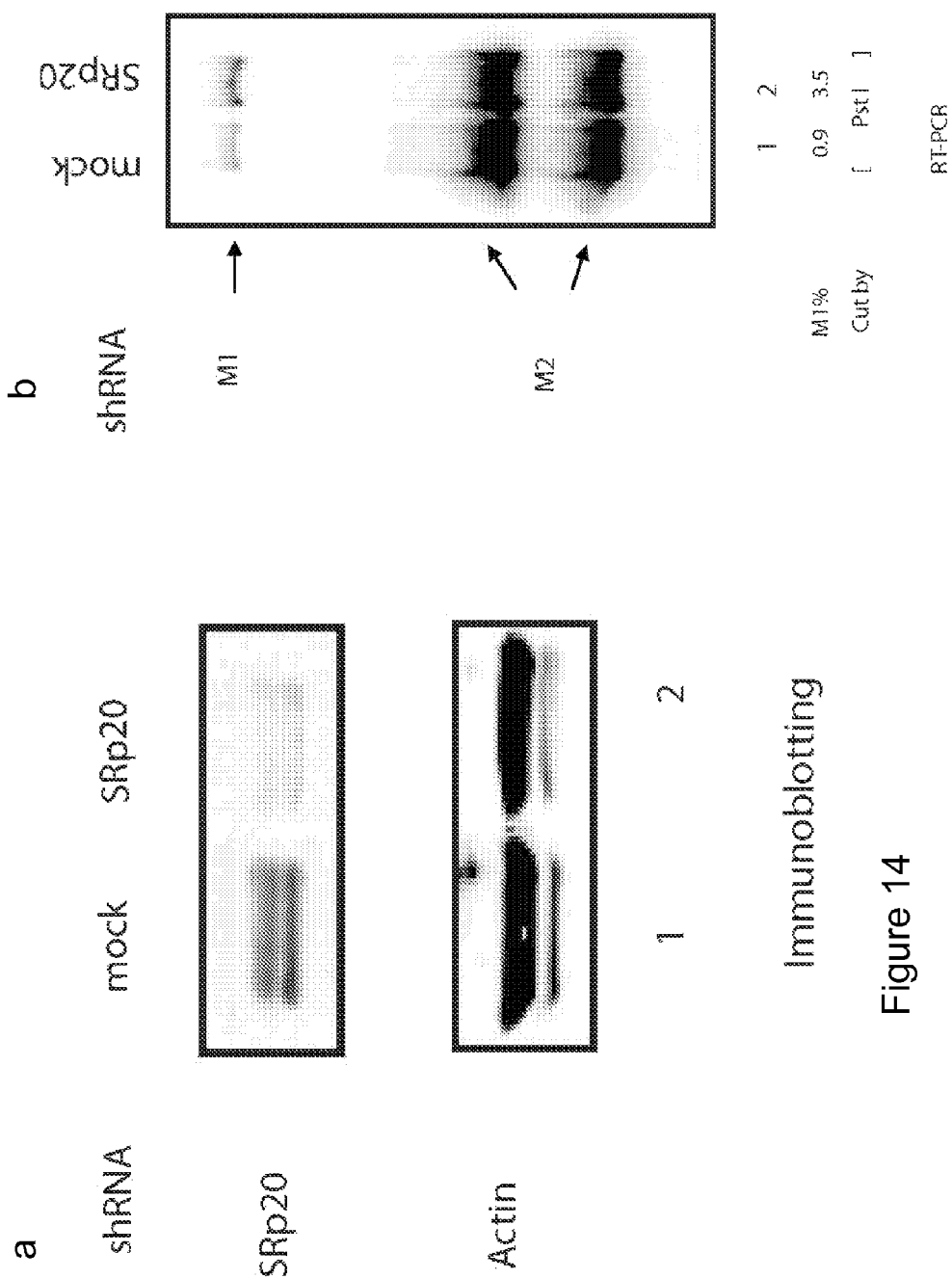

To examine the specificity of the effects seen in the PTB/A1/A2 knockdowns, we depleted two additional cancer and proliferation-associated splicing factors, ASF/SF2[23], and SRp20[24]. Knockdown of ASF/SF2 resulted in a slight increase in PKM2 mRNA (FIG. 2b), while SRp20 knockdown, while slowing cell growth, failed to significantly affect PKM splicing (FIG. 14), providing evidence that the effects observed upon PTB/A1/A2 knockdown were specific. Together, our results indicate that PTB and hnRNP A1/A2 are the major suppressors of the adult PKM1 isoform and promote the production of PKM2 in transformed human cell lines.

PTB/A1/A2 Expression Correlates with PKM2

Figure 3A:
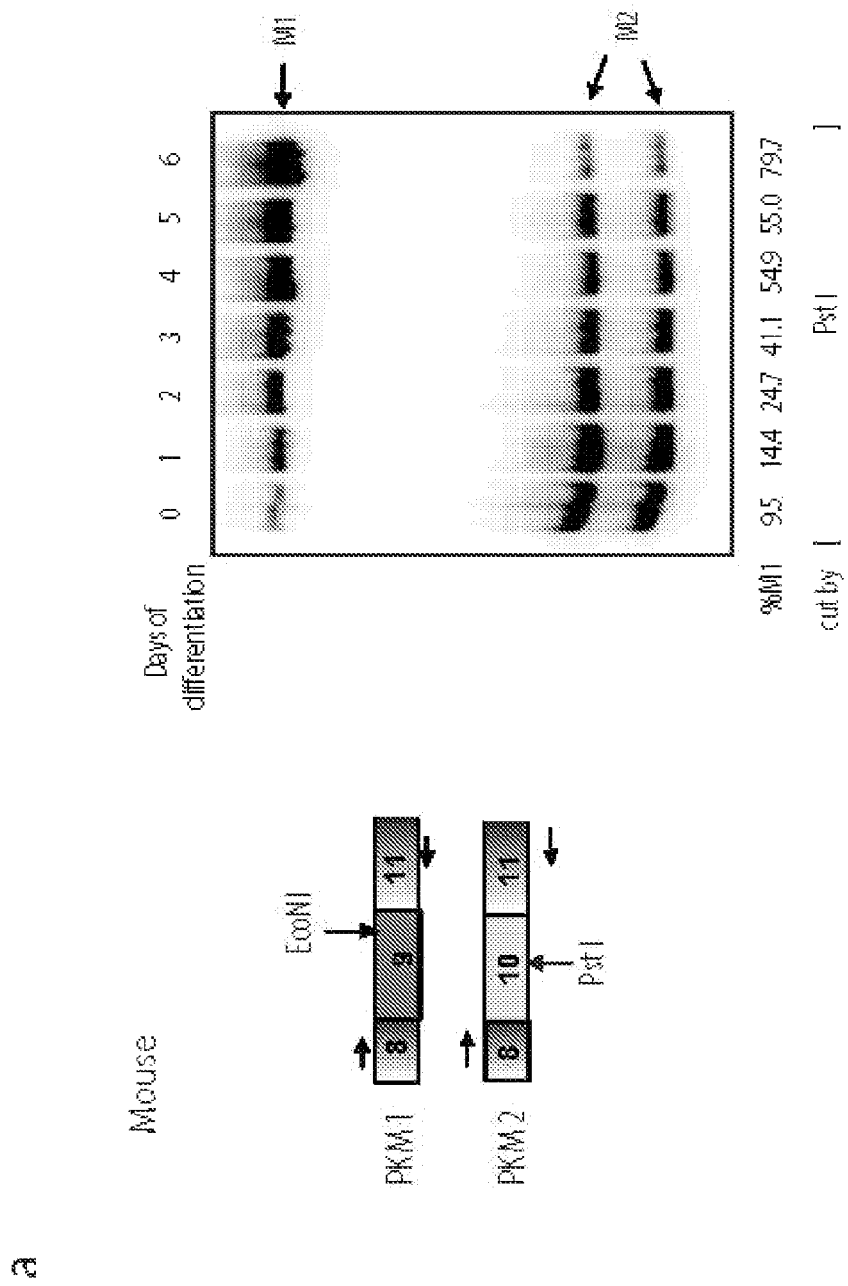
FIG. 3: PKM1 upregulation correlates with reduced PTB/A1 expression during C2C12 differentiation. a, Schematic for assay of PKM splicing by RT-PCR in mouse (left). PKM splicing assay after the indicated number of days of C2C12 differentiation (right). b, Immunoblots for the indicated proteins were performed throughout differentiation, and normalized to GAPDH (Day 0=1).
Figure 3B:
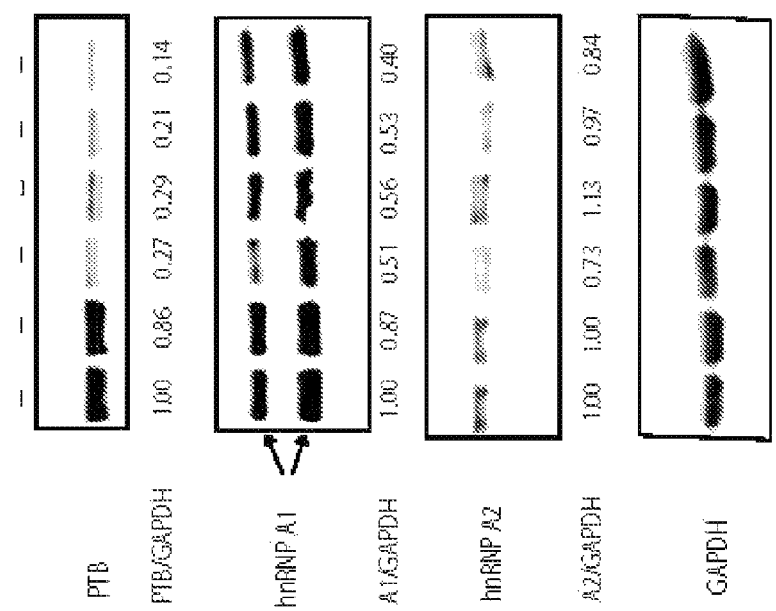
Figure 15A:
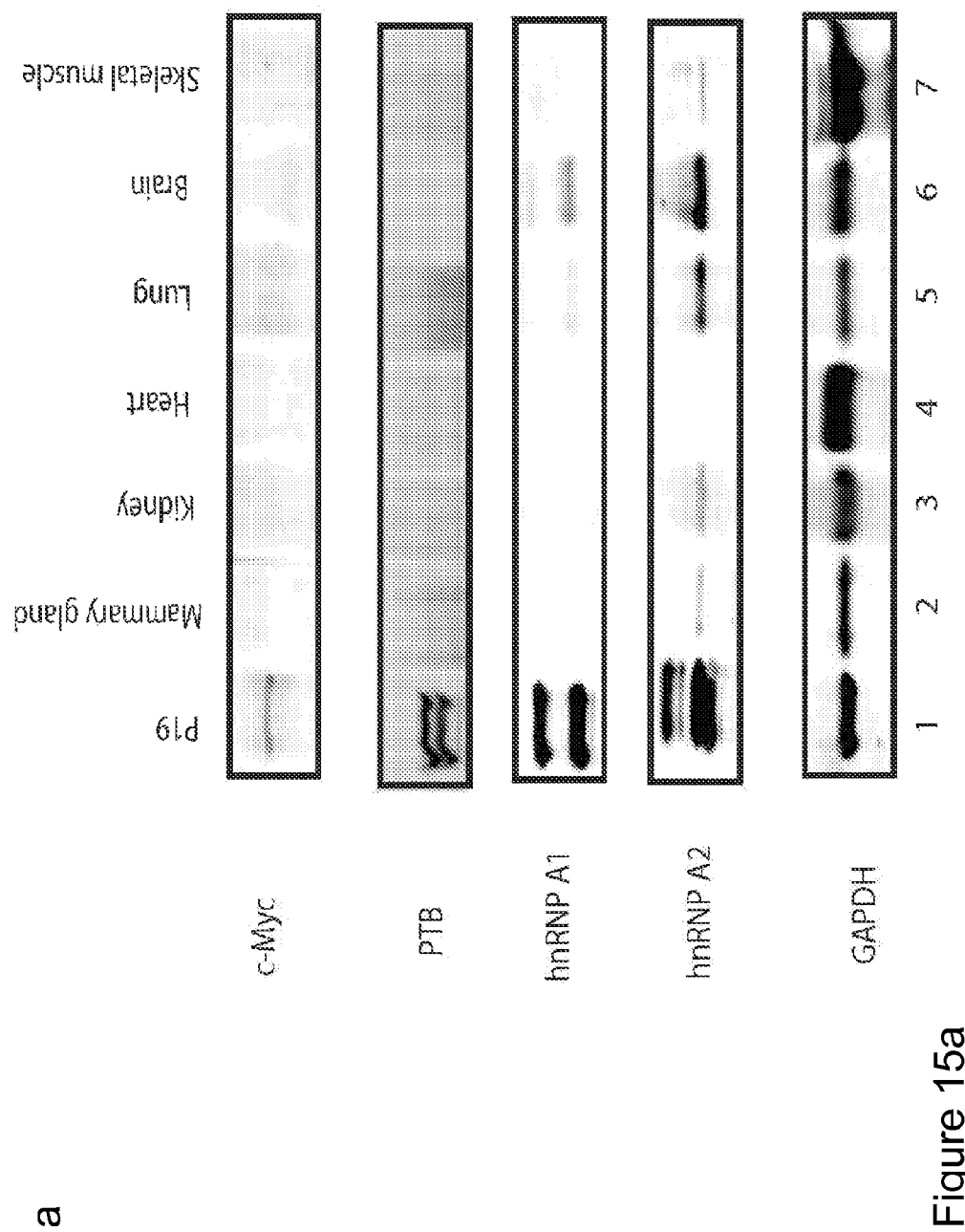
FIG. 15: PTB/A1/A2 proteins and PKM2 mRNA are expressed at lower levels in adult tissues than in P19 cells. a, Immunoblotting against c-Myc, PTB, hnRNP A1, hnRNP A2 and GAPDH as loading control using lysates from P19 cells (lane 1) or indicated mouse tissues (lanes 2-7). b, RT-PCR examining PKM1/2 ratio in P19 cells (lane 1) and mouse tissues (lanes 2-7).
Figure 15B:
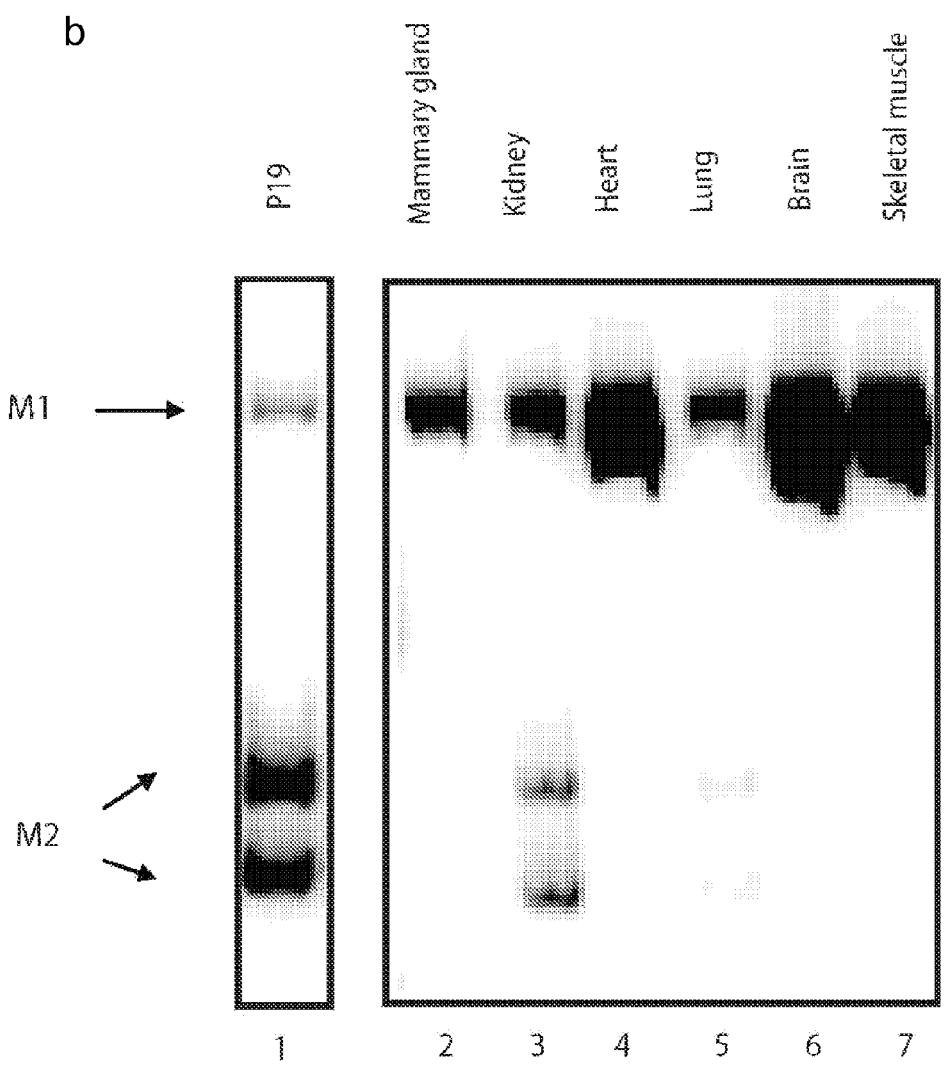

Because of their effect on PKM splicing in HeLa and 293 cells, we next examined potential correlations between PTB/A1/A2 expression levels and PKM1/2 alternative splicing. Analysis of PTB/A1/A2 protein levels in mouse tissues revealed that the expression of these proteins in all tissues examined was considerably lower than in a growing cell line, P19, and consistent with this, the five tissues tested all had far lower levels of PKM2 than P19 cells (FIG. 15). We also examined whether changes in PTB/A1/A2 levels correlate with changes in PKM splicing during switching from growth to quiescence. To this end, we used the mouse myoblast cell line C2C12, which, when grown to confluence and then switched to low-serum medium, undergoes myogenic differentiation, a process that includes PKM2 to PKM1 switching[25]. We differentiated C2C12 cells for 6 days, and used RT-PCR followed by restriction digest to assess the PKM1/2 ratio each day. We observed a large increase in PKM1 and a corresponding decrease in PKM2 during differentiation (FIG. 3a). We then prepared cell lysates from C2C12 cells at time points throughout differentiation and examined protein levels by immunoblotting (FIG. 3b). PTB expression dropped over 70% by day 3 of differentiation, after which it remained stable, consistent with previous studies[26]. We also observed an approximately 50% decrease in hnRNP A1 levels by day 3 of differentiation, though no significant changes were observed in the level of hnRNP A2.

Figure 4A:
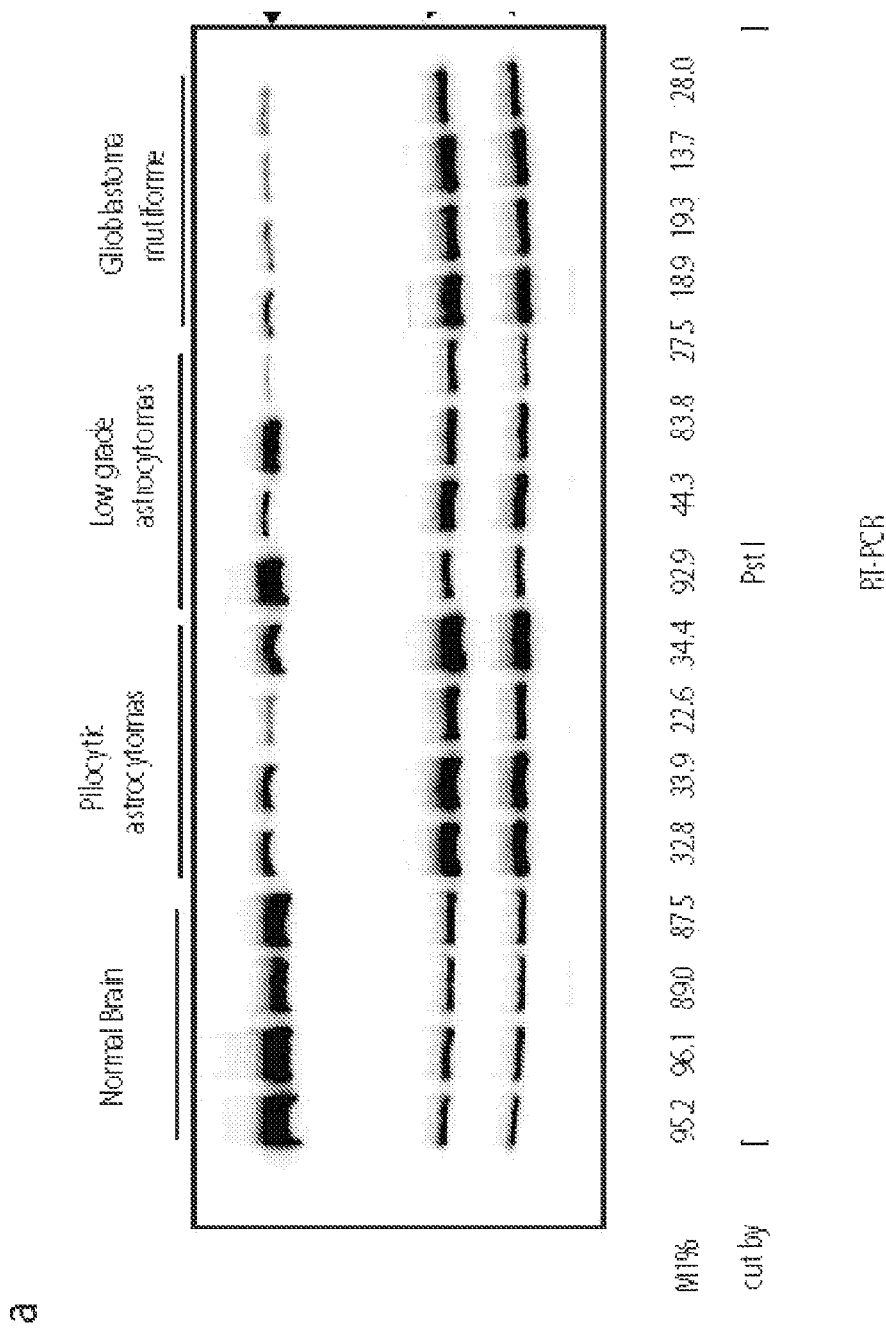
FIG. 4: Overexpression of PTB/A1/A2 correlates with PKM2 expression in tumors. a, RNA was extracted from brain tissue or tumor samples and assayed for PKM mRNA isoforms. b, Lysates were immunoblotted for PTB, hnRNP A1 or hnRNP A2, and normalized to actin. Sample order is the same for RT-PCR and immunoblotting.
Figure 4B:
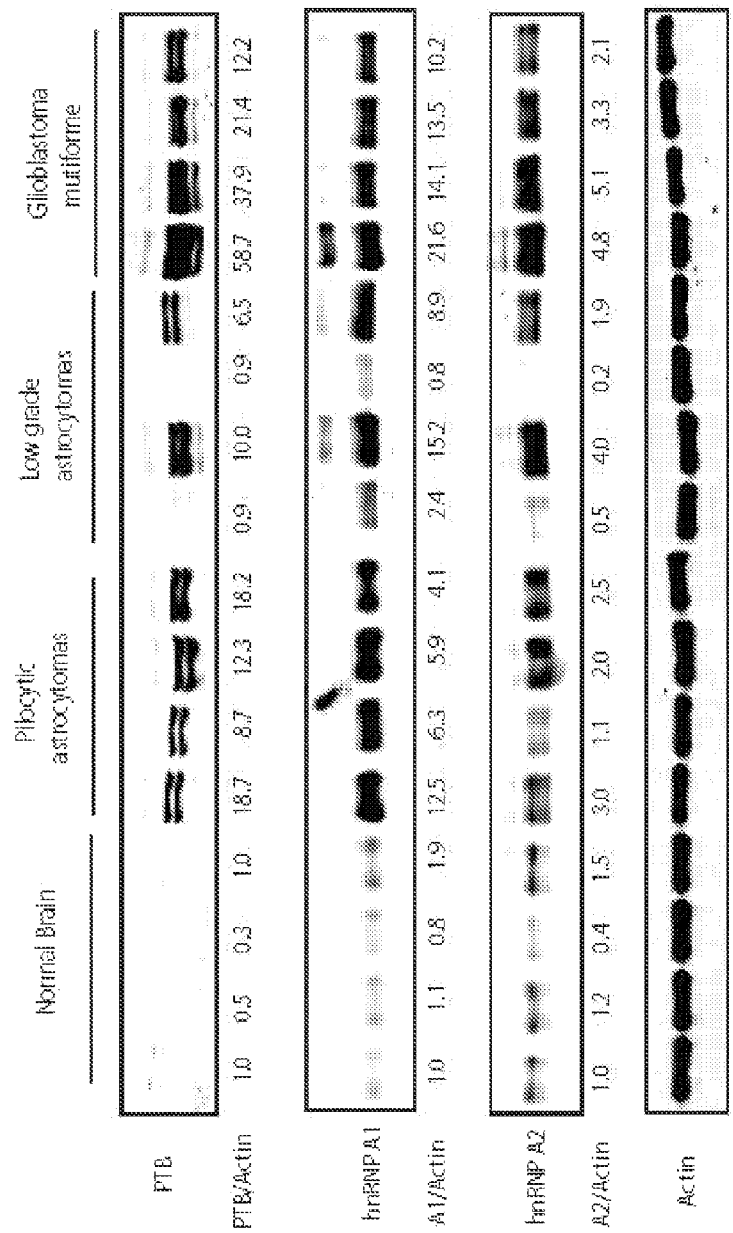

Because of the importance of the PKM2 isoform to the growth of cancer cells, we next examined human glioma tumor samples for a correlation between PTB/A1/A2 expression and PKM splicing. We first assayed PKM1/2 mRNA levels as described earlier. Normal brain tissue ranged from 4-13% PKM2, pilocytic astrocytomas (PA) samples expressed approximately 66-77% PKM2, low grade astrocytomas (LGA) ranged from 7-73%, and glioblastoma multiforme (GBM) samples expressed 72-86% PKM2 (FIG. 4a). To explore a potential correlation between elevated PKM2 mRNA levels and expression of the regulatory proteins we identified, we performed immunoblots for PTB, hnRNP A1, and hnRNP A2. Significantly, all high-PKM2 tumors expressed elevated levels of PTB/A1/A2, with the most striking overexpression in GBMs (FIG. 4b). Consistent with their uniformly high PKM2 expression, all four PA samples also showed overexpression of the PTB/A1/A2. In LGAs the two high PKM2 tumors showed elevated expression of the three proteins, while the two low PKM2 tumors showed expression levels similar to normal brain. Because LGAs are highly infiltrative[27], resected tumor samples of this type are necessarily a mixture of tumor cells and uninvolved cells; therefore our failure to detect high PKM2 in two samples may reflect only the composition of the small portion of tumor we obtained. However, LGAs frequently exhibit very low levels of glucose uptake in comparison with PAs and GBMs[28]; the low PKM2-expressing LGAs we report here may thus reflect known metabolic characteristics of this tumor type.

Figure 16:
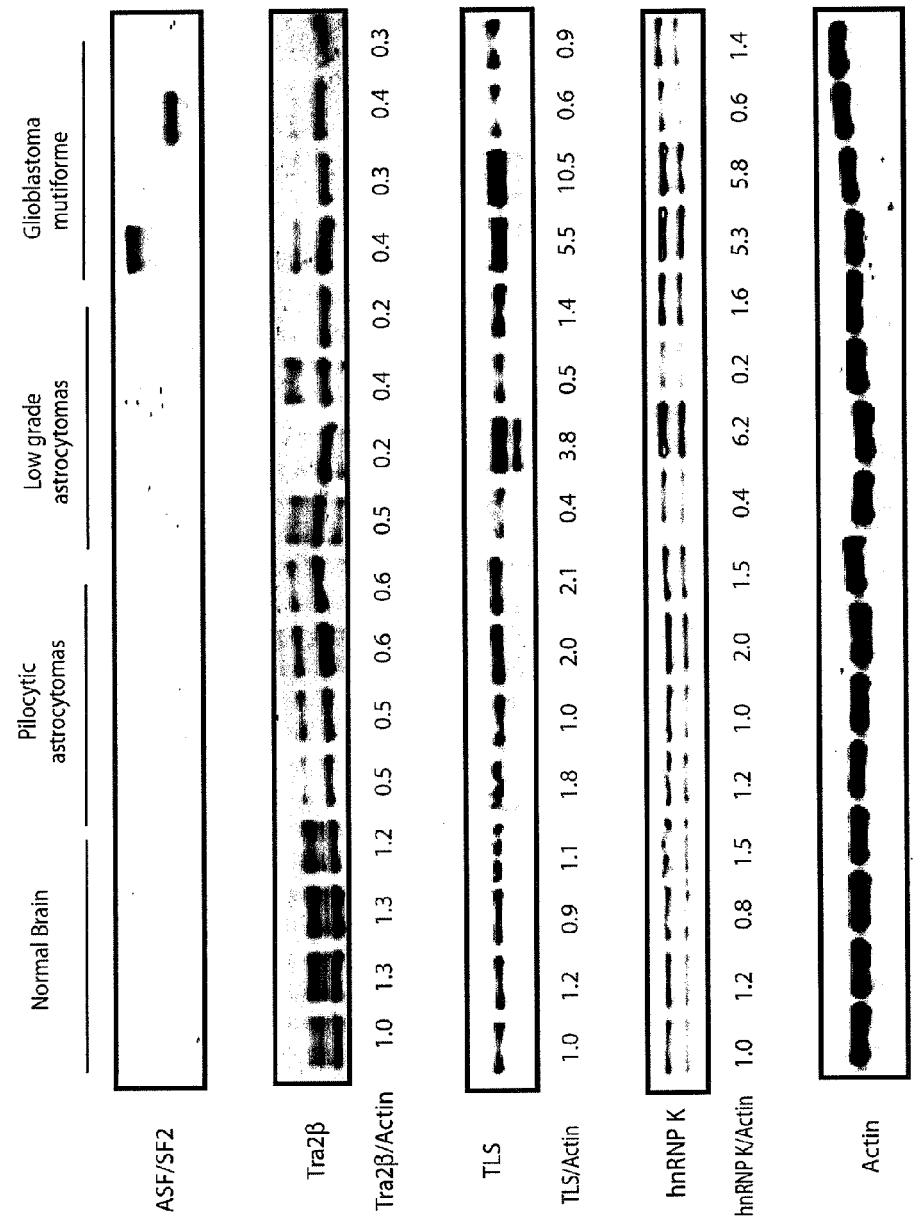
FIG. 16: Lysates of normal brain and glioma samples were immunoblotted for ASF/SF2, Tra2β, TLS and hnRNP K and normalized to actin. Quantitation of each protein is indicated below each immunoblot (normal brain sample one=1). Sample order is the same as for RT-PCR and immunoblotting in FIG. 4.

To examine whether the perfect correlation between PKM2 splicing and PTB/A1/A2 overexpression that we observed in gliomas is specific or reflects a general overexpression of splicing factors in cancer, we analyzed expression of four additional splicing factors, three of which have been shown to be upregulated in cancer (FIG. 16). ASF/SF2, an SR protein overexpressed in some cancers and shown to behave as an oncogene[23], was overexpressed in only two GBMs. Tra2[3], an SR-type splicing regulator overexpressed in breast cancer[29], was actually downregulated in all gliomas. TLS/FUS, an hnRNP-type protein was overexpressed in only a fraction of PKM2-expressing gliomas. hnRNP K, which has also been shown to be overexpressed in cancer[30], displayed a sporadic pattern of overexpression. Our results indicate that the correlation between an elevated PKM2/1 mRNA ratio and overexpression of PTB, hnRNP A1 and hnRNP A2 is specific and not reflective of a general property of splicing factors.

c-Myc Promotes PKM2 Splicing

The tight coupling of PKM2 expression to proliferation suggests that the expression of the PKM splicing regulatory proteins we identified might be under the control of a proliferation-associated regulatory mechanism. A strong candidate for such a role is the oncogenic transcription factor c-Myc, which like PTB/A1/A2, is upregulated in GBMs[31]. It is noteworthy that in two independent genome-wide screens of transcription factor binding in mouse embryonic stem cells, as well as in human cancer cells, the oncogenic transcription factor c-Myc has been found to bind the promoters of the PTB, hnRNP A1, and hnRNP A2 genes[32-34]. Consistent with this, comparison of the human and mouse PTB and hnRNP A1 promoters reveals canonical E-box sequences (CACGTG)[35] within 500 base pairs of the transcription start site. Importantly, in a variety of genome-wide microarray and proteomic studies, c-Myc expression has been shown to result in upregulation of all three RNA binding proteins found here to promote PKM2 splicing[36-38]. c-Myc upregulation of proteins that promote the PKM2 isoform would be in keeping with known effects of c-Myc in promoting aerobic glycolysis[39].

Figure 5A:
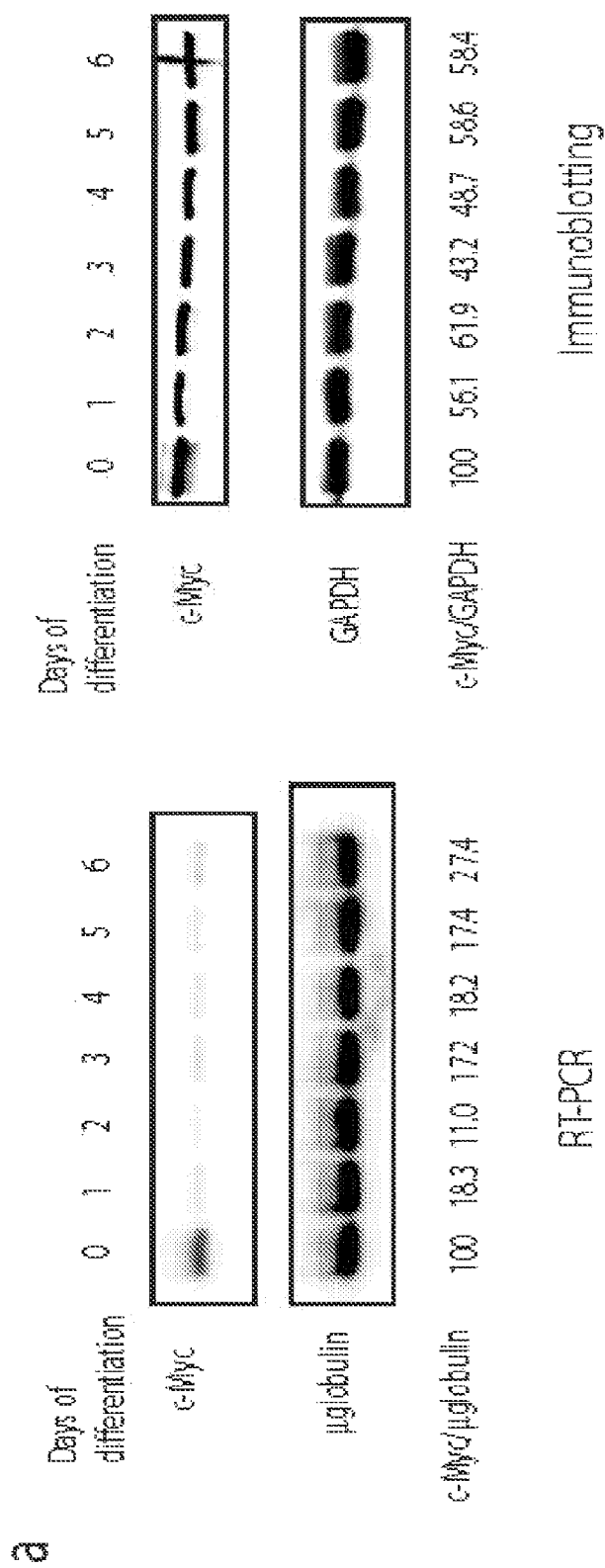
Figure 5B:
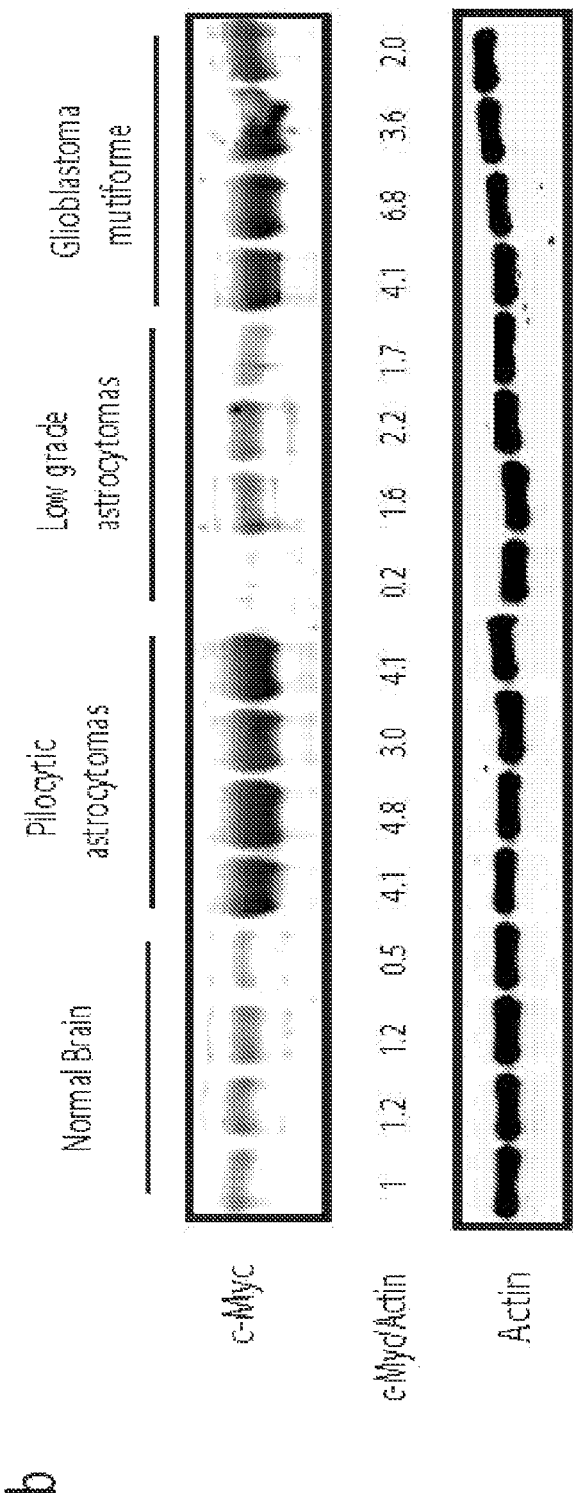

We next examined whether c-Myc levels correlate with high levels of PTB/A1/A2 proteins and PKM2 mRNA. We first examined C2C12 cells, and observed a rapid drop in c-Myc mRNA and protein preceding decreases in PTB and hnRNP A1 during differentiation (FIG. 5a). Importantly, we observed a strong correlation between elevated c-Myc protein levels, PTB/A1/A2 overexpression, and PKM2 upregulation in all but one of the twelve glioma samples analyzed above (FIG. 5b). c-Myc levels were highest in all the PA and GBM samples, which also showed the highest PKM2 levels. These results are consistent with the idea that c-Myc can function in PKM regulation by controlling expression of PTB/A1/A2.

To examine further for the possible role c-Myc in PTB/A1/A2 expression and PKM splicing regulation, we next asked whether decreasing c-Myc levels affected PTB/A1/A2 levels and the PKM1/PKM2 ratio. To this end, we transfected NIH-3T3 cells with vectors bearing a puromycin resistance marker that express either a c-Myc-targeting shRNA or a control shRNA. c-Myc shRNA-expressing cells were selected, as well as control shRNA-expressing colonies, and cultured in the presence of puromycin. Immunoblotting showed a reduction in c-Myc levels in cells stably transfected with c-Myc shRNA, compared to control cells (FIG. 5c). PTB/A1/A2 protein levels were also significantly reduced after depletion of c-Myc, in contrast with two other RNA processing factors not implicated in PKM splicing regulation, ASF/SF2 and CPSF73 (FIG. 5c). PTB/A1/A2 mRNA levels were also significantly reduced in the knockdown cells (FIG. 5d), supporting the idea that c-Myc regulates transcription of these genes. Importantly, the cells stably expressing the c-Myc shRNA showed a pronounced increase in the PKM1/2 ratio, expressing 33% PKM1 mRNA compared to 7% in the control (FIG. 5e). A separate line stably expressing a second c-Myc shRNA revealed a similarly elevated PKM1/2 ratio, as well as reduced levels of PTB/A1/A2, showing that the observed effects were not due to integration location or off target effects of the c-Myc shRNA (FIG. 17).

The above results demonstrate a role for c-Myc expression in maintaining high PTB/A1/A2 levels in NIH-3T3 cells. In contrast, similar experiments in HeLa cells revealed only a small decrease in PTB/A1/A2 levels, and no change in the PKM1/2 ratio (FIG. 18). This indicates that while NIH-3T3 cells are highly dependent on c-Myc for expression of PTB/A1/A2, HeLa cells are apparently less so, suggesting that additional factors might promote PTB/A1/A2 expression in these cells (see Discussion).

Figure 19A:
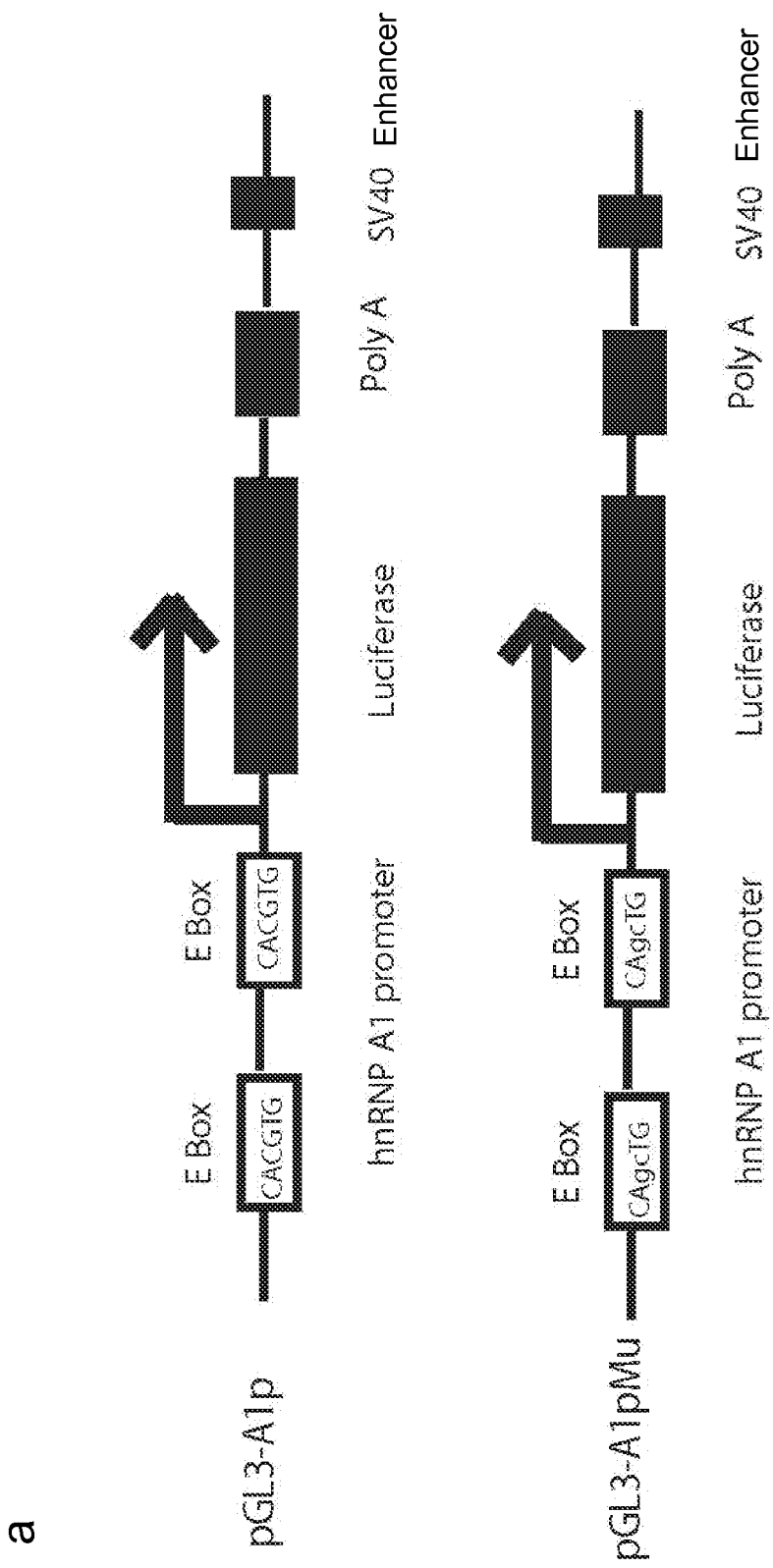
FIG. 19: c-Myc upregulates transcription from the hnRNP A1 promoter via E boxes. a, Diagrams showing hnRNP A1 promoter-Luciferase reporter constructs. E boxes (CACGTG) are putative c-Myc binding sites, which are located within a ~700 nt hnRNP A1 promoter region cloned upstream of the luciferase gene. pGL3-A1p contains the wild-type promoter region. pGL3-AlpMu contains mutated E boxes (indicated in the diagram). b, Results of dual luciferase reporter assays showing relative luciferase activity (top) activated by overexpression of c-Myc in HeLa cells by co-transfection of c-Myc expression vector and pGL3-A1p (lanes 1-3) or pGL3-AlpMu (lanes 4-6). Luciferase activity was normalized to Renilla luciferase activity, and pGL3-A1p activity was set as 1. Immunoblotting using c-Myc antibody to show c-Myc overexpression in transfected cells (bottom).
Figure 19:
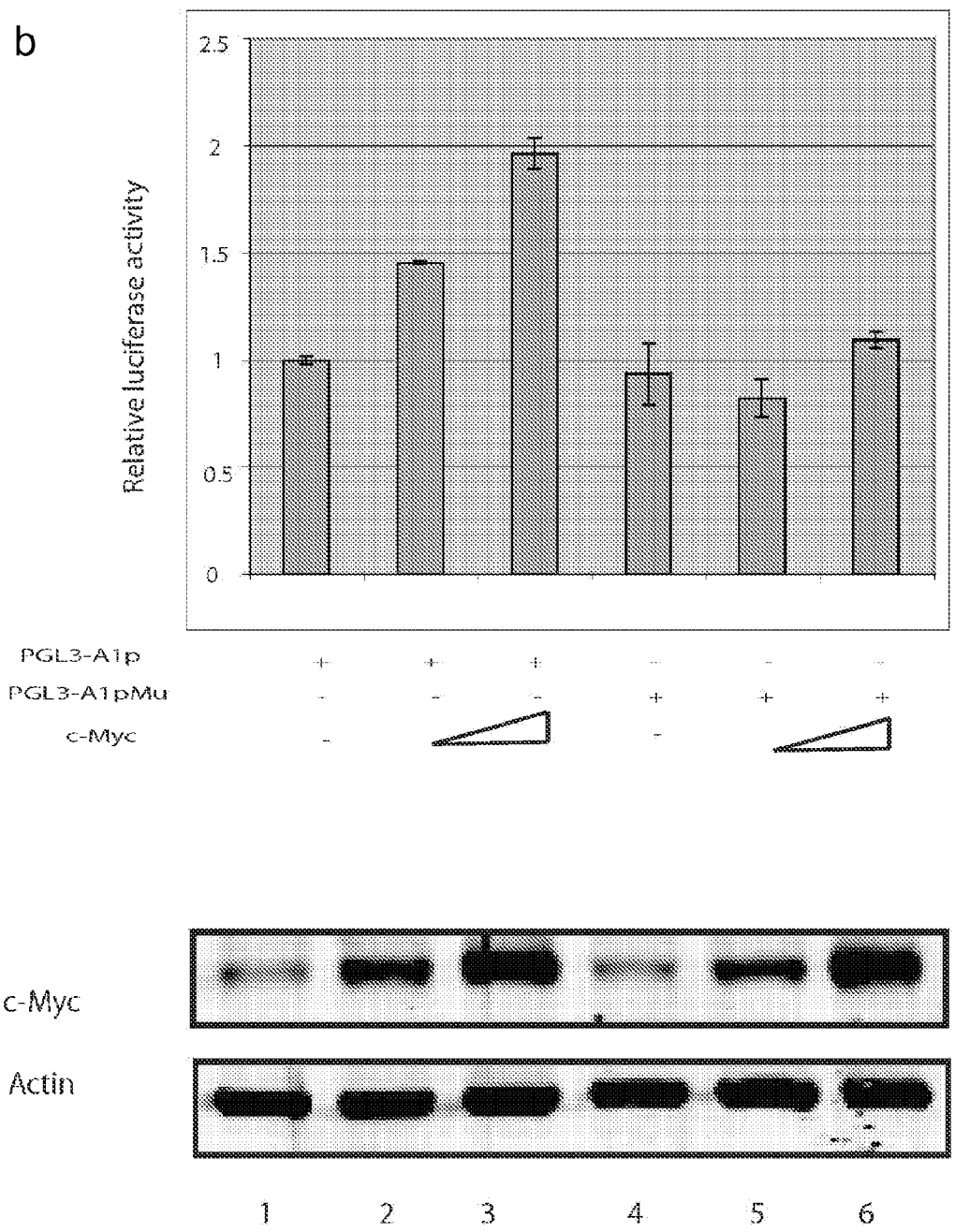

To examine directly whether c-Myc can upregulate transcription from the hnRNP A1 promoter, we cloned a portion of the A1 promoter containing the start site and the upstream ~700 base pairs into a luciferase reporter construct. Co-transfection of this construct and a c-Myc expression vector[40] into HeLa cells resulted in a dose-dependent increase, up to ~2-fold, in luciferase activity in comparison to co-transfection with an empty vector (FIG. 19). In contrast, an A1 promoter-luciferase vector in which the two canonical E-boxes were mutated did not respond significantly to c-Myc overexpression. These results provide evidence that c-Myc overexpression can in fact upregulate the hnRNP A1 promoter. Similar results were obtained with the PTB promoter.

Discussion

We have identified a pathway in which c-Myc upregulates three key hnRNP proteins that in turn alter splicing of PKM pre-mRNA to promote formation of PKM2 in growing cells.

Figure 6:
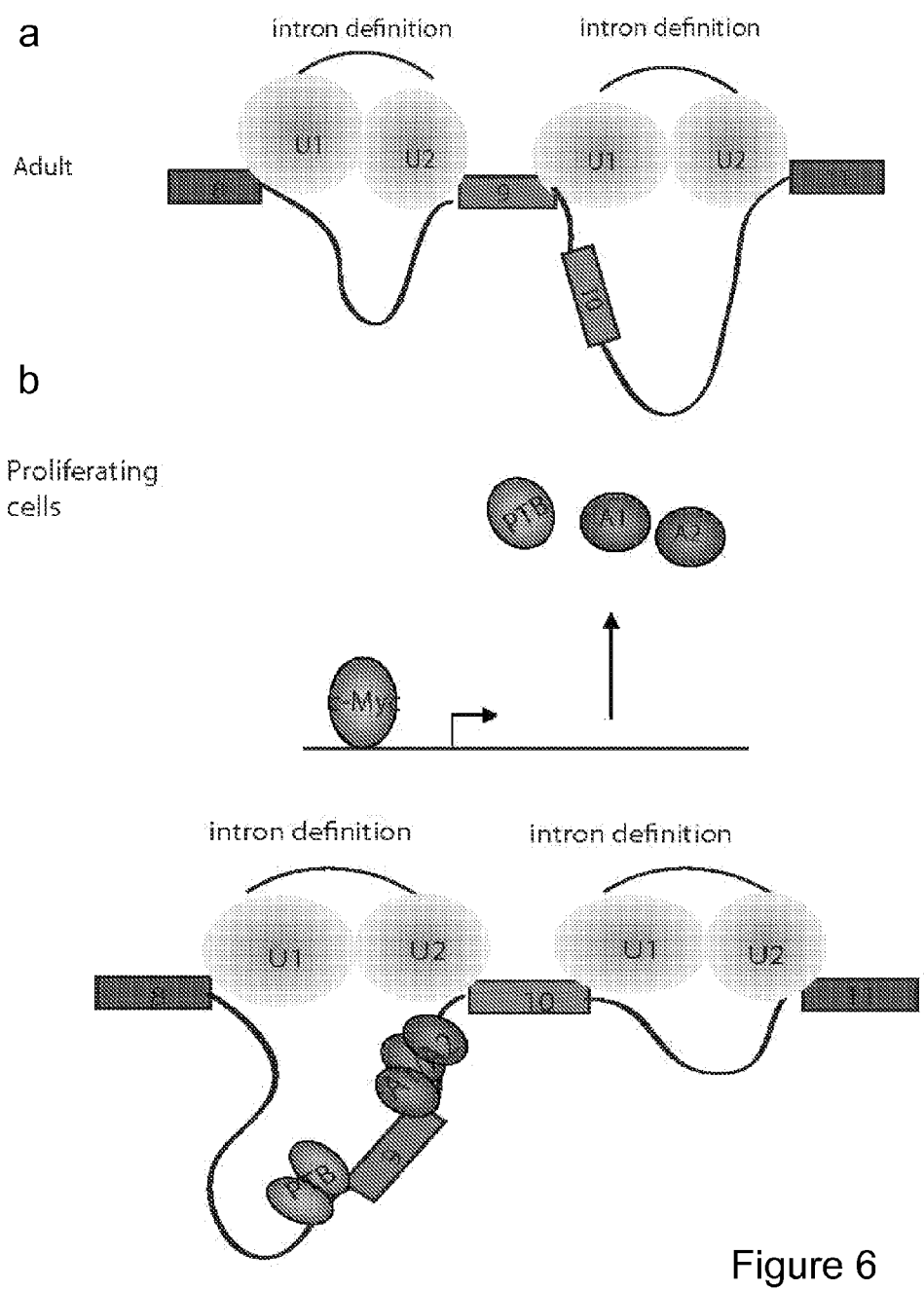
FIG. 6: A model for PKM splicing regulation a, In most adult tissues, low expression of PTB/A1/A2 allows for recognition of E9 by the splicing machinery and disrupts intronic structures favorable for E10 inclusion. b, In embryonic and cancer cells, PTB/A1/A2 are upregulated, bind to splicing signals flanking E9 and repress its inclusion. Binding of these proteins around E9 and possibly to other sites upstream of E10 creates an intronic structure favorable to E10 recognition and inclusion.

In addition, our results suggest a novel form of regulation of a mutually exclusive splicing event, in which three proteins (PTB/A1/A2) simultaneously act as repressors of one exon (E9) and activators of the other (E10) (FIG. 6). This mechanism is strongly supported by our experiments in which reduction in PTB/A1/A2 levels led to increased PKM1 mRNA levels and a concomitant decrease in PKM2 mRNA. While it is easy to envision how these proteins exclude E9, how might PTB/A1/A2 promote E10 inclusion? A variety of RNA binding proteins, including hnRNP A1/A2, have been shown to stimulate splicing of an adjacent exon through intronic binding sites[41]. While this phenomenon is currently poorly understood, one proposed mechanism for it is intron definition. In this model, regulatory protein binding to the adjacent intron leads to changes in intronic structure, which in turn makes the neighboring regulated exon more accessible to the splicing machinery, or facilitates cross-intron interactions[41]. PKM E10 is poorly recognized by the splicing machinery in the absence of adjacent intron definition, and such a structure is promoted by PTB/A1/A2 binding (FIG. 6). When PTB/A1/A2 proteins are downregulated, the splicing machinery assembles on E9 and the intronic structure required for E10 inclusion is eliminated, resulting in the default production of PKM1. While additional proteins capable of contributing to PKM splicing regulation are likely to be identified, our data indicate that PTB/A1/A2 expression levels are the primary determinant of PKM alternative splicing.

We have demonstrated a critical functional consequence for observations connecting PTB/A1/A2 upregulation with cell proliferation[42-44], various means of transformation[33,34], and a wide variety of cancers (e.g., refs. 45-47). Our results predict that the overexpression of these three proteins is a general phenomenon in cancer, a hypothesis supported by our observation that all GBMs and PAs exhibit overexpression of PTB/A1/A2.

Our finding that c-Myc coordinately upregulates PTB/A1/A2 provides an important mechanism for ensuring high levels of these proteins in cancer cells. PTB/A1/A2 upregulation by c-Myc is unlikely to be part of a widespread program of RNA-binding protein upregulation, as a compendium of genome wide studies to identify c-Myc targets identified only two other hnRNP proteins regulated by c-Myc[48]. As the small effect of c-Myc knockdown on PTB/A1/A2 in HeLa cells indicates, additional proliferation-associated transcription factors may also contribute to PTB/A1/A2 expression. For example, the transcription factor E2F1 was found to bind upstream of all three genes[34]. However, knockdown of E2F1, or of Rb, a negative regulator of E2F family transcription factors[49], resulted in little change in PTB/A1/A2 levels. Nonetheless, the broad overexpression of PTB/A1/A2 in cancer that we and others have observed suggests that their upregulation may in some instances be mediated by transcription factor(s) in addition to c-Myc.

PKM2 expression is robust, occurring in all growing cells we have examined, as well as the vast majority of tumors[7]. The fact that it is promoted by at least three proliferation-associated hnRNP proteins may contribute to the observed robustness. In support of this, we have shown that hnRNP A1/A2 are redundant for PKM2 expression in HeLa cells. While these proteins may be upregulated by pathways shared by all proliferating cells, lineage or other circumstances may affect the extent to which each is actually expressed. Placing PKM2 expression under the control of three proliferation-associated factors ensures that PKM2 switching occurs robustly when proliferation is required, a reflection of the importance of this event for cell growth.

Methods Summary

Plasmid constructs.

UV crosslinking substrates were cloned into pcDNA3 vector (Invitrogen). Mutations were introduced in EI9 by PCR-based site-directed mutagenesis[11]. c-Myc shRNA DNA sequences were purchased from Invitrogen and cloned into the pRS vector (Origene). hnRNP A1 promoter sequence was cloned into PGL3-enhancer vector (Promega).

UV crosslinking, RNA affinity purification, and immunoprecipitation assays.

UV crosslinking was performed as previously described[11]. The biotinylated RNA for the affinity purification was purchased from Dharmacon, and RNA affinity chromatography was carried out as previously described[11]. Immunoprecipitations were carried out using protein A-agarose beads (Roche).

RNA Interference.

RNAi was performed as described[11]. We transfected 50 pmol of hnRNP A1 siRNA and 25 pmol of other siRNA duplex in a 24-well plate. After 72 hours, we collected cells for RNA isolation and immunoblotting. Plasmids expressing c-Myc or control shRNA were transfected into 3T3 cells, and collected after 72 hours for RNA and protein analysis.

RT-PCR.

Total RNA was extracted from cells and tissue samples using Trizol (Invitrogen) according to manufacturer's instructions. RT was performed using an oligo-DT primer and 2.5-5 µg total RNA. 1 µl of the cDNA was used in PCR with [$^{32}$p]-dCTP. PstI, Tth111I, or EcoNI-digested products were resolved by 6% non-denaturing PAGE. qPCR for PTB/A1/A2 in control and c-Myc knockdown cells was performed with SYBR green from Fermentas using the Applied Biosystems 7300 real-time PCR system.

Cell Culture and Differentiation.

For differentiation treatment, C2C12 were plated on gelatin coated plates and allowed to reach confluence in DMEM (Invitrogen) supplemented with 20% fetal bovine serum (FBS) (Hyclone) at 37° C. in 5% $CO_2$, then switched to the same medium except with 2% donor horse serum (Hyclone) instead of FBS.

Human Brain Tumor Samples.

De-identified brain and glioma samples were obtained from the Bartoli Brain Tumor Bank at the Columbia University Medical Center. Samples were homogenized, and half of the homogenate was used for Trizol RNA extraction, the other half of each sample was processed for western blotting as described[50]. In all cases, immunoblots were scanned and quantified using the LI-COR Odyssey system.

Dual Luciferase Reporter (DLR) Assay.

c-Myc expression vector and hnRNP A1 promoter vector were co-transfected into HeLa cells. 24 hours after transfection, cells were collected and DLR assays were preformed using Dual Luciferase Reporter Assay System (Promega) following product protocol.

REFERENCES

1. Warburg, O. On the origin of cancer cells. *Science* 123, 309-14 (1956).
2. Wang, T., Marquardt, C. & Foker, J. Aerobic glycolysis during lymphocyte proliferation. *Nature* 261, 702-5 (1976).
3. Fantin, V. R., St-Pierre, J. & Leder, P. Attenuation of LDH-A expression uncovers a link between glycolysis, mitochondrial physiology, and tumor maintenance. *Cancer Cell* 9, 425-34 (2006).
4. Christofk, H. R. et al. The M2 splice isoform of pyruvate kinase is important for cancer metabolism and tumour growth. *Nature* 452, 230-3 (2008).
5. Vander Heiden, M. G., Cantley, L. C. & Thompson, C. B. Understanding the Warburg effect: the metabolic requirements of cell proliferation. *Science* 324, 1029-33 (2009).
6. Christofk, H. R., Vander Heiden, M. G., Wu, N., Asara, J. M. & Cantley, L. C. Pyruvate kinase M2 is a phosphotyrosine-binding protein. *Nature* 452, 181-6 (2008).
7. Mazurek, S., Boschek, C. B., Hugo, F. & Eigenbrodt, E. Pyruvate kinase type M2 and its role in tumor growth and spreading. *Semin Cancer Biol* 15, 300-8 (2005).
8. Marjanovic, S., Eriksson, I. & Nelson, B. D. Expression of a new set of glycolytic isozymes in activated human peripheral lymphocytes. *Biochim Biophys Acta* 1087, 1-6 (1990).
9. Wang, E. T. et al. Alternative isoform regulation in human tissue transcriptomes. *Nature* 456, 470-6 (2008).
10. Takenaka, M. et al. Alternative splicing of the pyruvate kinase M gene in a minigene system. *Eur J Biochem* 235, 366-71 (1996).
11. Kashima, T., Rao, N., David, C. J. & Manley, J. L. hnRNP A1 functions with specificity in repression of SMN2 exon 7 splicing. *Hum Mol Genet.* 16, 3149-59 (2007).
12. Del Gatto-Konczak, F., Olive, M., Gesnel, M. C. & Breathnach, R. hnRNP A1 recruited to an exon in vivo can function as an exon splicing silencer. *Mol Cell Biol* 19, 251-60 (1999).
13. Burd, C. G. & Dreyfuss, G. RNA binding specificity of hnRNP A1: significance of hnRNP A1 high-affinity binding sites in pre-mRNA splicing. *EMBO J.* 13, 1197-204 (1994).
14. Spellman, R. et al. Regulation of alternative splicing by PTB and associated factors. *Biochem Soc Trans* 33, 457-60 (2005).
15. Castle, J. C. et al. Expression of 24,426 human alternative splicing events and predicted cis regulation in 48 tissues and cell lines. *Nat Genet.* 40, 1416-25 (2008).
16. Yamada, K. & Noguchi, T. Nutrient and hormonal regulation of pyruvate kinase gene expression. *Biochem J* 337 (Pt 1), 1-11 (1999).
17. Holcik, M. & Liebhaber, S. A. Four highly stable eukaryotic mRNAs assemble 3' untranslated region RNA-protein complexes sharing cis and trans components. *Proc Natl Acad Sci USA* 94, 2410-4 (1997).
18. Evans, J. R. et al. Members of the poly (rC) binding protein family stimulate the activity of the c-myc internal ribosome entry segment in vitro and in vivo. *Oncogene* 22, 8012-20 (2003).
19. Moumen, A., Masterson, P., O'Connor, M. J. & Jackson, S. P. hnRNP K: an HDM2 target and transcriptional coactivator of p53 in response to DNA damage. *Cell* 123, 1065-78 (2005).
20. Michaud, S. & Reed, R. A functional association between the 5' and 3' splice site is established in the earliest prespliceosome complex (E) in mammals. *Genes Dev* 7, 1008-20 (1993).
21. Marinescu, V., Loomis, P. A., Ehmann, S., Beales, M. & Potashkin, J. A. Regulation of retention of FosB intron 4 by PTB. *PLoS ONE* 2, e828 (2007).
22. Pomeranz Krummel, D. A., Oubridge, C., Leung, A. K., Li, J. & Nagai, K. Crystal structure of human spliceosomal U1 snRNP at 5.5 A resolution. *Nature* 458, 475-80 (2009).
23. Karni, R. et al. The gene encoding the splicing factor SF2/ASF is a proto-oncogene. *Nat Struct Mot Biol* 14, 185-93 (2007).

24. Jumaa, H., Guenet, J. L. & Nielsen, P. J. Regulated expression and RNA processing of transcripts from the Srp20 splicing factor gene during the cell cycle. *Mol Cell Biol* 17, 3116-24 (1997).
25. Harada, Y., Nakamura, M. & Asano, A. Temporally distinctive changes of alternative splicing patterns during myogenic differentiation of C2C12 cells. *J Biochem* 118, 780-90 (1995).
26. Boutz, P. L., Chawla, G., Stoilov, P. & Black, D. L. MicroRNAs regulate the expression of the alternative splicing factor nPTB during muscle development. *Genes Dev* 21, 71-84 (2007).
27. Furnari, F. B. et al. Malignant astrocytic glioma: genetics, biology, and paths to treatment. *Genes Dev* 21, 2683-710 (2007).
28. Fulham, M. J., Melisi, J. W., Nishimiya, J., Dwyer, A. J. & Di Chiro, G. Neuroimaging of juvenile pilocytic astrocytomas: an enigma. *Radiology* 189, 221-5 (1993).
29. Watermann, D. O. et al. Splicing factor Tra2-beta1 is specifically induced in breast cancer and regulates alternative splicing of the CD44 gene. *Cancer Res* 66, 4774-80 (2006).
30. Carpenter, B. et al. Heterogeneous nuclear ribonucleoprotein K is over expressed, aberrantly localised and is associated with poor prognosis in colorectal cancer. *Br J Cancer* 95, 921-7 (2006).
31. Zheng, H. et al. p53 and Pten control neural and glioma stem/progenitor cell renewal and differentiation. *Nature* 455, 1129-33 (2008).
32. Birney, E. et al. Identification and analysis of functional elements in 1% of the human genome by the ENCODE pilot project. *Nature* 447, 799-816 (2007).
33. Kidder, B. L. et al. Embryonic stem cells contribute to mouse chimeras in the absence of detectable cell fusion. *Cloning Stem Cells* 10, 231-48 (2008).
34. Chen, X. et al. Integration of external signaling pathways with the core transcriptional network in embryonic stem cells. *Cell* 133, 1106-17 (2008).
35. Eilers, M. & Eisenman, R. N. Myc's broad reach. *Genes Dev* 22, 2755-66 (2008).
36. Shiio, Y. et al. Quantitative proteomic analysis of Myc oncoprotein function. *EMBO J* 21, 5088-96 (2002).
37. Schlosser, I. et al. Dissection of transcriptional programmes in response to serum and c-Myc in a human B-cell line. *Oncogene* 24, 520-4 (2005).
38. O'Connell, B. C. et al. A large scale genetic analysis of c-Myc-regulated gene expression patterns. *J Biol Chem* 278, 12563-73 (2003).
39. Shim, H. et al. c-Myc transactivation of LDH-A: implications for tumor metabolism and growth. *Proc Natl Acad Sci USA* 94, 6658-63 (1997).
40. Wu, K. J., Mattioli, M., Morse, H. C., 3rd & Dalla-Favera, R. c-MYC activates protein kinase A (PKA) by direct transcriptional activation of the PKA catalytic subunit beta (PKA-Cbeta) gene. *Oncogene* 21, 7872-82 (2002).
41. Martinez-Contreras, R. et al. Intronic binding sites for hnRNP A/B and hnRNP F/H proteins stimulate pre-mRNA splicing. *PLoS Biol* 4, e21 (2006).
42. He, Y., Brown, M. A., Rothnagel, J. A., Saunders, N. A. & Smith, R. Roles of heterogeneous nuclear ribonucleoproteins A and B in cell proliferation. *J Cell Sci* 118, 3173-83 (2005).
43. Planck, S. R., Listerud, M. D. & Buckley, S. D. Modulation of hnRNP A1 protein gene expression by epidermal growth factor in Rat-1 cells. *Nucleic Acids Res* 16, 11663-73 (1988).
44. Biamonti, G. et al. Human hnRNP protein A1 gene expression. Structural and functional characterization of the promoter. *J Mol Biol* 230, 77-89 (1993).
45. He, X. et al. Knockdown of polypyrimidine tract-binding protein suppresses ovarian tumor cell growth and invasiveness in vitro. *Oncogene* 26, 4961-8 (2007).
46. Zerbe, L. K. et al. Relative amounts of antagonistic splicing factors, hnRNP A1 and ASF/SF2, change during neoplastic lung growth: implications for pre-mRNA processing. *Mol Carcinog* 41, 187-96 (2004).
47. Zhou, J. et al. Differential expression of the early lung cancer detection marker, heterogeneous nuclear ribonucleoprotein-A2/B1 (hnRNP-A2/B1) in normal breast and neoplastic breast cancer. *Breast Cancer Res Treat* 66, 217-24 (2001).
48. Zeller, K. I., Jegga, A. G., Aronow, B. J., O'Donnell, K. A. & Dang, C. V. An integrated database of genes responsive to the Myc oncogenic transcription factor: identification of direct genomic targets. *Genome Biol* 4, R69 (2003).
49. Giacinti, C. & Giordano, A. RB and cell cycle progression. *Oncogene* 25, 5220-7 (2006).
50. Jin, W., McCutcheon, I. E., Fuller, G. N., Huang, E. S. & Cote, G. J. Fibroblast growth factor receptor-1 alpha-exon exclusion and polypyrimidine tract-binding protein in glioblastoma multiforme tumors. *Cancer Res* 60, 1221-4 (2000).

Additional Methods

Plasmid Constructs.

Long UV crosslinking substrates (EI9, EI10, I8E9 and I9E10) were prepared by amplifying fragments from HeLa genomic DNA using Pfu turbo (Stratagene), and cloning the products into pcDNA3 (Invitrogen). EI9(1-20), EI9(21-49), and EI9(50-68, 18, I8mu, and I9 DNA sequences were ordered from Invitrogen and cloned into pcDNA3. Primers used to amplify genomic DNA fragments were: EI9 forward, CGC GGA TCC TTC TTA TAA GTG TTT AGC AGC AGC T (SEQ ID NO: 1), reverse, CGG AAT TCA CTG AGC CAC AGG ACC CTT TG (SEQ ID NO: 2); EI10 forward, CGC GGA TCC CTC CTT CAA GTG CTG CAG TG (SEQ ID NO: 3), reverse, CGG AAT CCT GGG CCC AGG GAA GGG G (SEQ ID NO: 4); I8E9 forward, CCC AAG CTT AAA TTC CCC ATT CTG TCT TCC CAT G (SEQ ID NO: 5), reverse, CGG GAT CCC TGC CAG ACT CCG TCA GAA CT (SEQ ID NO: 6); I9E10 forward, CCC AAG CTT CTG TCC GGT GAC TCT TCC CC (SEQ ID NO: 7), reverse, CGG GAT CCC TGC CAG ACT TGG TGA GGA CG (SEQ ID NO: 8). Mutations were introduced in EI9 by PCR-based site-directed mutagenesis[11]. Mouse c-Myc and control shRNA DNA sequences were ordered from Invitrogen and cloned into pRS vector (Origene) with BamH I and Hind III. The hnRNP A1 promoter region, either wild-type or the E box mutant, was cloned into PGL3-enhancer vector (Promega).

Antibodies.

The following antibodies were used in this study: BB7 for human PTB IP, 3H8 for mouse/human PTB immunoblots (Sigma), MC3 for U2AF65 (Sigma), α-HA (Covance) DP3D3 for hnRNP A2 (Abcam), N-262 for c-Myc (Santa Cruz), α-Actin (Sigma), α-GAPDH (Sigma), 9H10 for hnRNP A1 (Sigma), mAb104 for SRp20.

UV Crosslinking, RNA Affinity Purification, and Immunoprecipitation Assays.

We carried out ultraviolet crosslinking as previously described[11]. Briefly, we linearized the UV crosslinking plasmids with an appropriate restriction enzyme and synthesized the RNAs with [$^{32}$p]-UTP or [$^{32}$p]-CTP. We incubated 1×10$^5$ c.p.m. RNAs with 10 μg HeLa or C2C12 NE in buffer D in a 20 μl reaction at 30° C. for 15 minutes, then irradiated the samples with ultraviolet light in a Stratalinker 1800 (Stratagene), digested them with RNase A (10 μg ml$^{-1}$) and resolved them by SDS-PAGE. The RNA affinity pull-down experiment and immunoprecipitation was preformed as described[11]. The 5' biotinylated EI9(50-68) and I8 RNA oligonucleotides were purchased from Dharmacon. Antibodies were bound to protein A-agarose beads prior to IP. We used the following antibodies for IP: BB7 for PTB, and MC3 for U2AF65.

RNA Interference.

We carried out RNA interference of PTB and hnRNP A1/A2 as described[11]. Briefly, we plated HeLa, 293, MCF-7, or U87 cells at 2.5-3×10$^4$ cells per well in 24-well plates. The next day, we mixed 50 pmole of hnRNP A1 duplex RNA and 25 pmole of the other duplex RNAs with 1.5 μl lipofectamine 2000 transfection reagent (Invitrogen) plus 100 μl of Opt-MEM medium and added this to cells after RNA duplex-lipid complex formation. For double and triple knockdowns in HeLa and 293 cells, RNA duplexes were transfected simultaneously. The control RNA duplex was used to ensure that parallel experiments had equal amounts of RNA. In MCF-7 and U87 cells, the second and third RNA duplexes were transfected 6 hours after the previous transfection. 72 hours after transfection, we collected cells for RNA isolation and immunoblotting. We used the following siRNAs (Dharmacon; the sense strand sequences are given): human hnRNP A1, CAGCUGAGGAAGCUCUUCA (SEQ ID NO: 9); human hnRNP A2, GGAACAGUUCCGUAAGCUC (SEQ ID NO: 10); human PTB, GCCUCAACGUCAAGUACAA (SEQ ID NO: 11). ASF/SF2 depletion was performed as previously described[11].

c-Myc shRNA Stable Cell Lines.

Stable cell lines expressing c-Myc shRNAs or control shRNA were obtained by transfecting pRS-shRNA vectors into NIH3T3 cells followed by drug selection. Cells were plated in 10 cm plates. The next day, transfected cells were diluted and medium was replaced with medium containing a final concentration 3 μg/mlpuromycin. After 7-10 days, a mixture of fast- and slow-growing colonies appeared in cells transfected with c-Myc shRNA, while only fast-growing colonies appeared in cells transfected with control shRNA. Single slow-growing colonies were isolated and cultured for c-Myc expressing cells. c-Myc expression was examined by immunoblotting. Positive colonies were collected for RT-PCR and western blotting. The following sense shRNA sequences were used: control, gat ccG AGG CTT CTT ATA AGT GTT TAC TCG AGT AAA CAC TTA TAA GAA GCC TCT TTT Ta (SEQ ID NO: 12); Mouse c-Myc shRNA1, gat ccC ATC CTA TGT TGC GGT CGC TAC TCG AGT AGC GAC CGC AAC ATA GGA TGT TTT Ta (SEQ ID NO: 13); Mouse c-Myc shRNA2, gat ccC GGA CAC ACA ACG TCT TGG AAC TCG AGT TCC AAG ACG TTG TGT GTC CGT TTT Ta (SEQ ID NO: 14); human c-Myc shRNA, gat ccC CAT AAT GTA AAC TGC CTC AAC TCG AGT TGA GGC AGT TTA CAT TAT GGT TTT Ta (SEQ ID NO: 15).

RT-PCR.

Total RNA was extracted from tissue culture and human brain tumor samples using Trizol (Invitrogen) according to the manufacturer's instructions. Total RNA (2.5-5 μg) was used for each sample in a 20 μl reaction with 0.5 μL of SuperScript III RT (Invitrogen). 1 μl of the cDNA library was used in a 50 μl PCR reaction containing 3 μCi [$^{32}$p]-dCTP. 10 μl of the PCR products were digested by Pst I and Tth111 I (human PKM) or EcoN I (mouse PKM) and the products were resolved by 6% non-denaturing PAGE. Primers used in the PCR reactions were: human PKM exon8 forward, CTG AAG GCA GTG ATG TGG CC (SEQ ID NO: 16); human PKM exon11 reverse, ACC CGG AGG TCC ACG TCC TC (SEQ ID NO: 17); mouse PKM exon8 forward, CAA GGG GAC TAC CCT CTG G (SEQ ID NO: 18); mouse PKM exon11 reverse, ACA CGA AGG TCG ACA TCC TC (SEQ ID NO: 19), human μglobulin: forward, GGC TAT CCA GCG TAC TCC AAA (SEQ ID NO: 20), reverse, CGG CAG GCA TAC TCA TCT TTT T (SEQ ID NO: 21); mouse μglobulin: forward, TTC TGG TGC TTG TCT CAC TGA (SEQ ID NO: 22), reverse, CAG TAT GTT CGG CTT CCC ATT C (SEQ ID NO: 23). qRT-PCR was performed using the following primers: mouse hnRNP A1: forward, TGG AAG CAA TTT TGG AGG TGG (SEQ ID NO: 24), reverse, GGT TCC GTG GTT TAG CAA AGT (SEQ ID NO: 25); mouse hnRNP A2: forward, AAG AAA TGC AGG AAG TCC AAA GT (SEQ ID NO: 26), reverse, CTC CTC CAT AAC CAG GGC TAC (SEQ ID NO: 27); mouse PTB: forward, AGC AGA GAC TAC ACT CGA CCT (SEQ ID NO: 28), reverse, GCT CCT GCA TAC GGA GAG G (SEQ ID NO: 29); mouse RPL13A forward, GGG CAG GTT CTG GTA TTG GAT (SEQ ID NO: 30), reverse, GGC TCG GAA ATG GTA GGG G (SEQ ID NO: 31). Relative amounts of mRNA were calculated using the comparative Ct method.

Cell Culture and Differentiation.

C2C12 cells were grown in DMEM (Invitrogen) supplemented with 20% fetal bovine serum (FBS) (Hyclone) at 37° C. in 5% CO$_2$. For differentiation treatment, C2C12 were plated on gelatin coated plates, allowed to reach confluence, and then switched to DMEM 2% donor equine serum (Hyclone). HeLa and 293 cells were grown in DMEM, 10% FBS. NIH3T3 cells were grown in DMEM, 10% bovine calf serum (BCS) (Hyclone).

Human Brain Tumor Samples.

De-identified brain and glioma samples were obtained from the Bartoli Brain Tumor Bank at the Columbia University Medical Center. Non-cancerous samples removed from epileptic patients were used for normal brain. Approximately 25-200 mg of each sample was obtained. Half of the homogenate was used for Trizol RNA extraction, the other half of each sample was processed for immunoblotting as described[50].

Dual Luciferase Reporter (DLR) Assay.

c-Myc expression vector and hnRNP A1 promoter vector were co-transfected into HeLa cells. 24 hours after transfection, cells were collected and DLR assays were preformed using Dual Luciferase Reporter Assay System (Promega) following product protocol.

Example 2

HnRNP proteins controlled by c-Myc deregulate pyruvate kinase mRNA splicing in cancer. David et al. (2009) Nature 463, 364-368 (21 Jan. 2010)|doi:10.1038/nature08697; Published online 13 Dec. 2009.

When oxygen is abundant, quiescent cells efficiently extract energy from glucose primarily by oxidative phosphorylation, while under the same conditions tumor cells consume glucose more avidly, converting it to lactate. This long-observed phenomenon is known as aerobic glycolysis[1], and is now understood to be important for cell growth[2,3]. Because aerobic glycolysis is only useful to growing cells, it is tightly regulated in a proliferation-linked manner[4], in part through control of pyruvate kinase (PK) isoform expression. The embryonic isoform, PKM2, is almost universally re-expressed in cancer, and promotes aerobic glycolysis, while the adult isoform, PKM1, promotes oxidative phosphorylation[2].

These two isoforms result from mutually exclusive alternative splicing of the PKM pre-mRNA, reflecting inclusion of either exon 9 (PKM1) or exon 10 (PKM2). Here we show that three hnRNP proteins, PTB, hnRNPA1 and hnRNPA2, bind repressively to sequences flanking exon 9, resulting in exon 10 inclusion. We also demonstrate that the oncogenic transcription factor c-Myc upregulates transcription of PTB/A1/A2, ensuring a high PKM2:PKM1 ratio. Establishing a relevance to cancer, we show that gliomas overexpress c-Myc and PTB/A1/A2 in a manner that correlates with PKM2 expression. Our results thus define a pathway that regulates an alternative splicing event required for tumor cell proliferation.

Alternative splicing of PKM plays an important role in determining the metabolic phenotype of mammalian cells. The single exon difference imparts the enzymes produced with important functional distinctions. For example, PKM2, but not PKM1 is regulated by the binding of tyrosine phosphorylated peptides, which results in release of the allosteric activator fructose 1-6 bisphosphate and inhibition of PK activity[5], a property that might allow growth-factor initiated signaling cascades to channel glycolytic intermediates into biosynthetic processes. The importance of tumor reversion to PKM2 was underscored by experiments in which replacement of PKM2 with PKM1 in tumor cells resulted in markedly reduced growth[2]. Consistent with a critical role in proliferation, re-expression of PKM2 in tumors is robust, although little is known about the regulation of this process.

Figure 20:
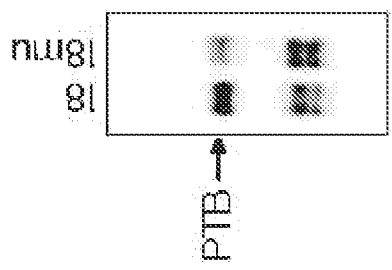
FIG. 20: hnRNP proteins bind specifically to sequences flanking E9. a, Schematic diagram of PKM splicing. b, Position of probes spanning the E9 or E10 5' splice sites (top). After UV crosslinking, proteins were detected by autoradiography (bottom). c, Affinity chromatography using EI9(50-68). Bound proteins were separated by SDS-PAGE and Coomassie stained. Bands excised for mass spectrometry are indicated. d, Sequence of EI9(50-68), putative hnRNPA1/A2 binding site indicated in bold italics (top). UV crosslinking with wild-type RNA, or RNA with a mutation in the putative hnRNPA1/A2 binding site (bottom). e, Position of I8 and I9 (top). UV crosslinking using I8 or I9 substrates (bottom left). UV crosslinking reactions were IPed with either α-PTB (BB7) or α-HA antibodies (bottom right). f, UV crosslinking with I8 and mutant derivative I8mu, sequences indicated above. Putative PTB binding sites in I8 are underlined.
Figure 24:
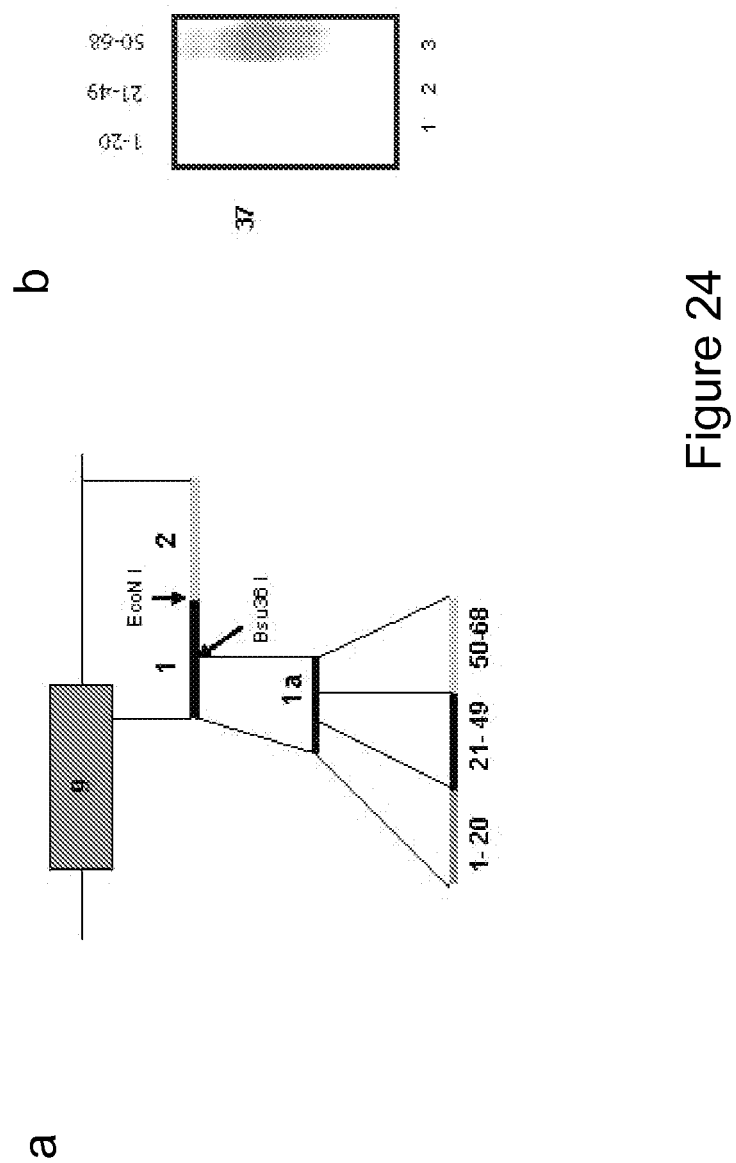
FIGS. 24 a-b: Mapping of strong ~35-40 kDa crosslinking in the EI9 substrate. Truncations in EI9 were introduced with the indicated restriction enzymes (left). Strong crosslinking mapped to EI(1a). Sections of EI9(1a) were cloned and used for UV crosslinking in HeLaNE.
Figure 25:
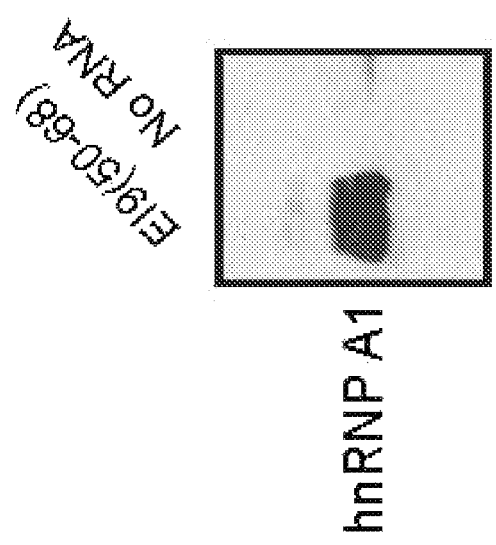
FIG. 25: hNRNP A1 binds to EI9(50-68). After RNA affinity chromatography using biotinylated EI9(50-68), protein samples from EI9(50-68) (lane 1) and no RNA control (lane 2) were separated on 10% SDS-PAGE and analyzed by immunoblotting using an anti-hnRNP A1 antibody.

We set out to identify RNA binding proteins that might regulate PKM alternative splicing. To this end, we prepared an [$\alpha$-$^{32}$P]-UTP labeled 250 nucleotide (nt) RNA spanning the E9 5' splice site (EI9), previously identified as inhibitory to E9 inclusion[6], as well as a labeled RNA from a corresponding region of E10 (EI10) (FIG. 20b), and performed ultraviolet (UV) crosslinking assays with HeLa nuclear extracts (NE)[7]. After separation by SDS-PAGE, multiple proteins from 35-40 kDa appeared using the EI9 substrate, while little binding was observed using the EI10 substrate (FIG. 20b). Strong binding was mapped to a 19 nt region we named EI9(50-68) that spans the E9 5' splice site (FIGS. 24 a-b). To identify the bound proteins, we performed RNA affinity chromatography using a 5' biotin-labeled RNA corresponding to EI9(50-68). After SDS-PAGE and Coomassie staining, the pattern of specifically bound proteins closely matched that observed after UV crosslinking (FIG. 20c). The four indicated proteins between 35-40 kDa were excised, and identified by mass spectrometry as isoforms of hnRNPA1 and hnRNPA2, RNA binding proteins with well established roles as sequence-specific repressors of splicing (e.g., refs. 7, 8). This result was confirmed by immunoblotting with antibodies against hnRNPA1 (FIG. 25).

Figure 26:
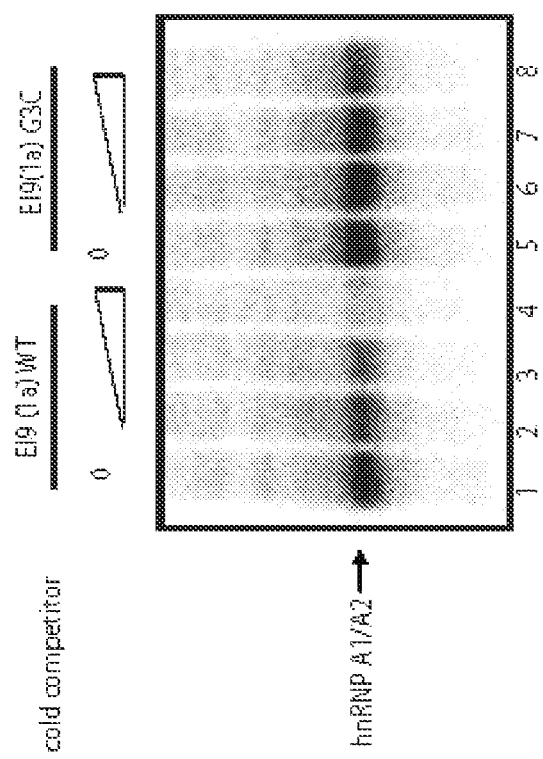
FIG. 26: hNRNP A1 binding to EI9(1a) is specifically decreased by G3C mutation. $^{32}$P-UTP labeled EI9(1a) RNA (see diagram in FIGS. 24 *a-b*) was incubated with HeLaNE, in the presence of increasing amount (0, 1.5, 3, 7.5 μM) of cold WT EI9(1a) RNA (lanes 1-4) or cold EI9(1a) G3C mutant RNA (lanes 5-8), followed by UV crosslinking.
Figure 27:
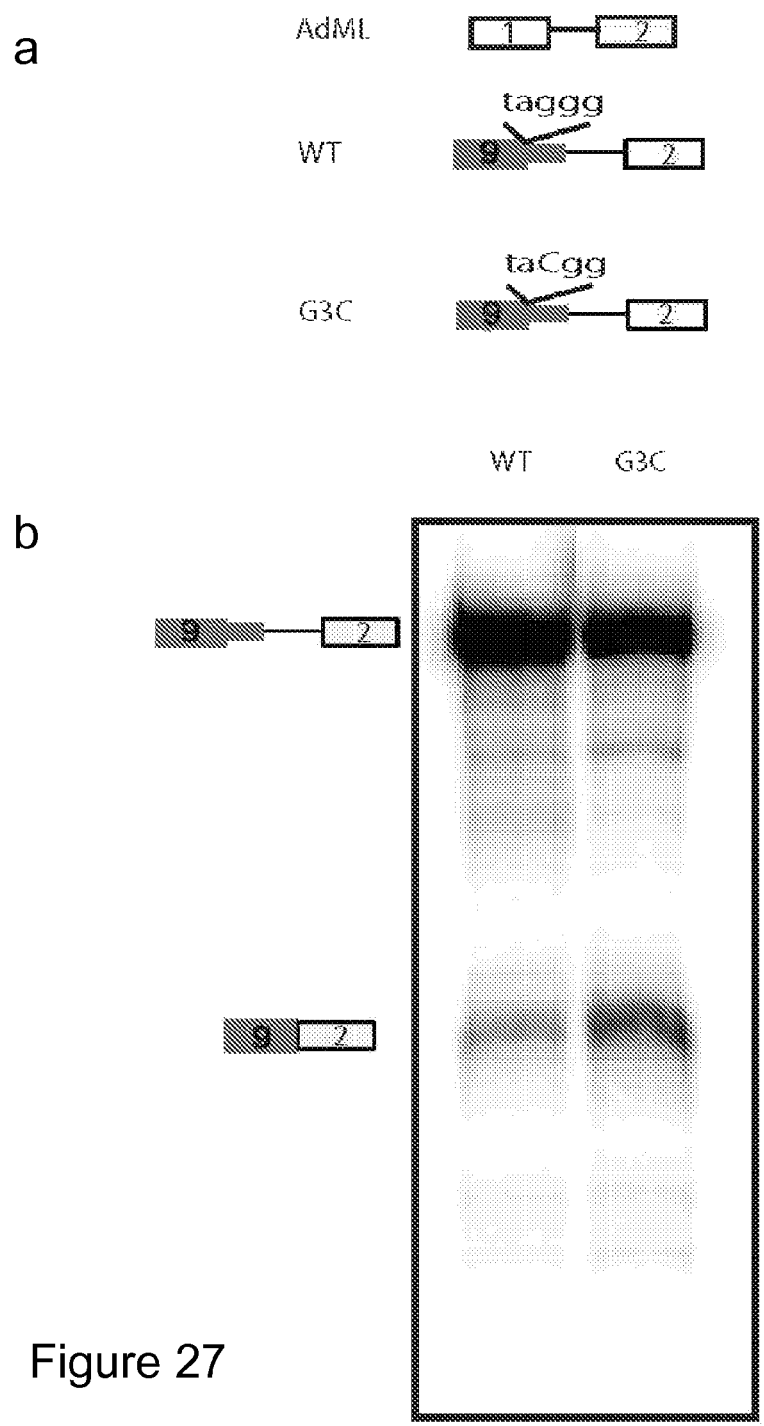
FIGS. 27 *a-b*: Mutation of hnRNPA1/A2 binding site increases splicing of E9 containing in vitro splicing substrate. Schematic diagram of in vitro splicing constructs derived from AdML pre-mRNA substrate (FIG. 27*a*). In vitro splicing in HeLa nuclear extract using WT or G3C substrates.
Figure 28:
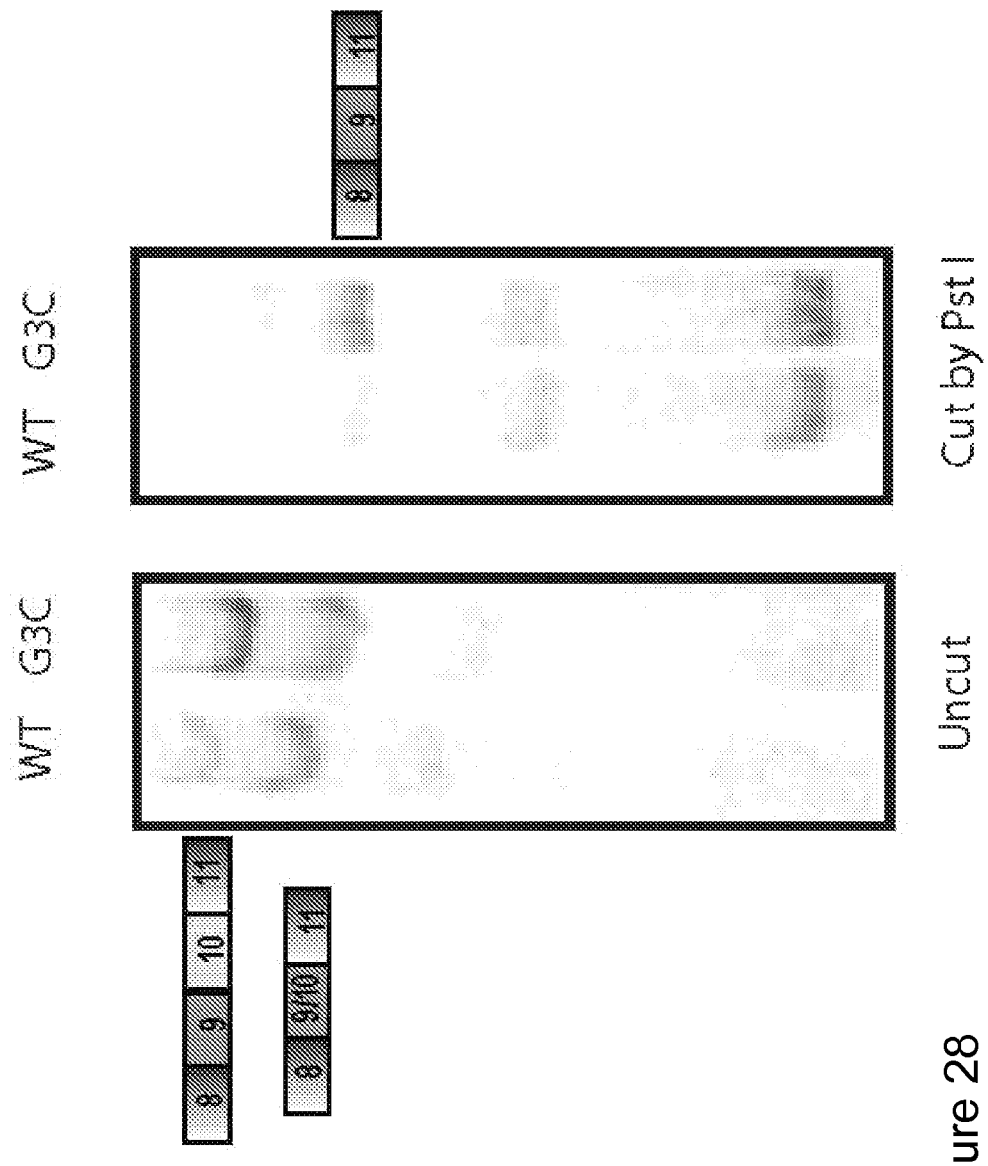
FIG. 28: Minigene with mutated hnRNPA1/A2 binding site increases inclusion of E9 in HeLa cells. The mutation results in an increase in E9 and E10 double inclusion (left panel). Single inclusion band at left G3C lane contains a higher proportion of E9 containing transcripts as determined by Pst I digestion (right panel).

The sequence immediately downstream of the E9 5' splice site contains a UAGGGC sequence that is highly related to the consensus hnRNPA1 high affinity binding site identified by SELEX, UAGGG(A/U)[9] (FIG. 20d). Consistent with previous mutational studies of an identical A1 binding site[8], mutation of the G3 nucleotide of this motif to C led to a large decrease in hnRNPA1/A2 binding (FIG. 20d; FIG. 26). The G3C mutation resulted in increased splicing in vitro when introduced into a splicing substrate containing E9 (FIGS. 27 a-b), and led to increased E9 inclusion in a minigene construct in vivo (FIG. 28). These data confirm the presence of an inhibitory hnRNPA1/A2 binding site immediately downstream of the E9 5' splice site.

Figure 29:
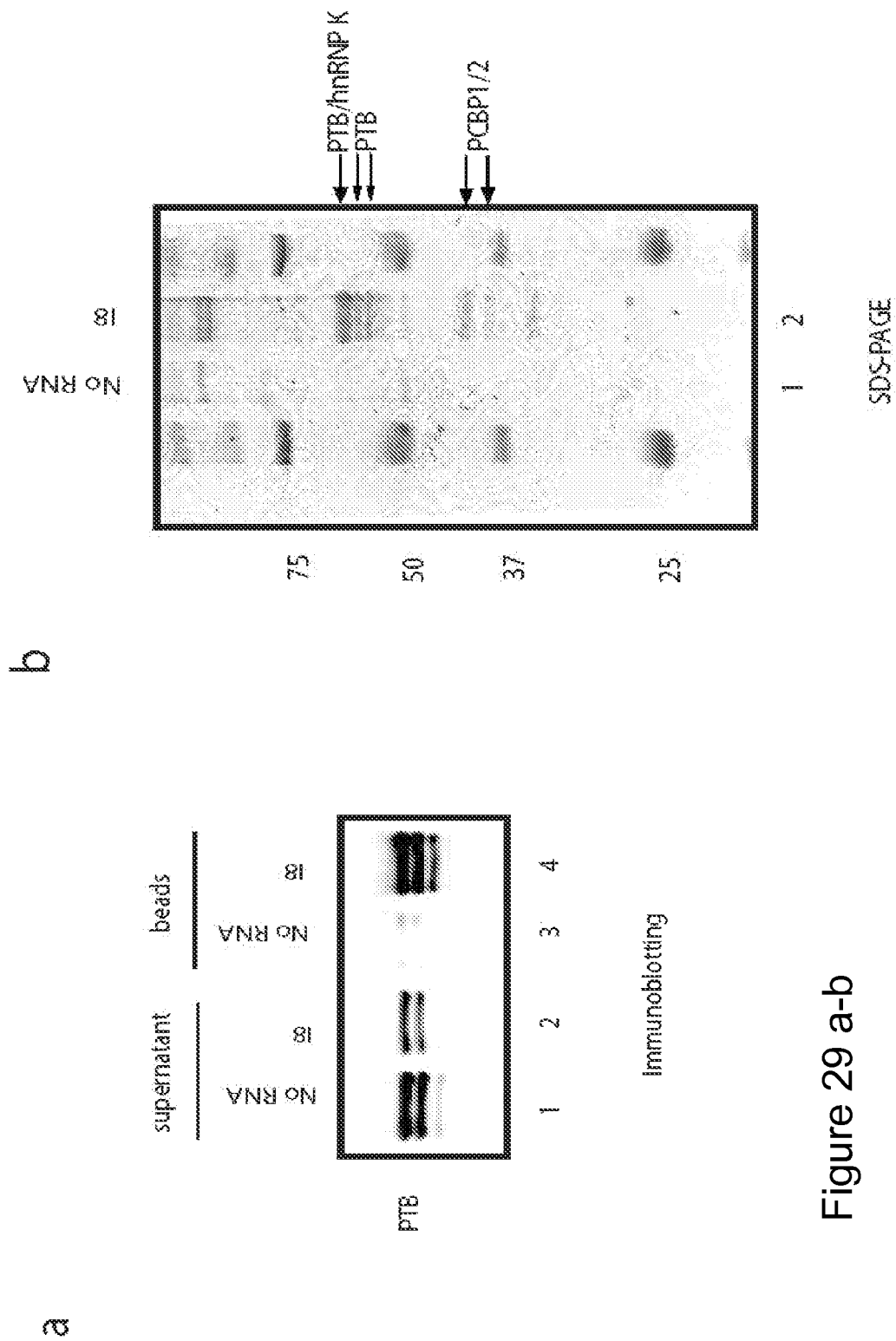
FIG. 29: *a*, PTB binds to biotinylated RNA oligo 18. After affinity chromatography using biotinylated I8 RNA supernatants (lanes 1 and 2) and protein samples bound to the beads from I8 (lane 4) and no RNA control (lane 3) were separated on 10% SDS-PAGE and analyzed by immunoblotting using an anti-PTB antibody (BB7). b. After affinity chromatography using biotinylated I8, protein samples bound to the beads from I8 (lane 2) and no RNA control (lane 1) were separated on 10% SDS-PAGE and Coomassie stained. Positions of the bands excised for mass spectrometry are indicated.
Figure 30:
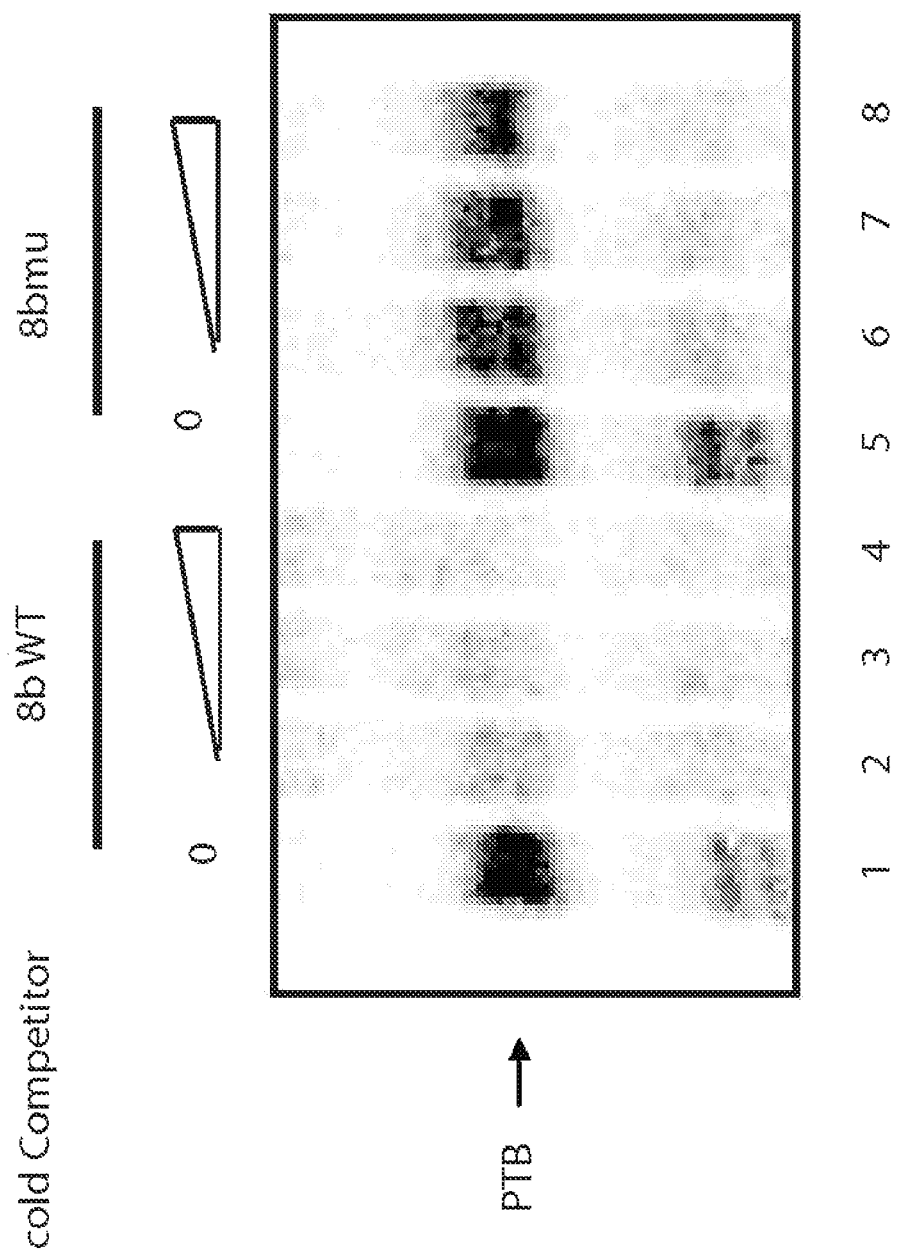
FIG. 30: PTB binding to I8 RNA is specifically abolished by a C to G mutation. $^{32}$P-UTP labeled I8 RNA (see sequence in FIG. 20) was incubated with HeLa NE in the presence of increasing amounts (0, 2, 3, 3.6 μM) of cold I8 WT RNA (lanes 1-4) or cold I8mu RNA (lanes 5-8), followed by UV crosslinking.

To explore the possibility that other splicing regulators bind upstream of E9 or E10, we constructed crosslinking substrates (48 nt) that span the region upstream of each exon. Using these RNAs for UV crosslinking showed strong binding of a 55 kDa protein to the I8 RNA probe, but not to the I9 probe (FIG. 20e). Inspection of the polypyrimidine tract upstream of E9 revealed two potential PTB (polypyrimidine tract binding protein, or hnRNPI) binding sequences (UCUUC)[10] within 35 nucleotides of the intron/exon boundary, while no such sequence exists in the E10 polypyrimidine tract. PTB frequently functions as a splicing repressor[10], often by binding repressively to the polypyrimidine tract[11]. Immunoprecipitation confirmed that the 55 kDa crosslink observed using I8 RNA is PTB (FIG. 20e), and we observed strong binding of PTB to a biotinylated version of I8 (FIG. 29). In addition, mutation of the two putative PTB binding sites from UCUUC to UGUUC significantly diminished binding (FIG. 20f; FIG. 30). Our data indicate that the splicing repressor PTB binds specifically to the polypyrimidine tract of E9.

Figure 31:
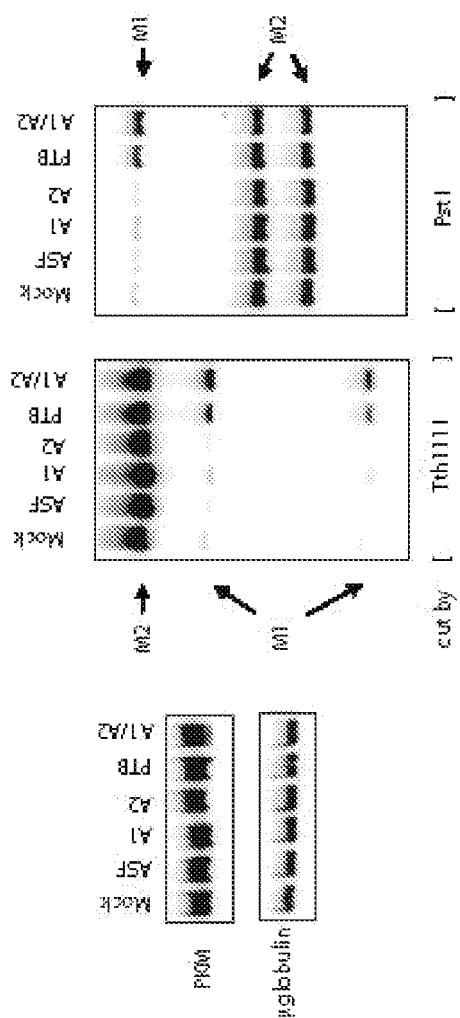
FIG. 31: Knockdowns of splicing factors have differing effects on PKM splicing. The indicated splicing factors were depleted by siRNA, followed by PKM splicing assay as outlined in FIG. 20*a*. Products corresponding to M1 and M2 are indicated with arrows. PCR products for the PKM amplicon and a load control, μglobulin, are displayed on the left. The PKM amplicons after cutting with the indicated enzyme are shown in the middle and right panels.
Figure 32:
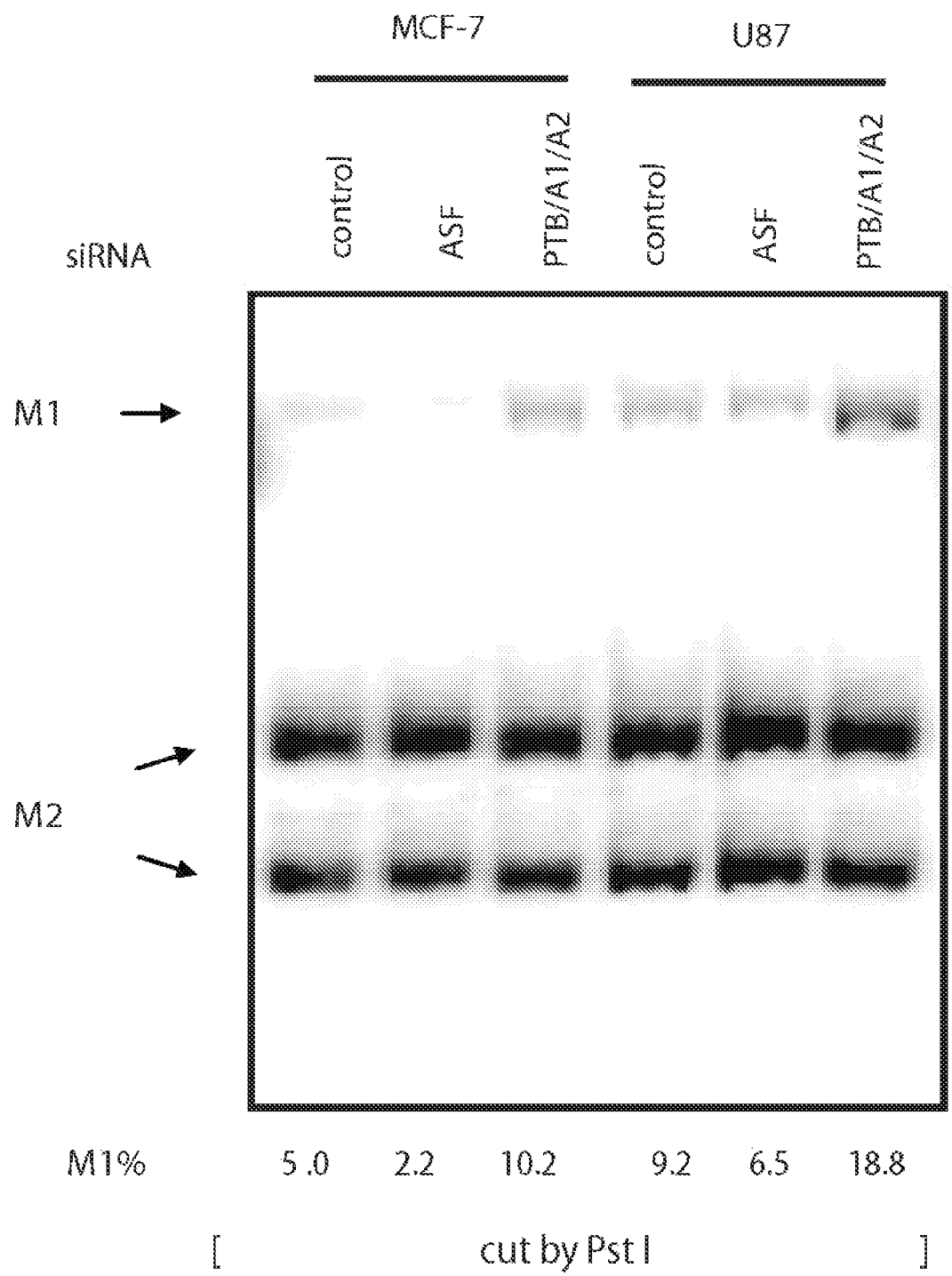
FIG. 32: Assay of PKM splicing after siRNA depletion of ASF/SF2, or simultaneous knockdown of PTB/A1/A2. siRNAs were transferred into human breast cancer cell line MCF-7 and glioblastoma cell line U87. Cells were collected after three days. Total RNA was extracted and PKM isoform ratio was estimated as described in FIG. 21*a*.
Figure 33:
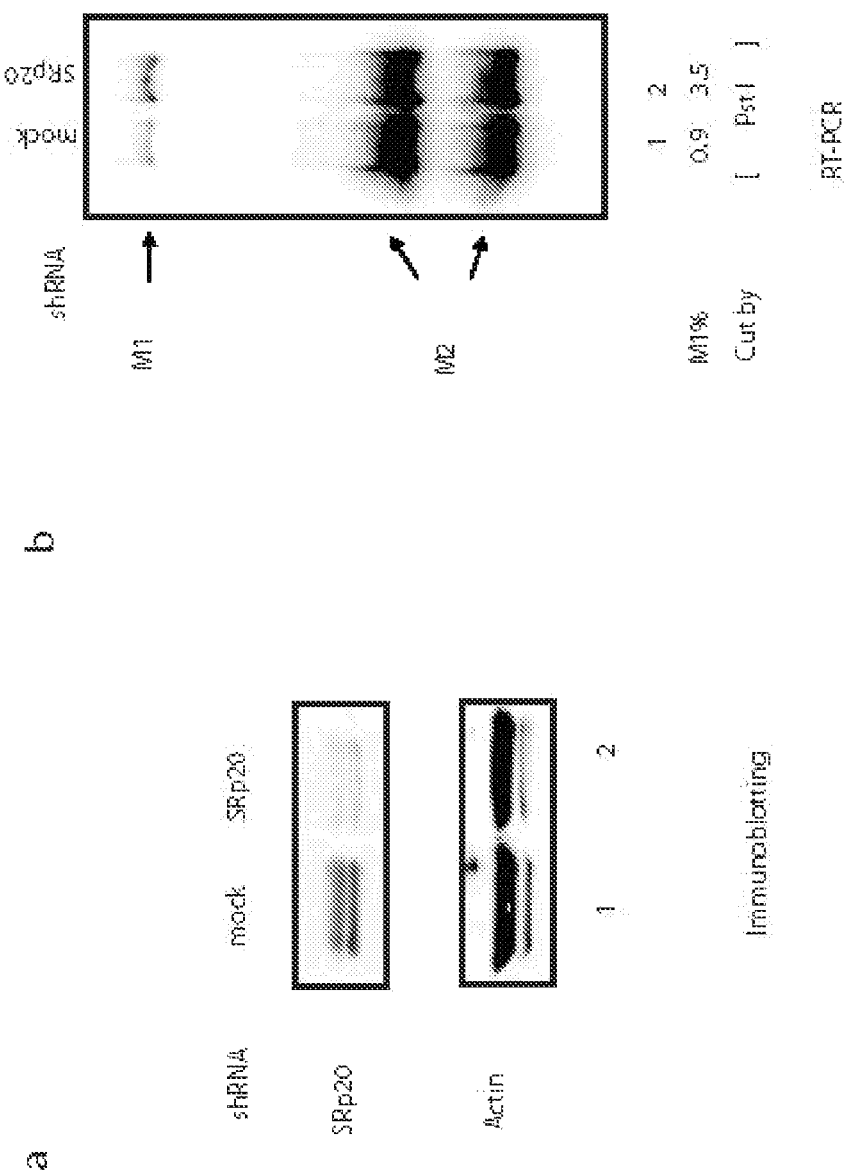
FIG. 33: SRp20 knockdown does not affect the PKM1/2 mRNA ratio. *a*, Immunoblotting to detect SRp20 protein levels in HeLa cells treated with either control shRNA (lane 1) or SRp20-targeting shRNA (lane 2). *b*, PKM1/2 ratios in control and SRp20 knockdown cells determined as in FIG. 21*a*.

Because the locations of hnRNPA1/A2 and PTB binding sites flanking E9 overlap elements critical to exon inclusion (the polypyrimidine tract for PTB[11], the site of U1snRNA-pre-mRNA base-pairing for A1/A2[12]), we speculated that these proteins are inhibitors of E9 inclusion. To examine this possibility, we used siRNA to deplete hnRNPA1, hnRNPA2 and/or PTB from HeLa cells. We assayed the PKM mRNA isoform ratio using RT-PCR followed by exon-specific restriction digestion (FIG. 21a). Knockdown of hnRNPA1 or hnRNPA2 in HeLa cells resulted in little change in splicing pattern (FIG. 31). Because we have previously observed functional redundancy of hnRNPA1/A2[7], we next simultaneously depleted both proteins (FIG. 21b). This resulted in an increase in PKM1 mRNA, from 2% to 29%, and a concomitant decrease in PKM2 mRNA (FIG. 21c; FIG. 31). PTB knockdown also increased the PKM1 isoform, to 16% (FIG. 21c; FIG. 31), consistent with earlier observations[13]. Next, we simultaneously depleted all three factors, which further increased PKM1 levels, to about 48% (FIG. 21c). Similar results were obtained using 293 cells, with the triple knockdown resulting in an increase from 5% to 67% PKM1 (FIG. 21d). Increases in PKM1 mRNA upon A1/A2/PTB knockdown were observed in all cell lines tested, including the breast cancer cell line MCF-7 and the glioblastoma cell line U87 (FIG. 32). Knockdown of two other cancer-associated splicing factors in HeLa cells, the SR proteins ASF/SF2 and SRp20, while also resulting in slowed growth, failed to significantly affect PKM1/2 ratios (FIGS. 31 and 33), indicating that the effects seen in PTB/A1/A2 depleted cells on PKM splicing are specific and not the result of pleiotropic effects due to changes in cell growth. Together, our results indicate that PTB/A1/A2 expression is the critical determinant of PKM isoform in transformed cells.

We next wished to determine whether PTB/A1/A2 expression levels and PKM1/2 alternative splicing are correlated. We first examined whether changes in PTB/A1/A2 levels correlate with changes in PKM splicing during switching from growth to quiescence. To this end, we used the mouse myoblast cell line C2C12, which, when grown to confluence and then switched to low-serum medium, undergoes myogenic differentiation, a process that includes PKM2 to PKM1 switching[14]. We differentiated C2C12 cells for 6 days, and used RT-PCR followed by restriction digestion to assess the PKM1/2 ratio each day. We observed a large increase in PKM1 and a corresponding decrease in PKM2 mRNA during differentiation (FIG. 22a). We then prepared lysates of C2C12 cells at time points throughout differentiation and examined protein levels by immunoblotting (FIG. 22b). PTB expression dropped over 70% by day 3 of differentiation, after which it remained stable, consistent with previous studies[15]. We also observed an approximately 50% decrease in hnRNPA1 levels by day 3 of differentiation, though no significant changes were observed in the level of hnRNPA2. This result is consistent with a role for PTB/A1 in maintaining high PKM2 levels in proliferating C2C12 cells.

Figure 34:
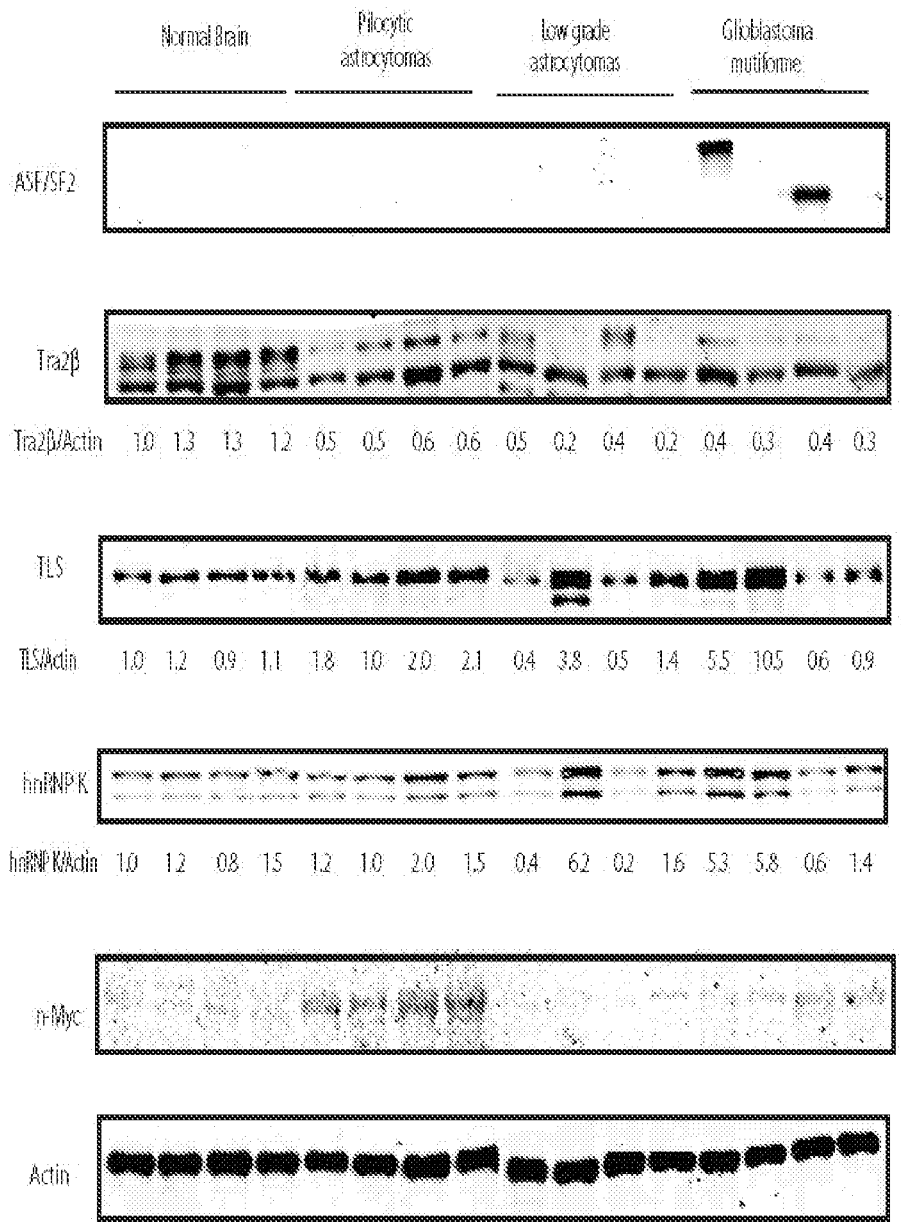
FIG. 34: Lysates of normal brain and glioma samples were immunoblotted for ASF/SF2, Tra2β, TLS, hnRNP K and n-Myc and normalized to actin. Quantitation of Tra2β, TLS and hnRNP K is indicated below each immunoblot (normal brain sample one=1). Sample order is the same as for RT-PCR and immunoblotting in FIGS. 22*c* and 22*d*.

Because of the importance of the PKM2 isoform to the growth of cancer cells, we next examined human glioma tumor samples for a correlation between PTB/A1/A2 expression and PKM splicing. We first assayed PKM1/2 mRNA levels as described earlier. Normal brain tissue ranged from 4-13% PKM2, pilocytic astrocytomas (PA) samples expressed approximately 66-77% PKM2, low grade astrocytomas (LGA) ranged from 7-73%, and glioblastoma multiforme (GBM) samples expressed 72-86% PKM2 (FIG. 22c). To explore a potential correlation between elevated PKM2 mRNA levels and expression of the regulatory proteins we identified, we performed immunoblots for PTB, hnRNPA1 and hnRNPA2. Significantly, all high-PKM2 tumors expressed elevated levels of PTB/A1/A2, with the most striking overexpression in GBMs (FIG. 22d). Consistent with their uniformly high PKM2 expression, all four PA samples also showed overexpression of the PTB/A1/A2. In LGAs the two high PKM2 tumors showed elevated expression of the three proteins, while the two low PKM2 tumors showed expression levels similar to normal brain. Immunoblotting for four other splicing factors (ASF/SF2, Tra213, TLS/FUS, and hnRNPK) revealed no correlation with PKM2 expression (FIG. 34), indicating that the correlation between an elevated PKM2/1 mRNA ratio and overexpression of PTB/A1/A2 is specific and not reflective of a general property of splicing factors.

The tight coupling of PKM2 expression to proliferation suggests that the expression of the PKM splicing regulatory proteins we identified might be under the control of a proliferation-associated regulatory mechanism. A strong candidate to control this is the oncogenic transcription factor c-Myc, which, like PTB/A1/A2, is upregulated in GBMs[16], and has been shown to bind the PTB/A1/A2 promoters[17,18] and upregulate the expression of all three[19,20]. Consistent with a role for c-Myc in PTB/A1/A2 regulation, we observed a near perfect correlation between the levels of c-Myc and PTB/A1/A2 in gliomas and differentiating C2C12 cells (FIGS. 22b and 22d). In addition, the transcription factor N-myc, which is closely related to c-Myc[21], was upregulated in PAs and to a lesser extent in GBMs (FIG. 34), indicating that this protein may in some cases contribute to PTB/A1/A2 upregulation.

Figure 35:
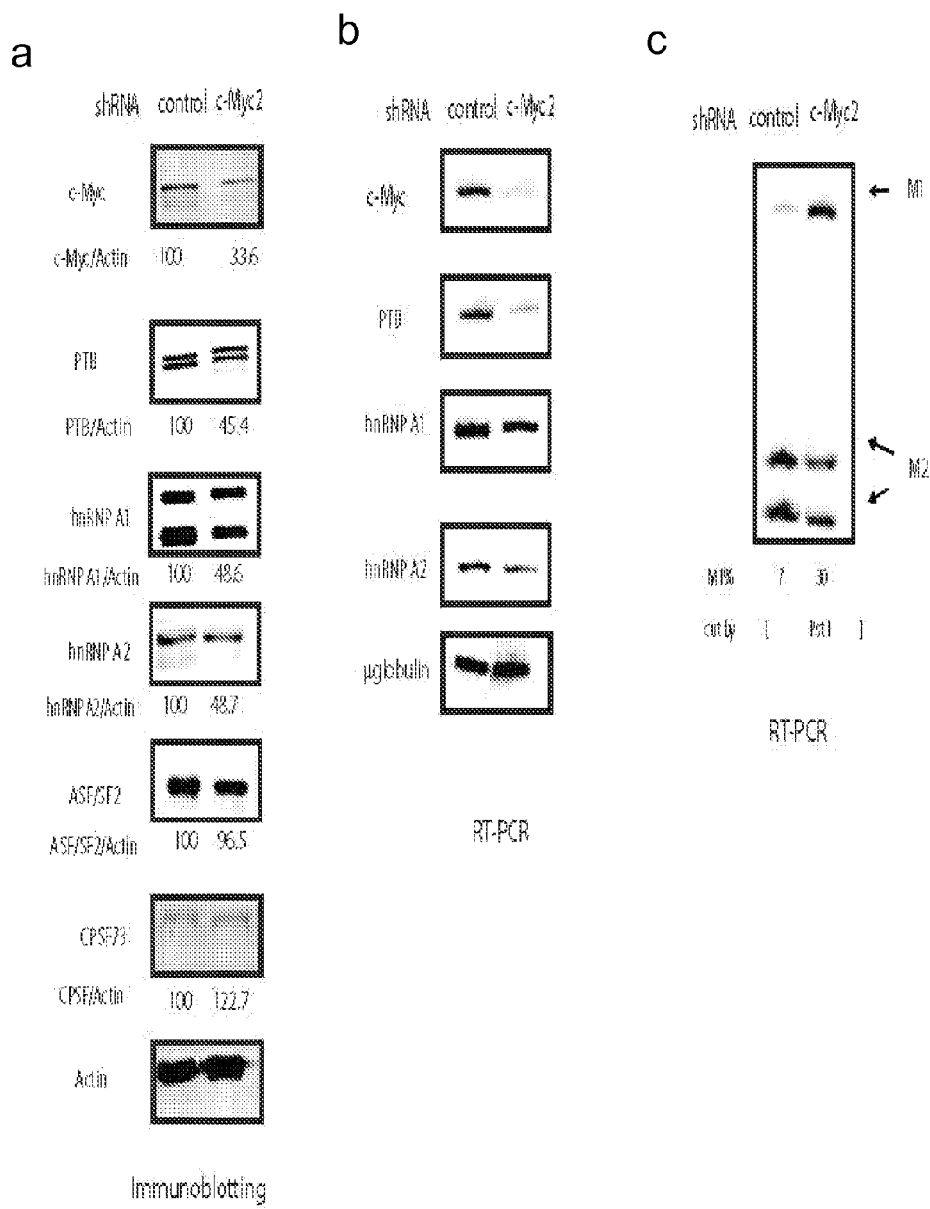
FIG. 35: A stable cell line expressing a second c-Myc-targeting shRNA also reduced PTB/A1/A2 and PKM2 mRNA levels. *a*, Immunoblotting using NIH-3T3 cells stably expressing control shRNA or c-Myc-targeting shRNA2. Signals were quantitated and normalized to actin. *b*, RT-PCR was used to determine relative mRNA levels in cells stably expressing control shRNA or c-Myc-targeting shRNA2. *c*, PKM1/2 ratios in control and c-Myc knockdown cells determined as in FIG. 21*a*.
Figure 36:
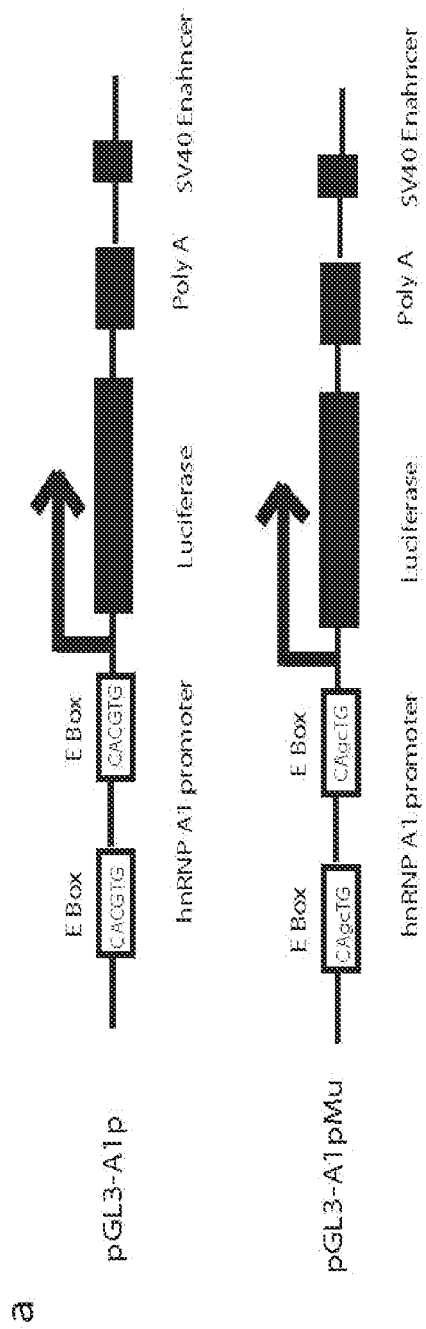
FIG. 36: c-Myc upregulates transcription form the hnRNP A1 promoter via E boxes. *a*, Diagrams showing hnRNP A1 promoter-Luciferase reporter constructs. E boxes (CACGTG) are putative c-Myc binding sites, which are located within a ~700 nt hnRNP A1 promoter region cloned upstream of the luciferase gene. pGL3-A1p contains the wild-type promoter region. pGL3-A1pMu contains mutated E boxes (indicated in the diagram). *b*, Results of dual luciferase reporter assays showing relative luciferase activity (top) activated by overexpression of c-Myc in HeLa cells by co-transfection of c-Myc expression vector and pGL3-A1p (lanes 1-3) or pGL3-A1pMu (lanes 4-6). Luciferase activity was normalized to *Renilla* luciferase activity, and pGL3-A1p activity was set as 1. Immunoblotting using c-Myc antibody to show c-Myc overexpression in transfected cells (bottom).
Figure 36:
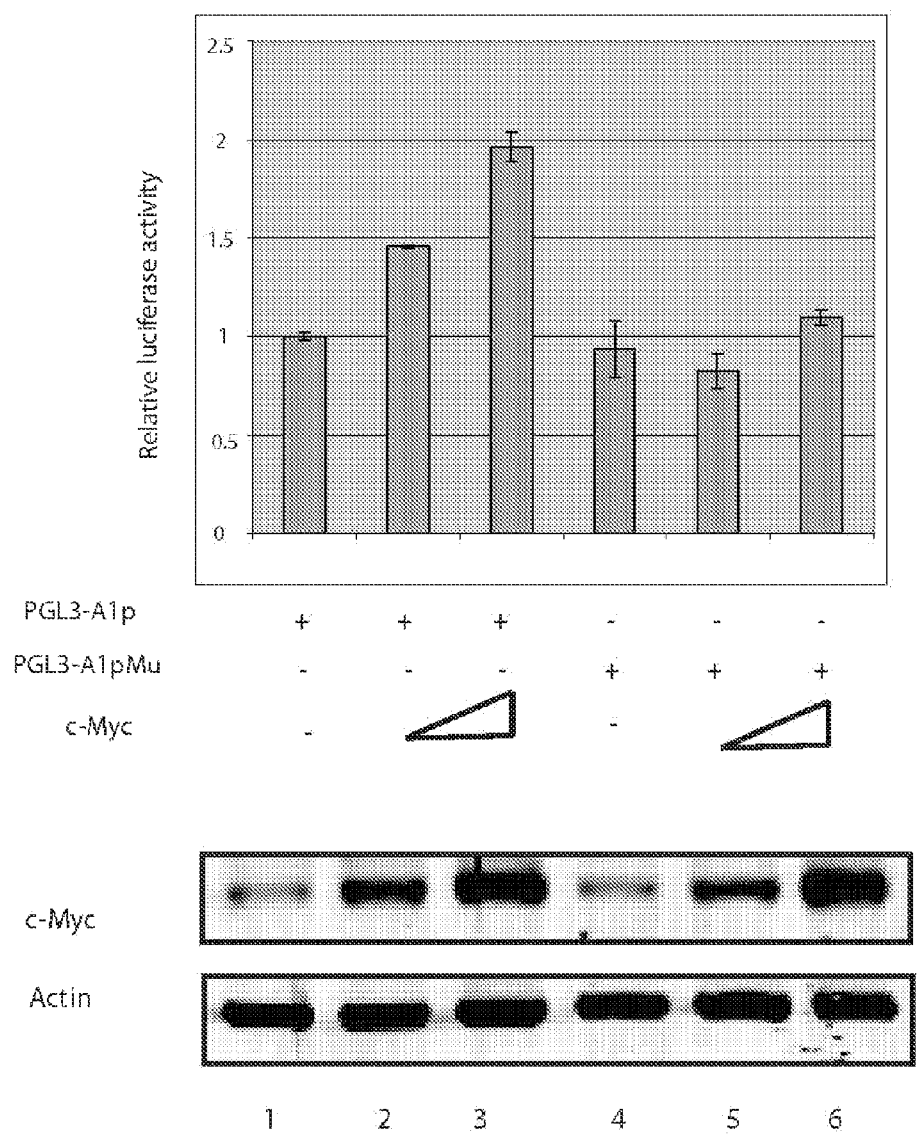

We next examined directly c-Myc's involvement in PTB/A1/A2 expression and PKM splicing regulation. We first asked whether decreasing c-Myc levels can affect PTB/A1/A2 levels and the PKM1/PKM2 mRNA ratio. To this end, we transfected NIH-3T3 cells with vectors bearing a puromycin resistance marker that express either a c-Myc-targeting shRNA or a control shRNA. Immunoblotting showed a reduction in c-Myc levels in cells stably transfected with c-Myc shRNA, compared to control cells (FIG. 23a). PTB/A1/A2 protein levels were also significantly reduced after depletion of c-Myc, in contrast with two other RNA processing factors not implicated in PKM splicing regulation, ASF/SF2 and CPSF73 (FIG. 23a). PTB/A1/A2 mRNA levels were also significantly reduced in the knockdown cells (FIG. 23b), supporting the idea that c-Myc regulates transcription of these genes. Importantly, the cells stably expressing the c-Myc shRNA showed a pronounced increase in the PKM1/2 ratio, expressing 33% PKM1 mRNA compared to 7% in the control (FIG. 23c). A separate line stably expressing a second c-Myc shRNA revealed a similarly elevated PKM1/2 ratio, as well as reduced levels of PTB/A1/A2, showing that the observed effects were not due to off-target effects of the c-Myc shRNA (FIG. 35). Additionally, we co-transfected an hnRNPA1 promoter-luciferase construct with a c-Myc expression vector[22], which resulted in a dose- and c-Myc binding site-dependent increase in promoter activity (FIG. 36).

Figure 37:
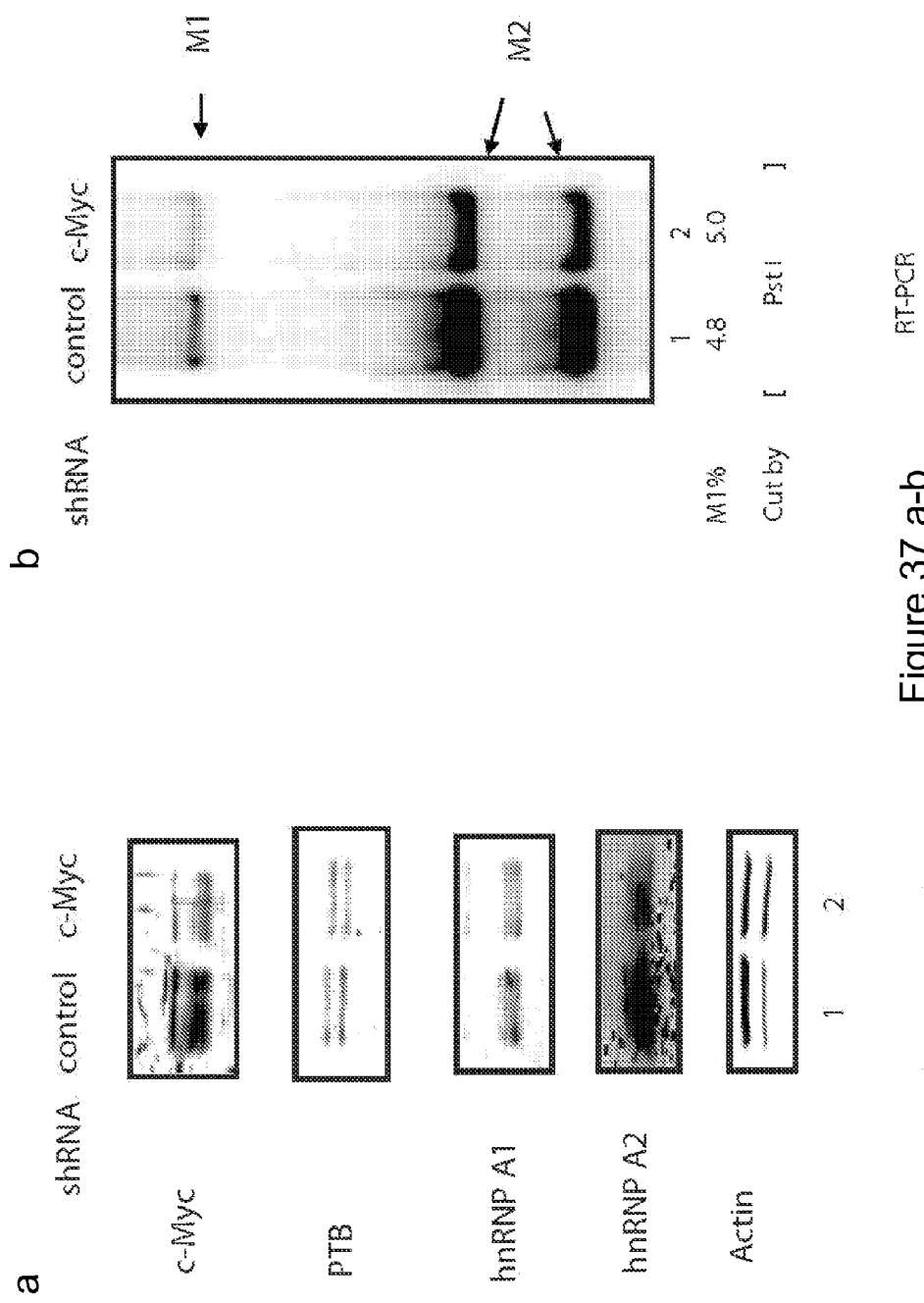
FIG. 37: c-Myc knockdown on HeLa cells does not change PKM splicing. *a*, Immunoblotting using HeLa cells transiently expressing control or human c-Myc-targeting shRNAs. *b*, PKM1/2 ratios in control and c-Myc knockdown cells determined as in FIG. 21*a*.

The above results demonstrate a direct role for c-Myc in maintaining high PTB/A1/A2 levels in NIH-3T3 cells. In contrast, c-Myc knockdown in HeLa cells revealed only a small decrease in PTB/A1/A2 levels, and no change in the PKM1/2 ratio (FIG. 37), suggesting that factors other than c-Myc might promote PTB/A1/A2 expression in these cells. One possibility is the transcription factor E2F1, which like c-Myc binds upstream of all three genes[18]. However, knockdown of E2F1, or of Rb, a negative regulator of E2F family transcription factors[23], resulted in little change in PTB/A1/A2 levels. However, since the E2F and Rb families exhibit redundancy, this result does not rule out involvement of the E2F/Rb pathway in PTB/A1/A2 regulation. Indeed, because of their importance to proliferating cells, it is likely that PTB/A1/A2 can be upregulated by proliferation-associated factors in addition to c-Myc.

The fact that PTB/A1/A2 depletion results in switching to the PKM1 isoform suggests that RNA binding proteins can control the outcome of a mutually exclusive splicing event by simultaneously acting as repressors of one exon (E9) and activators of the other (E10) (FIG. 23d). While it is easy to envision how these proteins exclude E9, how might PTB/A1/A2 promote E10 inclusion? A variety of RNA binding proteins, including hnRNPA1/A2, have been shown to stimulate splicing of an adjacent exon through intronic binding sites[24]. One proposed mechanism for this is intron definition, in which intron-binding proteins induce intronic structures conducive to inclusion of the neighboring exon[24]. We propose that, like many alternatively spliced exons, PKM E10 is poorly recognized by the splicing machinery in the absence of adjacent intron definition, and such a structure is promoted by PTB/A1/A2 binding (FIG. 23d).

We have demonstrated a critical functional consequence for observations connecting PTB/A1/A2 upregulation with cell proliferation[25,26], transformation[27,28], and a wide variety of cancers (e.g., refs. 26, 27, 29, 30). Given the critical role of these proteins in promoting PKM2 production in tumors, overexpression of some combination of them is, like PKM2 expression, likely to be a general phenomenon in cancer. The fact that the proteins show some redundancy in promoting PKM2 splicing may ensure robust re-expression of PKM2 in tumors.

Methods Summary

UV crosslinking substrates were cloned into pcDNA3 vector (Invitrogen) and UV crosslinking was performed as previously described[7]. Mutations were introduced in EI9 by PCR-based site-directed mutagenesis. Biotinylated RNAs for affinity purification were purchased from Dharmacon, and RNA affinity chromatography was carried out as described[7]. Immunoprecipitations were carried out using protein A-agarose beads (Roche). RNAi was performed as described[7]. We transfected 50 pmol of hnRNPA1 siRNA and 25 pmol of other siRNA duplex in a 24-well plate. After 72 hours, we collected cells for RNA isolation and immunoblotting. C2C12 cells were grown in DMEM (Invitrogen) supplemented with 20% fetal bovine serum (FBS) (Hyclone) at 37° C. in 5% $CO_2$. For differentiation treatment, C2C12 were plated on gelatin coated plates, allowed to reach confluence, and then switched to DMEM 2% donor equine serum (Hyclone). Human brain and glioma samples were obtained from the Bartoli Brain Tumor Bank at the Columbia University Medical Center.

Samples were homogenized and used for Trizol RNA extraction and western blotting as described[30]. In all cases, immunoblots were scanned and quantified using the LI-COR Odyssey system. c-Myc shRNA DNA sequences were purchased from Invitrogen and cloned into the pRS vector (Origene). shRNA constructs were transfected into NIH3T3 cells and stable cell lines were selected with puromycin for RNA isolation and immunoblotting. PKM1/PKM2 ratio was analyzed by extracting total RNA from cells and tissue samples and preforming by RT-PCR followed by PstI, Tth111I, or EcoNI digestion. qPCR for PTB/A1/A2 in control and c-Myc knockdown cells was performed with SYBR green from Fermentas using the Applied Biosystems 7300 real-time PCR system. hnRNPA1 promoter sequence for dual lucifereast reporter (DLR) assay was cloned into PGL3-enhancer vector (Promega) and DLR assays were performed using Dual Luciferase Reporter Assay System (Promega)

REFERENCES FOR EXAMPLE 2

1. Warburg, O. On the origin of cancer cells. *Science* 123, 309-14 (1956).
2. Christofk, H. R. et al. The M2 splice isoform of pyruvate kinase is important for cancer metabolism and tumour growth. *Nature* 452, 230-3 (2008).
3. Vander Heiden, M. G., Cantley, L. C. & Thompson, C. B. Understanding the Warburg effect: the metabolic requirements of cell proliferation. *Science* 324, 1029-33 (2009).
4. Wang, T., Marquardt, C. & Foker, J. Aerobic glycolysis during lymphocyte proliferation. *Nature* 261, 702-5 (1976).
5. Christofk, H. R., Vander Heiden, M. G., Wu, N., Asara, J. M. & Cantley, L. C. Pyruvate kinase M2 is a phosphotyrosine-binding protein. *Nature* 452, 181-6 (2008).
6. Takenaka, M. et al. Alternative splicing of the pyruvate kinase M gene in a minigene system. *Eur J Biochem* 235, 366-71 (1996).
7. Kashima, T., Rao, N., David, C. J. & Manley, J. L. hnRNP A1 functions with specificity in repression of SMN2 exon 7 splicing. *Hum Mol Genet.* 16, 3149-59 (2007).
8. Del Gatto-Konczak, F., Olive, M., Gesnel, M. C. & Breathnach, R. hnRNP A1 recruited to an exon in vivo can function as an exon splicing silencer. *Mol Cell Biol* 19, 251-60 (1999).
9. Burd, C. G. & Dreyfuss, G. RNA binding specificity of hnRNP A1: significance of hnRNP A1 high-affinity binding sites in pre-mRNA splicing. *EMBO J.* 13, 1197-204 (1994).
10. Spellman, R. & Smith, C. W. Novel modes of splicing repression by PTB. *Trends Biochem Sci* 31, 73-6 (2006).
11. Sauliere, J., Sureau, A., Expert-Bezancon, A. & Marie, J. The polypyrimidine tract binding protein (PTB) represses splicing of exon 6B from the beta-tropomyosin pre-mRNA by directly interfering with the binding of the U2AF65 subunit. *Mol Cell Biol* 26, 8755-69 (2006).
12. Pomeranz Krummel, D. A., Oubridge, C., Leung, A. K., Li, J. & Nagai, K. Crystal structure of human spliceosomal U1 snRNP at 5.5 A resolution. *Nature* 458, 475-80 (2009).
13. Spellman, R., Llorian, M. & Smith, C. W. Crossregulation and functional redundancy between the splicing regulator PTB and its paralogs nPTB and ROD1. *Mol Cell* 27, 420-34 (2007).
14. Harada, Y., Nakamura, M. & Asano, A. Temporally distinctive changes of alternative splicing patterns during myogenic differentiation of C2C12 cells. *J Biochem* 118, 780-90 (1995).
15. Boutz, P. L., Chawla, G., Stoilov, P. & Black, D. L. MicroRNAs regulate the expression of the alternative splicing factor nPTB during muscle development. *Genes Dev* 21, 71-84 (2007).
16. Zheng, H. et al. p53 and Pten control neural and glioma stem/progenitor cell renewal and differentiation. *Nature* 455, 1129-33 (2008).
17. Birney, E. et al. Identification and analysis of functional elements in 1% of the human genome by the ENCODE pilot project. *Nature* 447, 799-816 (2007).
18. Chen, X. et al. Integration of external signaling pathways with the core transcriptional network in embryonic stem cells. *Cell* 133, 1106-17 (2008).
19. Shiio, Y. et al. Quantitative proteomic analysis of Myc oncoprotein function. *EMBO J* 21, 5088-96 (2002).
20. Schlosser, I. et al. Dissection of transcriptional programmes in response to serum and c-Myc in a human B-cell line. *Oncogene* 24, 520-4 (2005).
21. Eilers, M. & Eisenman, R. N. Myc's broad reach. *Genes Dev* 22, 2755-66 (2008).
22. Wu, K. J., Mattioli, M., Morse, H. C., 3rd & Dalla-Favera, R. c-MYC activates protein kinase A (PKA) by direct transcriptional activation of the PKA catalytic subunit beta (PKA-Cbeta) gene. *Oncogene* 21, 7872-82 (2002).
23. Giacinti, C. & Giordano, A. RB and cell cycle progression. *Oncogene* 25, 5220-7 (2006).
24. Martinez-Contreras, R. et al. Intronic binding sites for hnRNP A/B and hnRNP F/H proteins stimulate pre-mRNA splicing. *PLoS Biol* 4, e21 (2006).
25. Biamonti, G. et al. Human hnRNP protein A1 gene expression. Structural and functional characterization of the promoter. *J Mol Biol* 230, 77-89 (1993).
26. Zerbe, L. K. et al. Relative amounts of antagonistic splicing factors, hnRNP A1 and ASF/SF2, change during neoplastic lung growth: implications for pre-mRNA processing. *Mol Carcinog* 41, 187-96 (2004).
27. He, X. et al. Knockdown of polypyrimidine tract-binding protein suppresses ovarian tumor cell growth and invasiveness in vitro. *Oncogene* 26, 4961-8 (2007).
28. Hanamura, A., Caceres, J. F., Mayeda, A., Franza, B. R., Jr. & Krainer, A. R. Regulated tissue-specific expression of antagonistic pre-mRNA splicing factors. *RNA* 4, 430-44 (1998).
29. Zhou, J. et al. Differential expression of the early lung cancer detection marker, heterogeneous nuclear ribonucleoprotein-A2/B1 (hnRNP-A2/B1) in normal breast and neoplastic breast cancer. *Breast Cancer Res Treat* 66, 217-24 (2001).
30. Jin, W., McCutcheon, I. E., Fuller, G. N., Huang, E. S. & Cote, G. J. Fibroblast growth factor receptor-1 alpha-exon exclusion and polypyrimidine tract-binding protein in glioblastoma multiforme tumors. *Cancer Res* 60, 1221-4 (2000).

Methods

Plasmid Constructs.

Long UV crosslinking substrates (EI9, EI10) were prepared by amplifying fragments from HeLa genomic DNA using Pfu turbo (Stratagene), and cloning the products into pcDNA3 (Invitrogen). EI9(1-20), EI9(21-49), and EI9(50-68, 18, I8mu, and I9 DNA sequences were ordered from Invitrogen and cloned into pcDNA3. Primers used to amplify genomic DNA fragments were: EI9 forward, CGC GGA TCC TTC TTA TAA GTG TTT AGC AGC AGC T (SEQ ID NO: 32), reverse, CGG AAT TCA CTG AGC CAC AGG ACC CTT TG (SEQ ID NO: 33); EI10 forward, CGC GGA TCC CTC CTT CAA GTG CTG CAG TG (SEQ ID NO: 34), reverse, CGG AAT CCT GGG CCC AGG GAA GGG G (SEQ ID NO: 35); I8E9 forward, CCC AAG CTT AAA TTC CCC ATT CTG TCT TCC CAT G (SEQ ID NO: 36), reverse, CGG GAT CCC TGC CAG ACT CCG TCA GAA CT (SEQ ID NO: 37); I9E10 forward, CCC AAG CTT CTG TCC GGT GAC TCT TCC CC (SEQ ID NO: 38), reverse, CGG GAT CCC TGC CAG ACT TGG TGA GGA CG (SEQ ID NO: 39). Mutations were introduced in EI9 by PCR-based site-directed mutagenesis. Mouse c-Myc and control shRNA DNA sequences were ordered from Invitrogen and cloned into pRS vector (Origene) with BamH I and Hind III. The hnRNPA1 promoter region, either wild-type or the E box mutant, was cloned into PGL3-enhancer vector (Promega).

Antibodies.

The following antibodies were used in this study: BB7 for human PTB IP, 3H8 for mouse/human PTB immunoblots (Sigma), MC3 for U2AF65 (Sigma), α-HA (Covance) DP3D3 for hnRNPA2 (Abcam), N-262 for c-Myc (Santa Cruz), α-Actin (Sigma), α-GAPDH (Sigma), 9H10 for hnRNPA1 (Sigma), mAb104 for SRp20.

UV Crosslinking, RNA Affinity Purification, and Immunoprecipitation Assays.

We carried out ultraviolet crosslinking as previously described[7]. Briefly, we linearized the UV crosslinking plasmids with an appropriate restriction enzyme and synthesized the RNAs with [$^{32}$p]-UTP or [$^{32}$p]-CTP. We incubated 1×10$^5$ c.p.m. RNAs with 10 µg HeLa or C2C12 NE in buffer D in a 20 µl reaction at 30° C. for 15 minutes, then irradiated the samples with ultraviolet light in a Stratalinker 1800 (Stratagene), digested them with RNase A(10 µg/ml) and resolved them by SDS-PAGE. The RNA affinity pull-down experiment and immunoprecipitation was preformed as described[7]. The 5' biotinylated EI9(50-68) and I8 RNA oligonucleotides were purchased from Dharmacon. Antibodies were bound to protein A-agarose beads prior to IP. We used the following antibodies for IP: BB7 for PTB, and MC3 for U2AF65.

In Vitro and In Vivo Splicing Assays.

Minigene containing PKM gene exon 8, exon 9, exon 10, exon 11 and flanking regions was cloned into pcDNA3 vector (Invitrogen). G to C mutation was introduced in Minigene by PCR-based site-directed mutagenesis[11]. Wildtype and mutated minigene vectors were transfected into HeLa cells. 24 hours after transfection, cells were collected and PKM1/M2 ratio was analyzed using RT-PCR followed by Pst I digestion. In vitro splicing substrates were constructed by replacing the first exon and downstream intronic sequence of AdML pre-mRNA with PKM exon 9 and downstream intron 9 sequences or sequence with mutated hnRNP A1 binding site. pre-mRNA substrates were synthesized by in vitro transcription using T7 RNA polymerase (Promega) following product protocol. In vitro splicing of the wildtype and mutated pre-mRNA was carried out using HeLa nuclear extract as described[31].

RNA Interference.

We carried out RNA interference of PTB and hnRNPA1/A2 as described[7]. Briefly, we plated HeLa, 293, MCF-7, or U87 cells at 2.5-3×10$^4$ cells per well in 24-well plates. The next day, we mixed 50 pmole of hnRNPA1 duplex RNA and 25 pmole of the other duplex RNAs with 1.5 µl lipofectamine 2000 transfection reagent (Invitrogen) plus 100 µA of Opt-MEM medium and added this to cells after RNA duplex-lipid complex formation. For double and triple knockdowns in HeLa and 293 cells, RNA duplexes were transfected simultaneously. The control RNA duplex was used to ensure that parallel experiments had equal amounts of RNA. In MCF-7 and U87 cells, the second and third RNA duplexes were transfected 6 hours after the previous transfection. 72 hours after transfection, we collected cells for RNA isolation and immunoblotting. We used the following siRNAs (Dharmacon; the sense strand sequences are given): human hnRNPA1, CAGCUGAGGAAGCUCUUCA (SEQ ID NO: 40); human hnRNPA2, GGAACAGUUCCGUAAGCUC (SEQ ID NO: 41); human PTB, GCCUCAACGUCAAGUACAA (SEQ ID NO: 42). ASF/SF2 depletion was performed as previously described[7].

c-Myc shRNA Stable Cell Lines.

Stable cell lines expressing c-Myc shRNAs or control shRNA were obtained by transfecting pRS-shRNA vectors into NIH3T3 cells followed by drug selection. Cells were plated in 10 cm plates. The next day, transfected cells were diluted and medium was replaced with medium containing a final concentration 3 µg/ml puromycin. After 7-10 days, a mixture of fast- and slow-growing colonies appeared in cells transfected with c-Myc shRNA, while only fast-growing colonies appeared in cells transfected with control shRNA. Single slow-growing colonies were isolated and cultured for c-Myc expressing cells. c-Myc expression was examined by immunoblotting. Positive colonies were collected for RT-PCR and western blotting. The following sense shRNA sequences were used: control, gat ccG AGG CTT CTT ATA AGT GTT TAC TCG AGT AAA CAC TTA TAA GAA GCC TCT TTT Ta (SEQ ID NO: 43); Mouse c-Myc shRNA1, gat ccC ATC CTA TGT TGC GGT CGC TAC TCG AGT AGC GAC CGC AAC ATA GGA TGT TTT Ta (SEQ ID NO: 44); Mouse c-Myc shRNA2, gat ccC GGA CAC ACA ACG TCT TGG AAC TCG AGT TCC AAG ACG TTG TGT GTC CGT TTT Ta (SEQ ID NO: 45); human c-Myc shRNA, gat ccC CAT AAT GTA AAC TGC CTC AAC TCG AGT TGA GGC AGT TTA CAT TAT GGT TTT Ta (SEQ ID NO: 46).

RT-PCR.

Total RNA was extracted from tissue culture and human brain tumor samples using Trizol (Invitrogen) according to the manufacturer's instructions. Total RNA (2.5-5 µg) was used for each sample in a 20 µl reaction with 0.5 µL of SuperScript III RT (Invitrogen). 1 µl of the cDNA library was used in a 50 µl PCR reaction containing 3 µCi [$^{32}$p]-dCTP. 10 µl of the PCR products were digested by Pst I and Tth111 I (human PKM) or EcoN I (mouse PKM) and the products were resolved by 6% non-denaturing PAGE. Primers used in the PCR reactions were: human PKM exon8 forward, CTG AAG GCA GTG ATG TGG CC (SEQ ID NO: 47); human PKM exon11 reverse, ACC CGG AGG TCC ACG TCC TC (SEQ ID NO: 48); mouse PKM exon 8 forward, CAA GGG GAC TAC CCT CTG G (SEQ ID NO: 49); mouse PKM exon11 reverse, ACA CGA AGG TCG ACA TCC TC (SEQ ID NO: 50), human B2M: forward, GGC TAT CCA GCG TAC TCC AAA (SEQ ID NO: 51), reverse, CGG CAG GCA TAC TCA TCT TTT T (SEQ ID NO: 52); mouse B2m: forward, TTC TGG TGC TTG TCT CAC TGA (SEQ ID NO: 53), reverse, CAG TAT GTT CGG CTT CCC ATT C (SEQ ID NO: 54). qRT-PCR was performed using the following primers: mouse hnRNPA1: forward, TGG AAG CAA TTT TGG AGG TGG (SEQ ID NO: 55), reverse, GGT TCC GTG GTT TAG CAA AGT (SEQ ID NO: 56); mouse hnRNPA2: forward, AAG AAA TGC AGG AAG TCC AAA GT (SEQ ID NO: 57), reverse, CTC CTC CAT AAC CAG GGC TAC (SEQ ID NO: 58); mouse PTB: forward, AGC AGA GAC TAC ACT CGA CCT (SEQ ID NO: 59), reverse, GCT CCT GCA TAC GGA GAG G (SEQ ID NO: 60); mouse RPL13A forward, GGG CAG GTT CTG GTA TTG GAT (SEQ ID NO: 61), reverse, GGC TCG GAA ATG GTA GGG G (SEQ ID NO: 62). Relative amounts of mRNA were calculated using the comparative Ct method.

Cell Culture and Differentiation.

C2C12 cells were grown in DMEM (Invitrogen) supplemented with 20% fetal bovine serum (FBS) (Hyclone) at 37° C. in 5% $CO_2$. For differentiation treatment, C2C12 were plated on gelatin coated plates, allowed to reach confluence, and then switched to DMEM 2% donor equine serum (Hyclone). HeLa and 293 cells were grown in DMEM, 10% FBS. NIH3T3 cells were grown in DMEM, 10% bovine calf serum (BCS) (Hyclone).

Human Brain Tumor Samples.

De-identified brain and glioma samples were obtained from the Bartoli Brain Tumor Bank at the Columbia University Medical Center. Non-cancerous samples removed from epileptic patients were used for normal brain. Approximately 25-200 mg of each sample was obtained. Half of the homogenate was used for Trizol RNA extraction, the other half of each sample was processed for immunoblotting as described[30].

Dual Luciferase Reporter (DLR) Assay.

c-Myc expression vector and hnRNP A1 promoter vector were co-transfected into HeLa cells. 24 hours after transfection, cells were collected and DLR assays were preformed using Dual Luciferase Reporter Assay System (Promega) following product protocol. Krainer, A. R., Maniatis, T., Ruskin, B., & Green, M. R., Normal and mutant human beta-globin pre-mRNAs are faithfully and efficiently spliced in vitro. Cell 36, 993-1005 (1984).

Example 3

Overexpression of hnRNP Proteins PROMOTES Alternative Splicing of Pyruvate Kinase M2 Transcripts in Cancer Cells Cancer cells avidly take up glucose and convert it to lactate while eschewing oxidative phosphorylation, a phenomenon critical for maximal tumorigenicty and in part explained by the almost universal reversion of tumors to the embryonic form of pyruvate kinase, PKM2. PKM2 and the adult isoform, PKM1, are produced from the same gene, and differ at a single mutually exclusive mRNA exon.

To investigate the regulatory mechanism of this alternative splicing (AS) event, we first identified protein regulators that bind to the flanking region of the regulated exons. Using UV crosslinking and RNA affinity chromatography assays, we found that hnRNP A1/A2 bind to the region immediately downstream of exon 9 5' splice site but not that of exon 10. This region contains a UAGGGC sequence, the mutation of which greatly reduces the binding of hnRNP A1/A2. We also found that polypyrimidine tract binding protein (PTB) binds much more strongly to the polypyrimidine (py) tract upstream of exon 9 than to that upstream of exon 10. Furthermore, PTB appears to compete with U2AF65 for binding to the py tract. To study the potential role of hnRNP A1/A2 and PTB in regulating PKM AS, we depleted these proteins by RNAi, individually and in combinations, in multiple transformed cell lines, including Hela, HEK293, breast cancer cell line MCF7 and glioblastoma cell line U87. Strikingly, we observed increased PKM1 isoform when hnRNP A1/A2 were depleted together and when PTB was depleted, and further increased PKM1 levels were observed when all three factors were depleted. These results indicate that hnRNP A1/A2 and PTB suppress the adult PKM1 isoform and promote the production of PKM2 in transformed cell lines.

We next examined the potential correlations between hnRNP A1/A2/PTB expression levels and PKM1/2 regulation. In mouse myoblast C2C12 cells, we observed a large increase in PKM1 and a corresponding decrease in PKM2 during differentiation. We found that PTB levels dropped by 80% and A1 by 50% during differentiation. To correlate PTB/A1/A2 expression levels and the PKM AS pattern in tumors, we examined the protein levels and PKM isoform in different grade human gliomas. Significantly, all high-PKM2 tumors expressed elevated levels of PTB/A1/A2, with the most striking overexpression in glioblastoma multiformes. Thus, we establish a relationship between PKM isoform expression and overexpression of PTB, hnRNP A1/A2.

These results suggest there is tight coupling of PKM2 expression to proliferation and the regulatory proteins identified might be under the control of a proliferation-associated regulatory mechanism. Myc has been shown to bind the promoters of the PTB, hnRNP A1, and hnRNP A2 genes, and it is also known to induce expression of the glycolytic enzyme lactate dehydrogenase-A, necessary for lactate production during aerobic glycolysis. We observed a correlation between Myc expression, PTB/A1/A2 overexpression, and PKM2 expression in the glioma samples, while a drop in Myc level during C2C12 differentiation precedes a drop in PTB and hnRNP A1 levels in that process. Strikingly, depletion of Myc in NIH3T3 cells using RNAi led to decreased expression of PTB/A1/A2 and also increased PKM1 expression.

Together, our results define a transcription-splicing pathway that is deregulated in multiple cancers and is required for tumor cell growth.

Example 4

An in vivo rodent model of gliomagenesis will be used to determine the in vivo effects of overexpression of PTB, hnRNPA1, hnRNPA2 to tumor growth. Beadle et al., "The Role of Myosin II in Glioma Invasion of the Brain" *Mol Biol Cell*. 2008 August; 19(8): 3357-3368; Marcela Assanah et al. "Glial Progenitors in Adult White Matter Are Driven to Form Malignant Gliomas by Platelet-Derived Growth Factor-Expressing Retroviruses" *The Journal of Neuroscience*, Jun. 21, 2006, 26(25):6781-6790; and references therein.

Example 5

The rodent model of Example 4 will be used to determine the effect of a combination of anti-PTB, hnRNPA1, and hnRNPA2 inhibitory RNA molecules to the rodent model of gliomagenesis.

Viral vectors(s) are used for delivery of some combination of anti-PTB, hnRNPA1, and hnRNPA2 shRNA in mice/rats of Example 4, which have gliomas. The effect of anti-PTB, hnRNPA1, hnRNPA2 shRNA on growth, migration, or other characteristics of the gliomas is determined by methods and assays known in the art, and as described herein.

Example 6

Animal cancer models will be used to determine the effect of a combination of anti-PTB, hnRNPA1, and hnRNPA2 inhibitory RNA molecules on tumorigenesis. Various tumor cells will be injected in animal models, for example immunocompromized rodents, and the animals will be treated with anti-PTB, hnRNPA1, hnRNPA2 shRNAs. Tumor formation and/or tumor growth will be monitored by methods known in the art.

Example 7

Various cancer cell lines will be used to determine the effect of a combination of anti-PTB, hnRNPA1, and hnRNPA2 inhibitory RNA molecules on growth, migration, or other characteristics of the examined cancer cells. Various cancer cell lines are known and used in the art, and are contemplated for use herein.

Human Glioblastoma Cell Lines:

U87 MG, T98MG, U251, will be purchased from American Type Culture Collection and cultured in DMEM supplemented with 10% FBS (Intergen Co., Purchase, N.Y., USA), penicillin (1OOIU/mL), and streptomycin (10OIlg/mL) (Invitrogen Life Technologies, Carlsbad, Calif., USA) at 37° C. and 5% CO2. Other cancer cell lines are also commercially available.

Cancer cells are treated with inhibitory RNA or control RNA. Cell division, proliferation and/or migration of cancer cell, including glioblastoma cells, are expected to be significantly reduced compared to cells which are not treated with inhibitory RNA, for example cells transfected with a control vector.

We next determined the effect of a combination of anti-PTB, hnRNPA1, and hnRNPA2 inhibitory RNAs on growth of tumor cells.

Reagents:

Tumor Cell Lines:

MGPten: murine glioblastoma Pten$^{-/-}$ cell line (from Canoll lab); MGPP: murine glioblastoma p53$^{-/-}$ and Pten$^{-/-}$ cell line (from Canoll lab); C6: Rat C6 glioma cell line (from ATCC).

Growth Media:

DMEM+10% FBS for C6 rat glioma cell line; Basal-B104 conditioned media with supplemental PDGF and FGF for MGPten and MGPP cell lines.

```
Short hairpin RNAs (shRNAs):
anti-PTB shRNA:
                                (SEQ ID NO: 63)
CCAAAGCCTCTTTATTCTCTTCTCGAGAAGAGAATAAAGAG

GCTTTGGTTTTT;

anti-hnRNPA1 shRNA:
                                (SEQ ID NO: 64)
GCCACAACTGTGAAGTAAGAACTCGAGTTCTTACTTCACAG

TTGTGGCTTTTT;

anti-hnRNPA2 shRNA:
                                (SEQ ID NO: 65)
GTCACAATGCAGAAGTTAGAACTCGAGTTCTAACTTCTGCA

TTGTGACTTTTT;

Control shRNA:
                                (SEQ ID NO: 66)
CAACAAGATGAAGAGCACCAACTCGAGTTGGTGCTCTTCAT

CTTGTTGTTTTT.
```

Protocol:

Tumor cells were seeded in a 24-well plate (per well 2000 MGPten cells, 5000 MGPP cells, or 5000 C6 cells). After 24 hours of growth, cells were infected with a lentivirus expressing a control shRNA or a combination of anti-PTB, hnRNPA1 and hnRNPA2 shRNAs. After growth of an additional 4 days (C6) or 7 days (MGPten and MGPP), cells were photographed under a fluorescence microscope (Carl Zeiss Inc.) and the number of cells was calculated using a hemocytometer.

Figure 38:
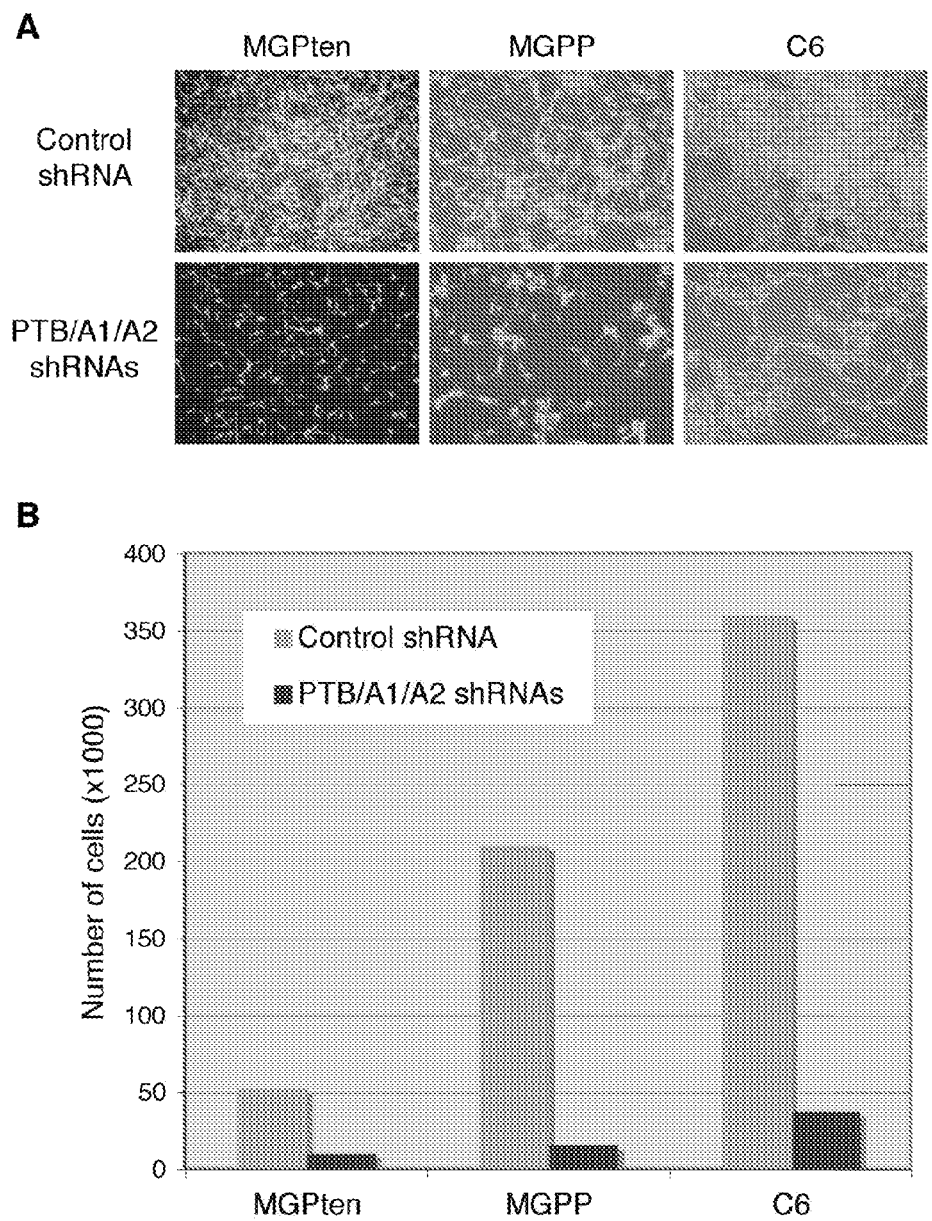
FIG. 38: *a*, Photographs of the examined tumor cells (green in red background, 40× magnification) after treatments. The cell numbers are shown in FIG. 38B. When treated with a combination of anti-PTB, hnRNPA1, and hnRNPA2 inhibitory shRNAs, all the examined tumor cell lines show reduced growth (i.e. fewer cells after days of growth), compared to the cells treated with a control shRNA.

Result:

FIG. 38A shows photographs of the examined tumor cells (green in red background, 40× magnification) after treatments. The cell numbers were shown in FIG. 38B. When treated with a combination of anti-PTB, hnRNPA1, and hnRNPA2 inhibitory shRNAs, all the examined tumor cell lines show reduced growth (i.e. fewer cells after days of growth), compared to the cells treated with a control shRNA.

Example 8

Alternative splicing is a critical regulatory mechanism of cell growth and differentiation. Transcripts from as many as 70% of human genes are subject to alternative splicing. Numerous genetic diseases are caused by defects in alternative splicing. Many other diseases, including cancer, can reflect changes in splicing pathways.

Alternative splicing is found in cancer: Expression of nearly all genes implicated in the prevention or progression of cancer involves alternative splicing. Many disease-related mutations in tumor suppressors function by disrupting splicing regulatory elements (e.g. BRCA1). Tumor-associated changes in alternative splicing can result in proteins with increased oncogenic properties (e.g. Ron, CD44, MDM2). Likewise, changes in alternative splicing can lead to production of proteins that bring about increased tumorgenesis (e.g. pyruvate kinase).

SR Proteins are a family of modulators of mRNA metabolism in animals and plants. They have multiple functions in pre-mRNA splicing. Some function in other aspects of mRNA metabolism, such as nuclear export, translation and turnover. Some also act to prevent genome instability by blocking R-loop formation during transcription. Most are overexpressed in tumors and at least one is tumorigenic in nude mice.

Figure 39:
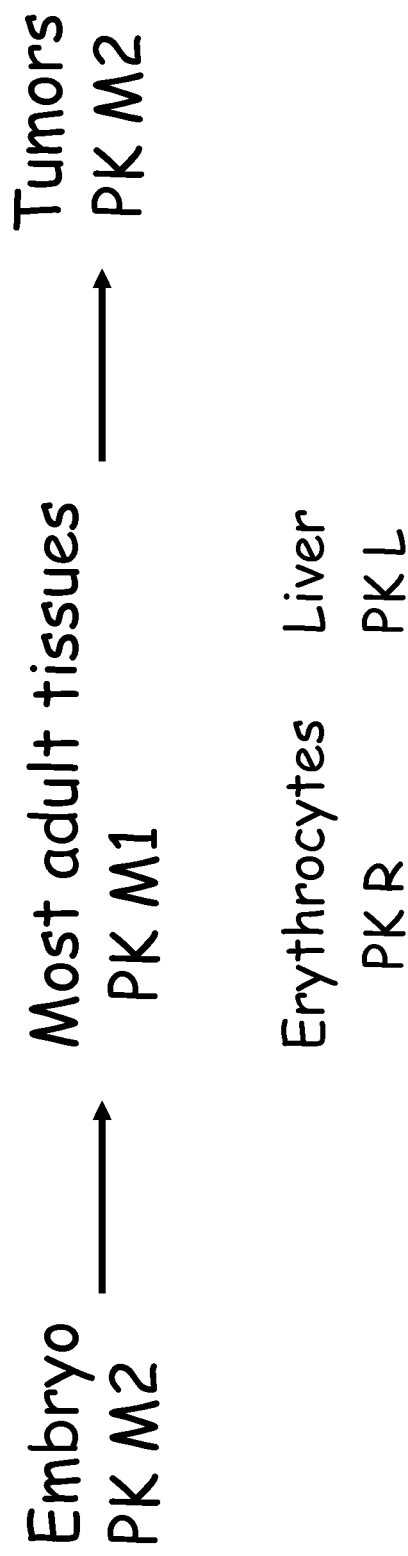
FIG. 39: Pyruvate kinase isoform expression. Properties of PKM1 and PKM2 are as follows. M1 is constitutively active, M2 regulated. M2 activity can be induced by binding of allosteric regulator phosphofructose 1-6 bisphosphate. Binding of tyrosine-phosphorylated peptides to M2 causes release of phosphofructose 1-6 bisphosphate. In tumor cells, the inactive form predominates.

Pyruvate kinase isoform expression is shown in FIG. 39. Properties of PK M1 and PK M2 are as follows. M1 is constitutively active, M2 regulated. M2 activity can be induced by binding of allosteric regulator phosphofructose 1-6 bisphosphate. Binding of tyrosine-phosphorylated peptides to M2 causes release of phosphofructose 1-6 bisphosphate. In tumor cells, the inactive form predominates.

Figure 40:
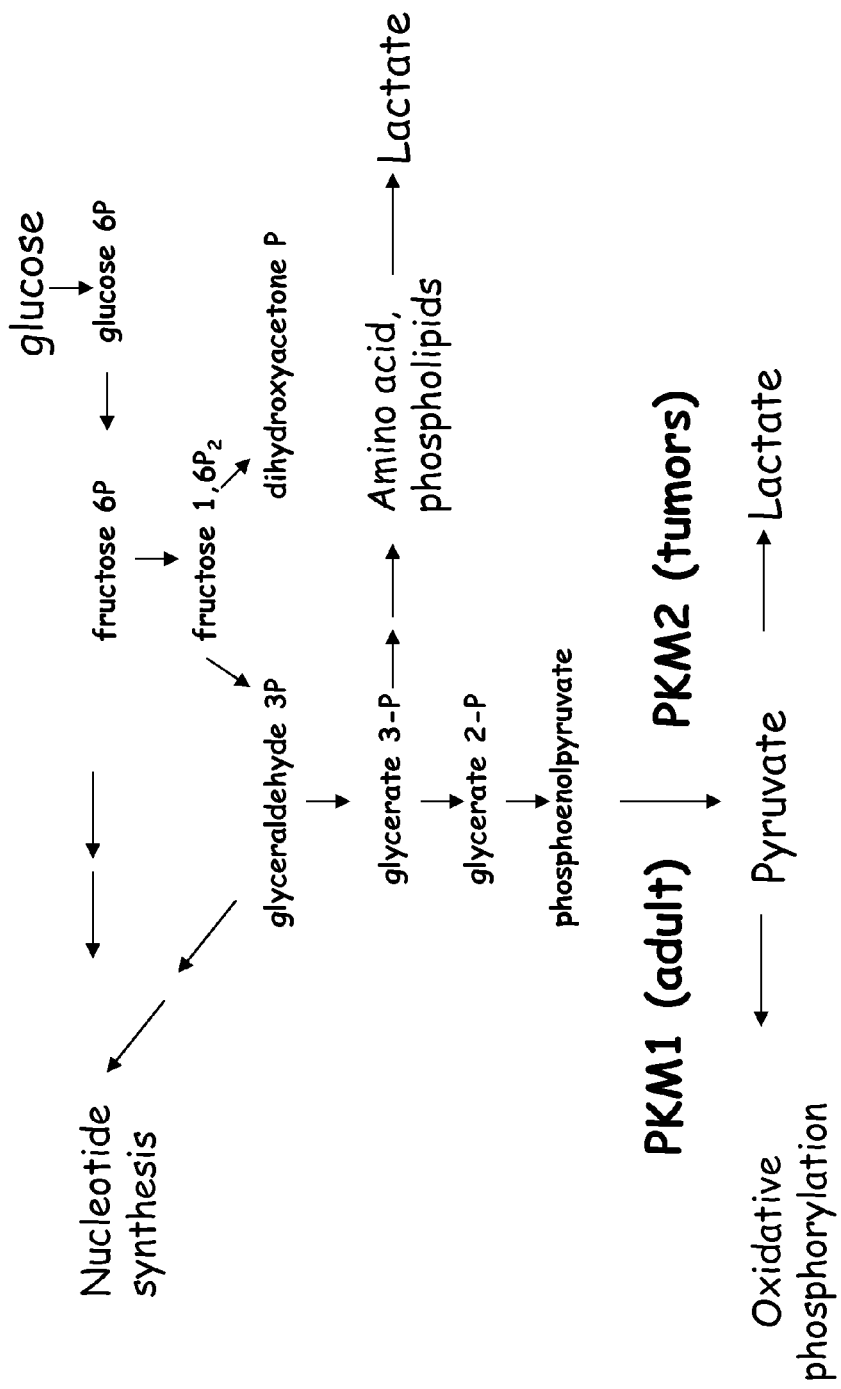
FIG. 40: The PK M1 to M2 switch enables tumor cells to use glucose for biosynthesis and contributes to the Warburg effect.

The PK M1 to M2 switch enables tumor cells to use glucose for biosynthesis and contributes to the Warburg effect (FIG. 40).

Figure 41:
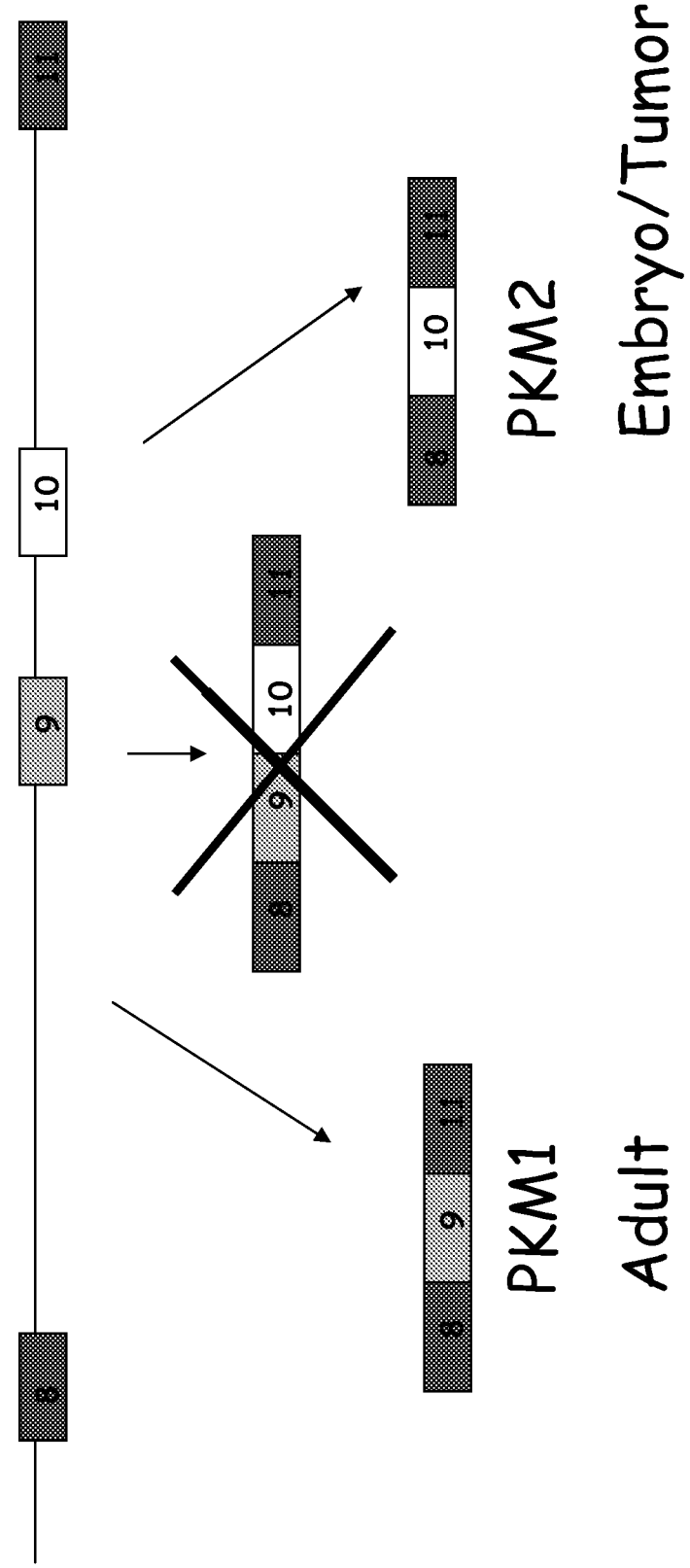
FIG. 41: Pyruvate kinase M primary transcripts are alternatively spliced to produce M1 or M2. Inclusion of exons 9 and 10 is mutually exclusive, giving rise to PKM1 (exon 9) or PKM2 (exon 10) isoforms. PKM1 are adult and PKM2 are embryo/tumor.

Pyruvate kinase M primary transcripts are alternatively spliced to produce M1 or M2 (FIG. 41). Inclusion of exons 9 and 10 is mutually exclusive, giving rise to PKM1 (exon 9) or PKM2 (exon 10) isoforms.

Regulation of alternative splicing. Alternative splicing is often regulated by proteins that bind to pre-mRNA and promote exon inclusion or exclusion. Two major classes of proteins are commonly associated with AS regulation: SR proteins frequently bind to exonic splicing enhancers and promote exon inclusion, hnRNP proteins usually bind to exonic or intronic silencers to promote exon exclusion.

Figure 42:
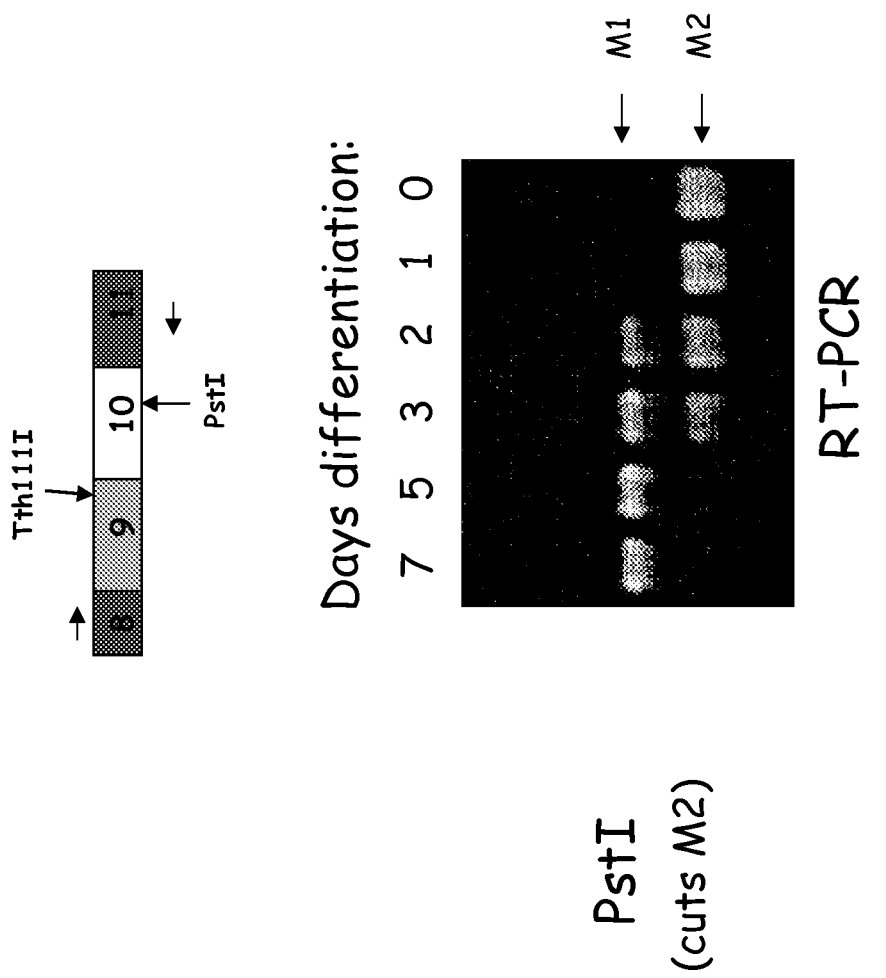
FIG. 42: Cell culture model for M2-M1 splicing switch. C2C12 mouse myoblasts differentiate into myotubes upon growth to confluence and replacement of medium with 2% equine serum.

Cell culture model for M2-M1 splicing switch (FIG. 42). C2C12 mouse myoblasts differentiate into myotubes upon growth to confluence and replacement of medium with 2% equine serum.

Figure 43:
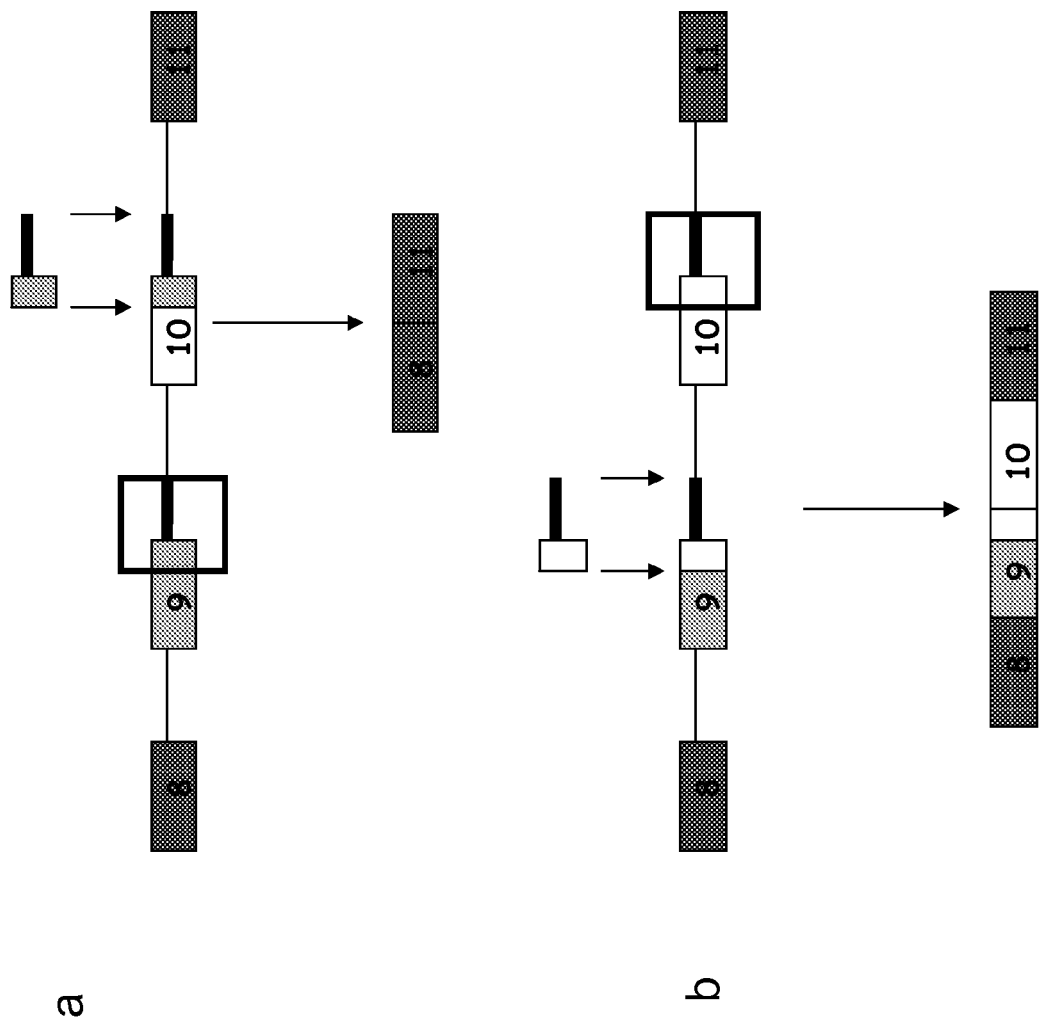
FIG. 43: Regions spanning the intron 9 and/or intron 10 5' splice sites are responsible for exon 9 exclusion in M2 selecting cells. Replacement experiment in cells that include exon 10.

Regions spanning the intron 9 and/or intron 10 5' splice sites are responsible for exon 9 exclusion in M2 selecting cells (FIG. 43). Replacement experiment in cells that include exon 10. (Takenaka et al., Eur. J. Biochem., 1996).

Figure 44:
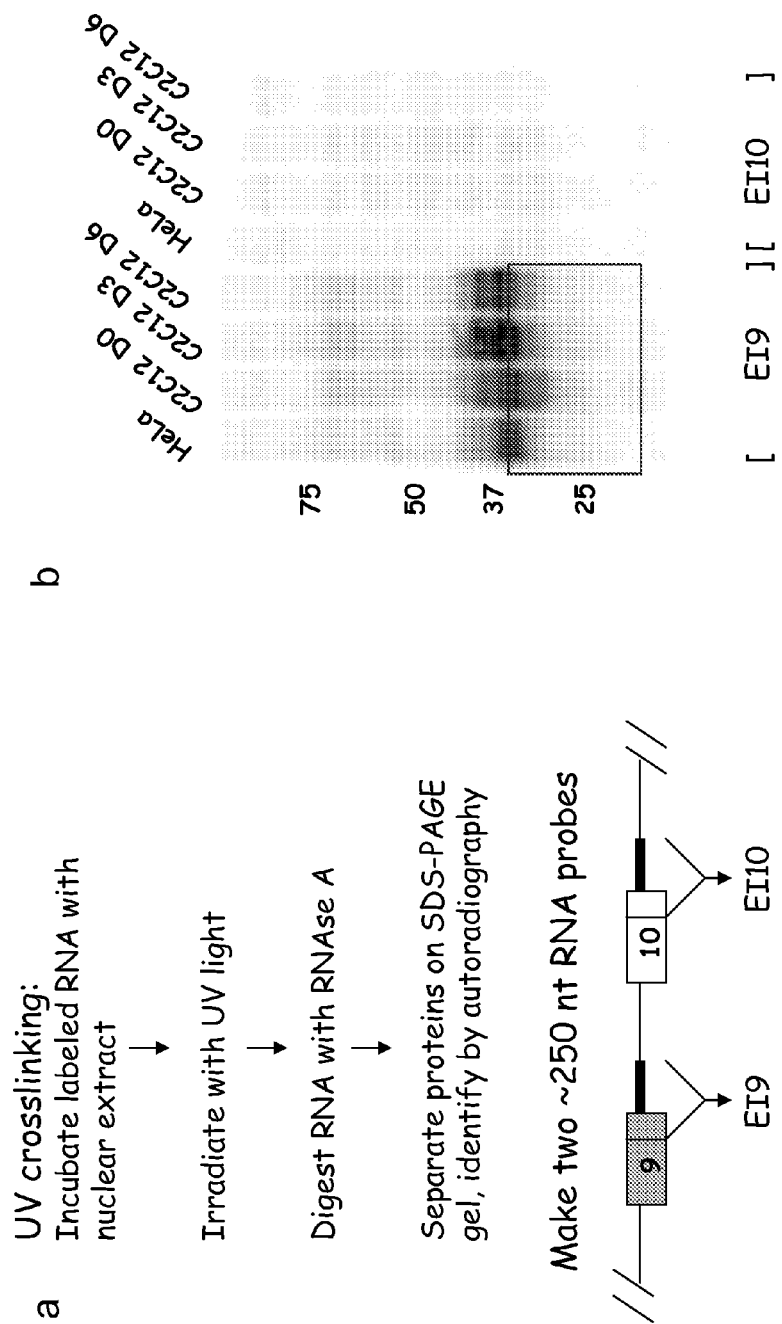
FIGS. 44 *a-b*: UV crosslinking identifies strong protein binding near the exon 9 5' splice site.

UV crosslinking identifies strong protein binding near the exon 9 5' splice site (FIGS. 44 a-b).

Figure 45:
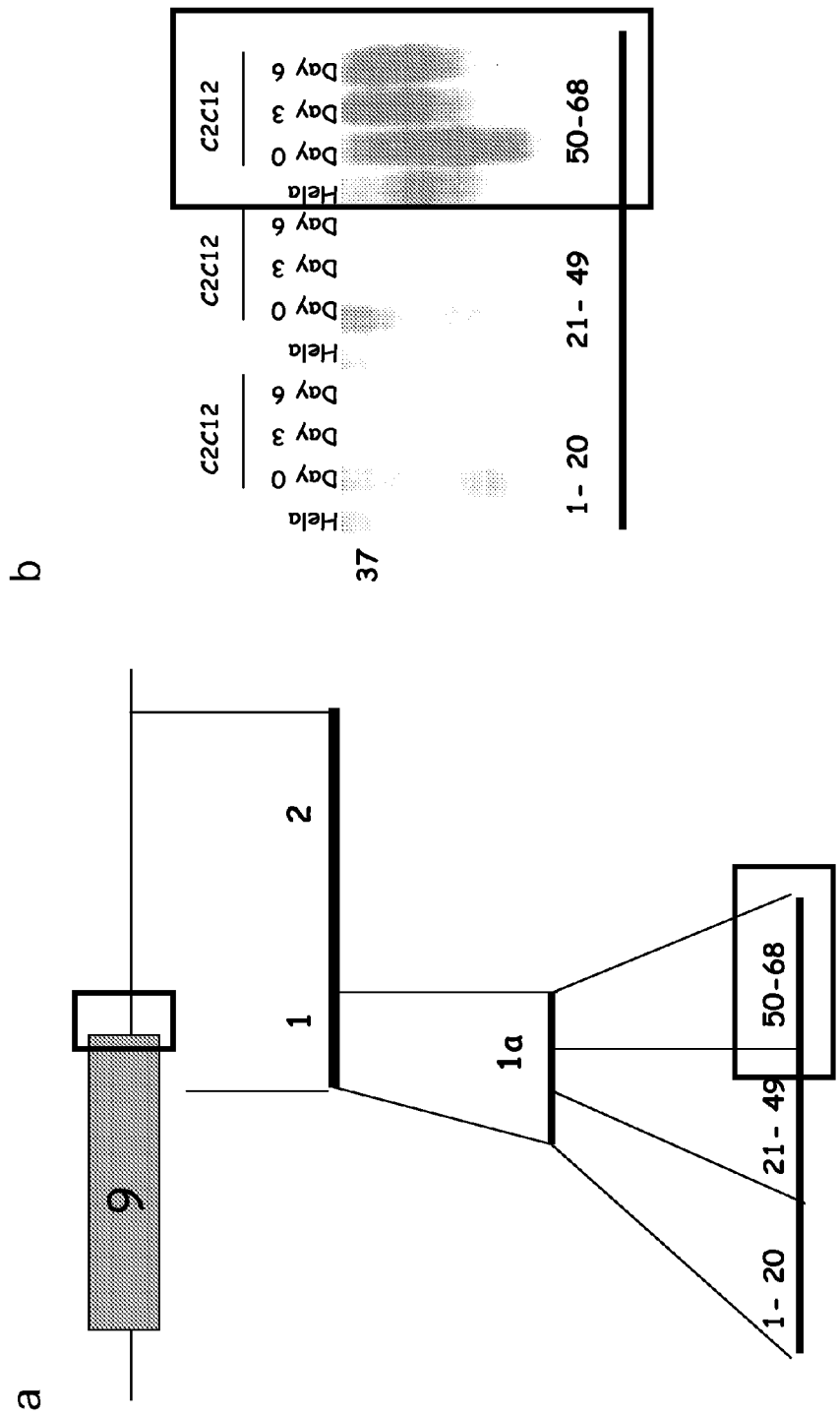
FIGS. 45 *a-b*: Strong protein binding maps to a 19 nt region spanning the exon 9 5' splice site.

Strong protein binding maps to a 19 nt region spanning the exon 9 5' splice site (FIGS. 45 a-b).

Figure 46:
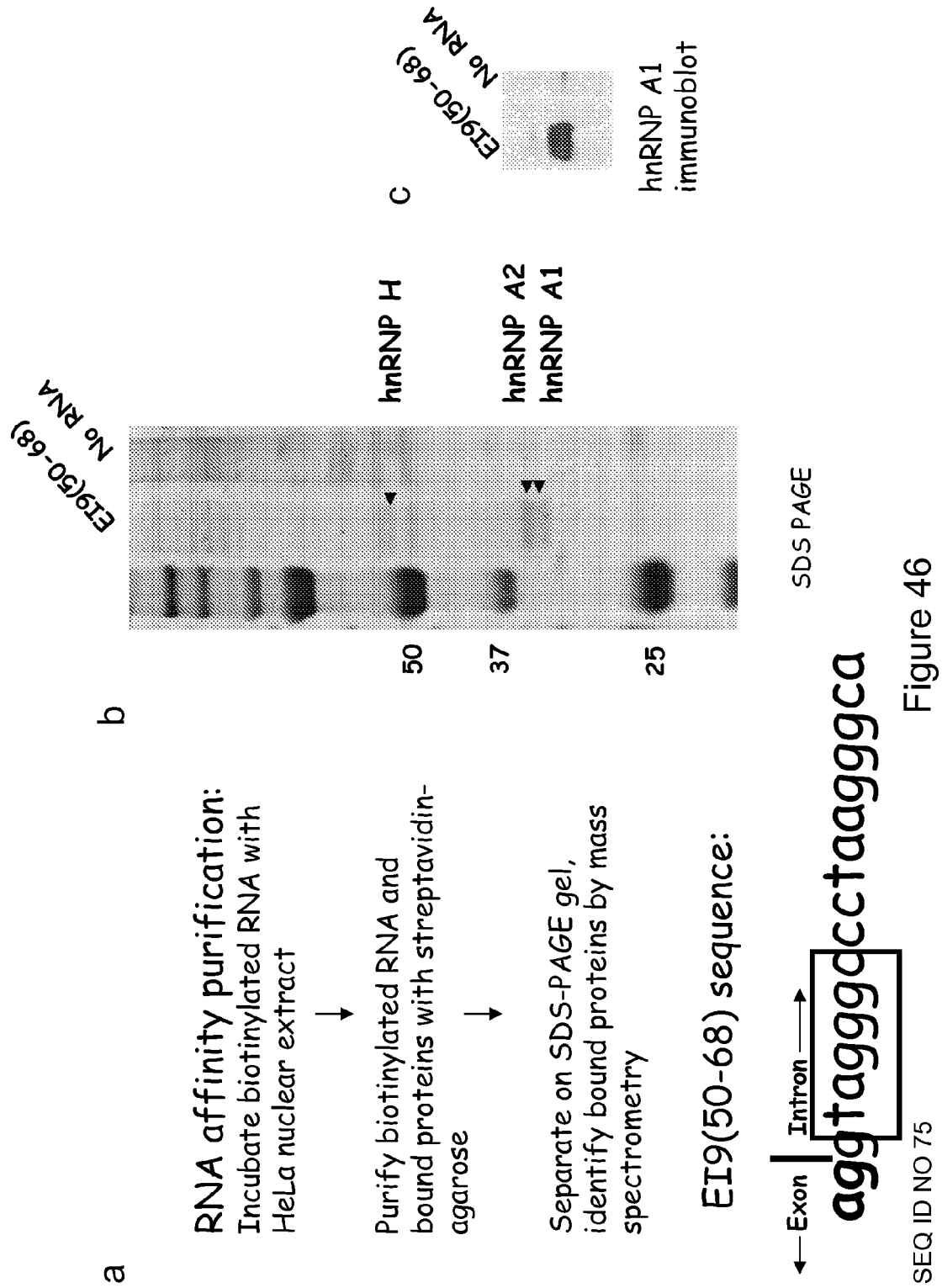
FIGS. 46 *a-c*: RNA affinity purification of EI9(50-68) binding proteins.

RNA affinity purification of EI9(50-68) binding proteins (FIGS. 46 a-c).

Figure 47:
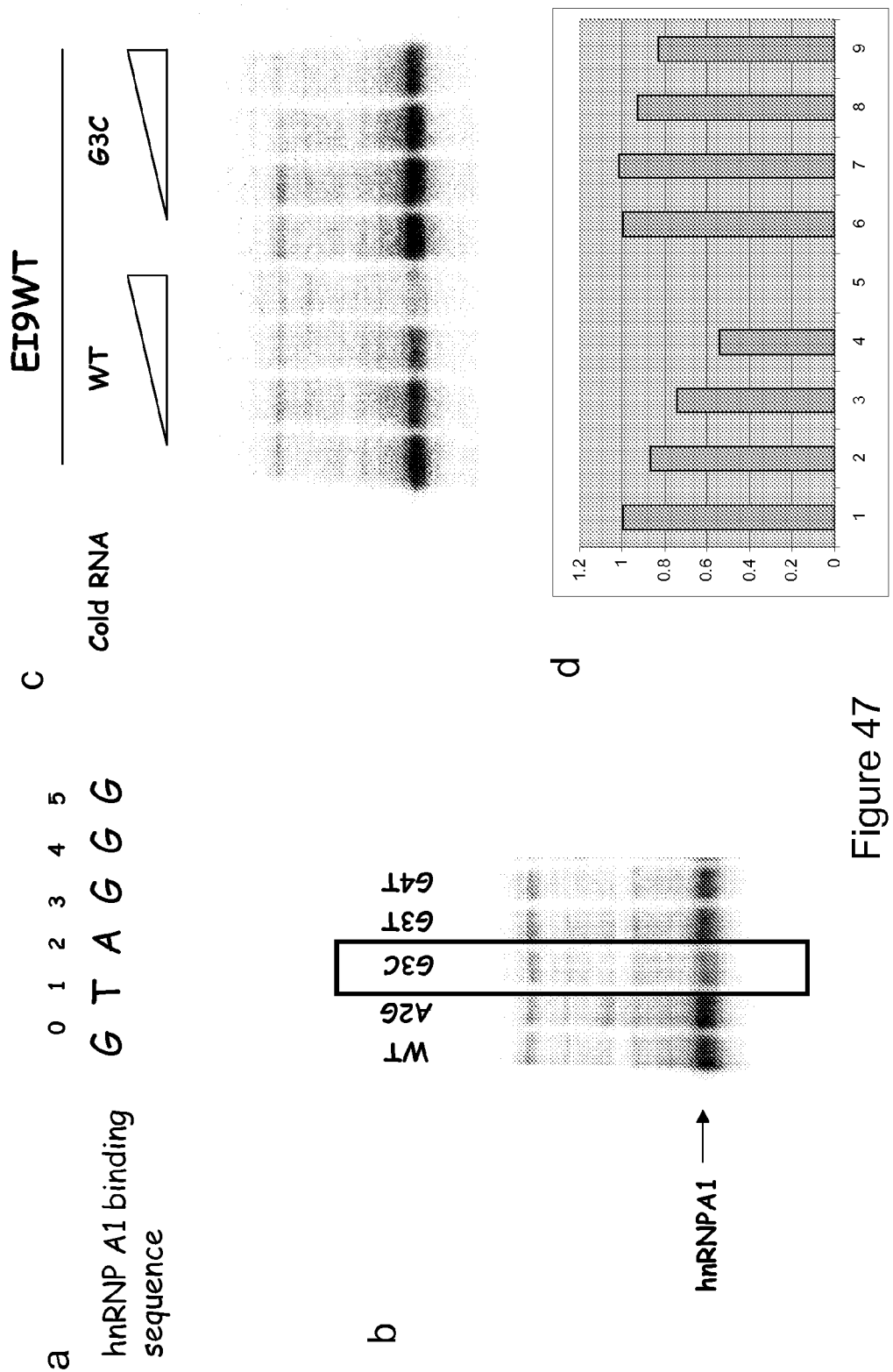
FIGS. 47 *a-d*: Mutagenesis of hnRNP A1 binding site.
Figure 48:
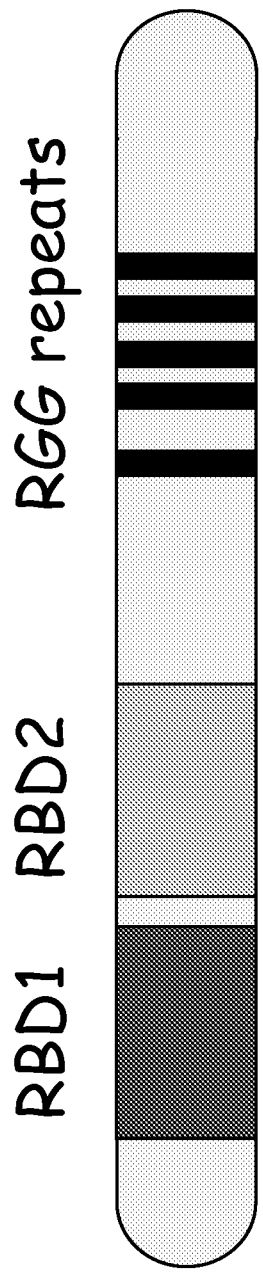
FIG. 48: hRNPA1 and A2: AS regulators associated with cancer.

Mutagenesis of hnRNP A1 binding site (FIGS. 47 a-d).

hRNPA1 and A2: AS regulators associated with cancer (FIG. 48). hnRNP A1 and A2 are closely related abundant nuclear proteins with similar RNA binding preferences; often act as negative regulators of exon inclusion by binding to/near exons and preventing their inclusion; and are overexpressed in many cancers.

Figure 49:
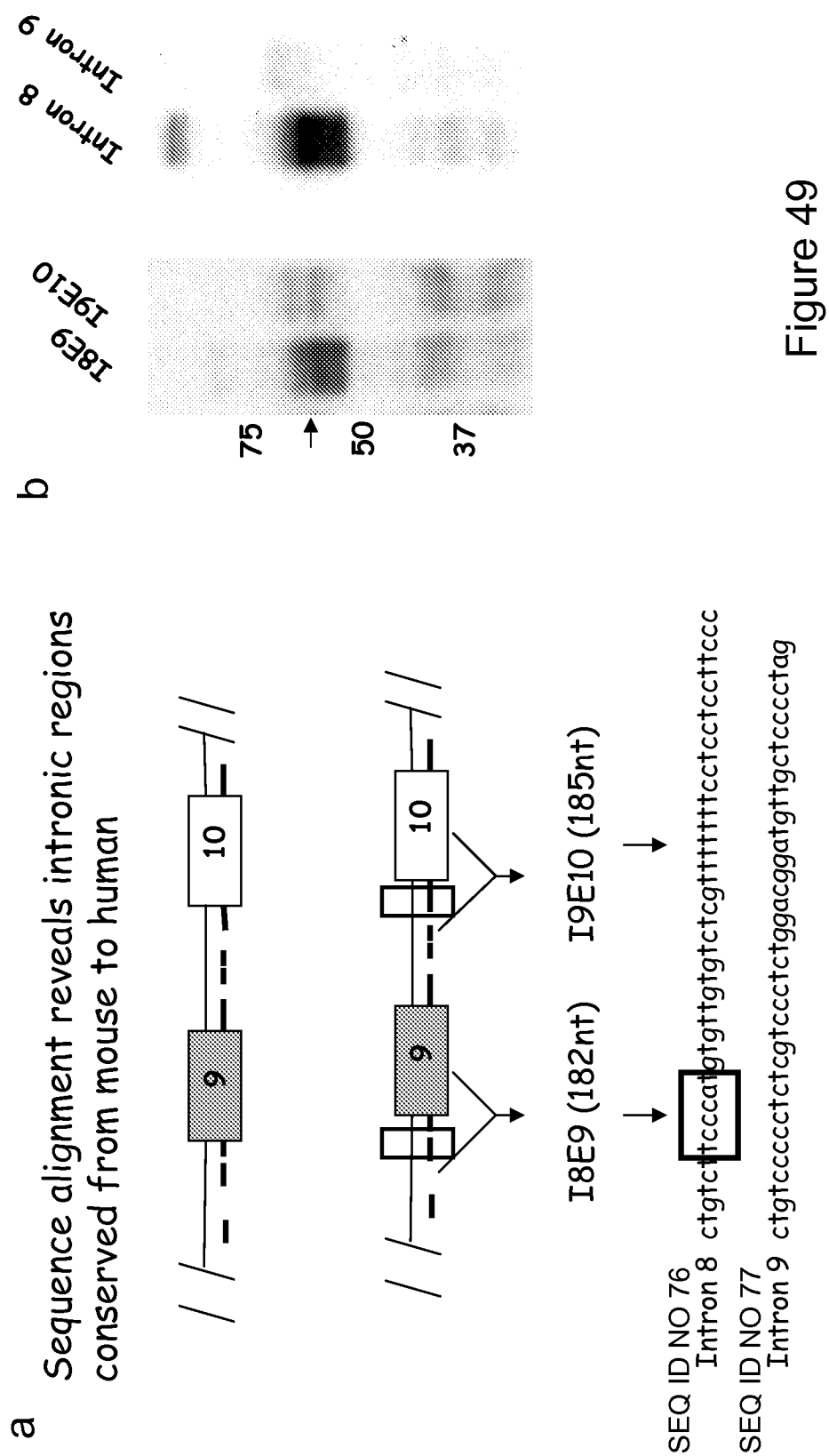
FIGS. 49 *a-b*: UV crosslinking also identifies strong protein binding near the exon 9 3' splice site. Sequence alignment reveals intronic regions conserved from mouse to human.
Figure 50:
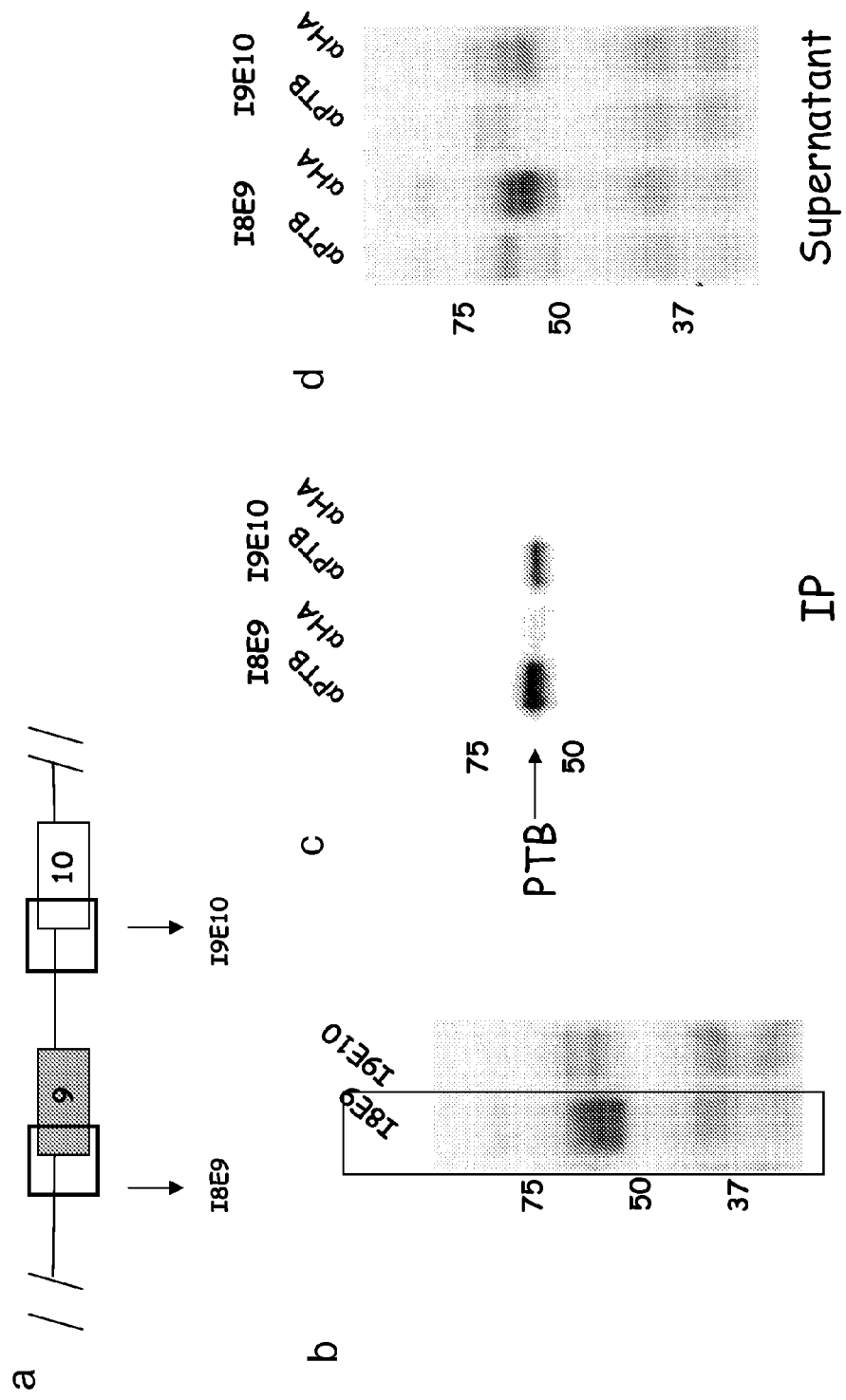
FIGS. 50 *a-d*: UV crosslinking also identifies strong protein binding near the exon 9 3' splice site.

UV crosslinking identifies strong protein binding near the exon 9 3' splice site (FIGS. 49 *a-b* and FIGS. 50 *a-d*).

Figure 51:
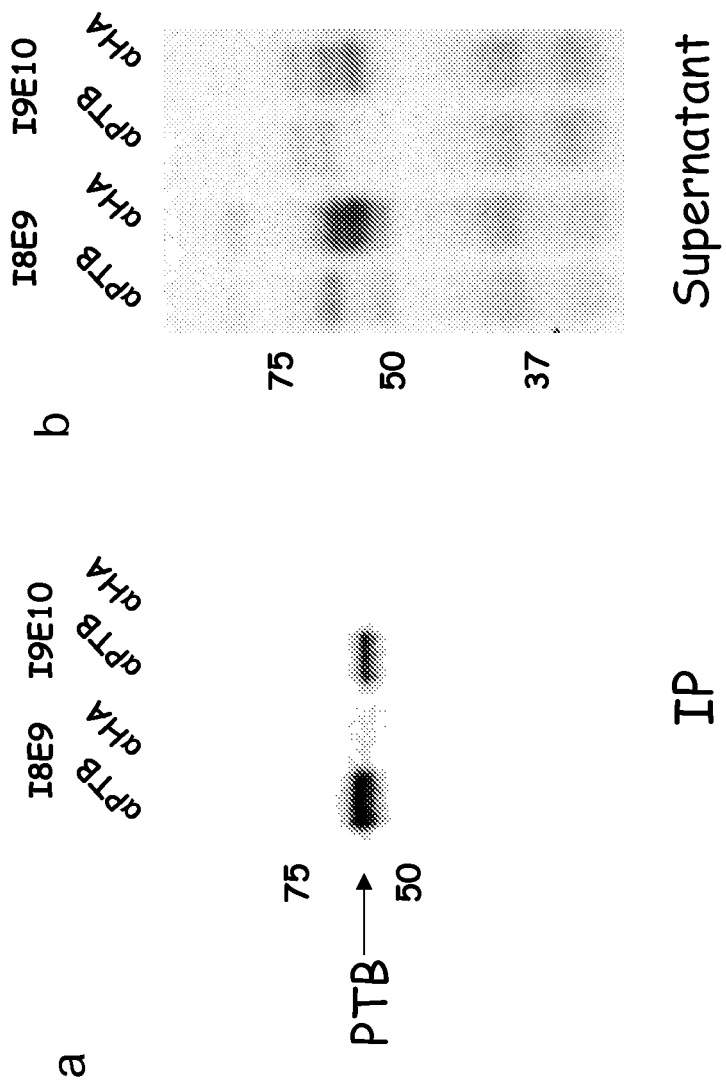
FIGS. 51 *a-b*: Immunoprecipitation identifies PTB as the crosslinking protein.

Immunoprecipitation identifies PTB as the crosslinking protein (FIGS. 51 *a-b*).

Figure 52:
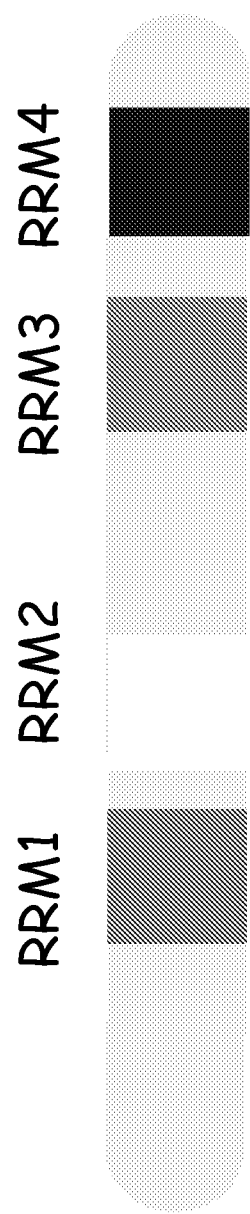
FIG. 52: PTB: an hnRNP protein associated with cancer. Polypyrimidine tract binding protein, aka hnRNP I. Frequently acts as a negative regulator of alternative splicing by binding to CU-rich sequences. Highly expressed in embryonic cells and many cancers, downregulated in differentiated cells.

PTB is an hnRNP protein associated with cancer (FIG. 52). Polypyrimidine tract binding protein, is also known as hnRNP I. PTB frequently acts as a negative regulator of alternative splicing by binding to CU-rich sequences and is highly expressed in embryonic cells and many cancers, and downregulated in differentiated cells.

Figure 53:
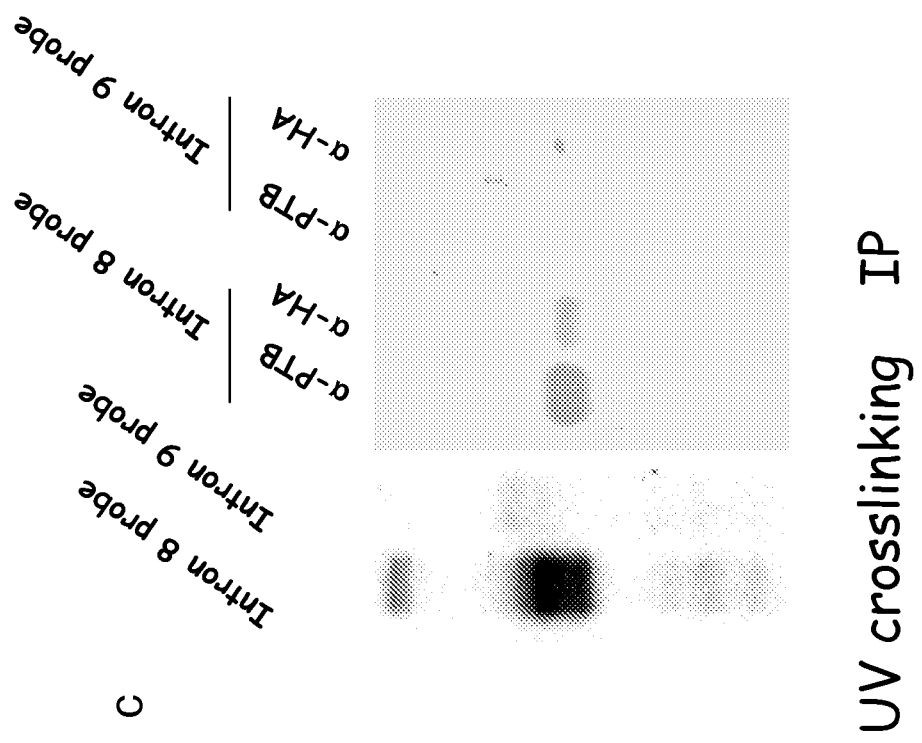
FIGS. 53 *a-c*: PTB binds strongly upstream of exon 9 but not 10.

PTB binds strongly upstream of exon 9 but not 10 (FIGS. 53 *a-c*).

Figure 54:
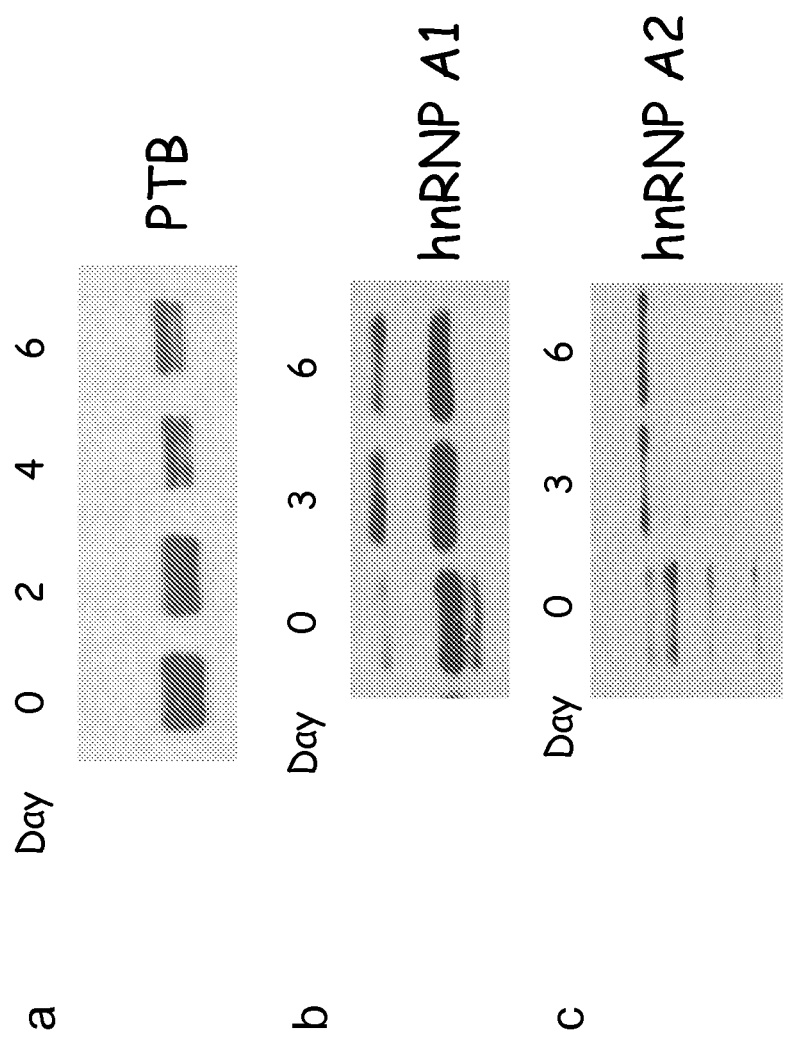
FIGS. 54 *a-c*: PTB abundance declines and hnRNP A1/A2 undergo isoform shifts during C2C12 development.

PTB abundance declines and hnRNP A1/A2 undergo isoform shifts during C2C12 development (FIGS. 54 *a-c*).

Figure 55:
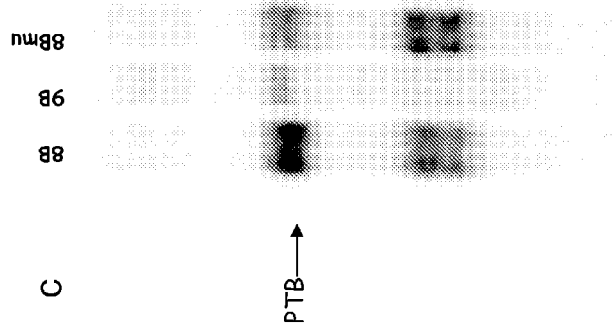
FIGS. 55 *a-c*: Mutation of PTB binding sites.

Mutation of PTB binding sites (FIGS. 55 *a-c*).

Figure 56:
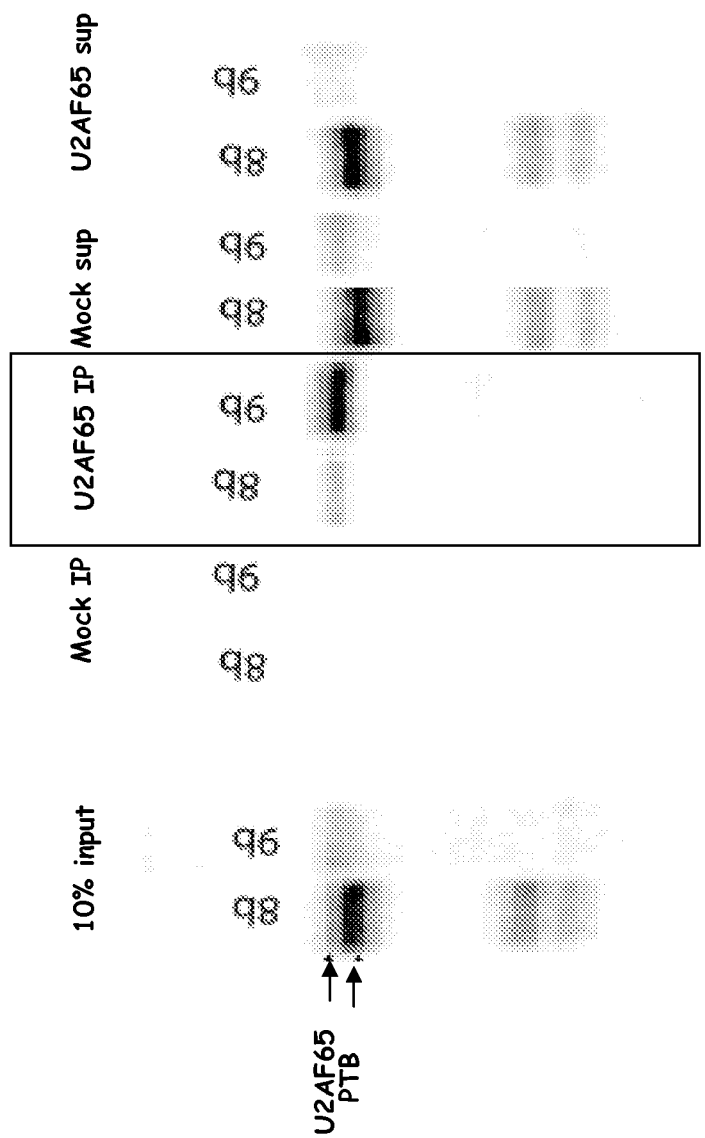
FIG. 56: U2AF65 binds more tightly to the py tract upstream of exon 10.

U2AF65 binds more tightly to the py tract upstream of exon 10 (FIG. 56).

Figure 57:
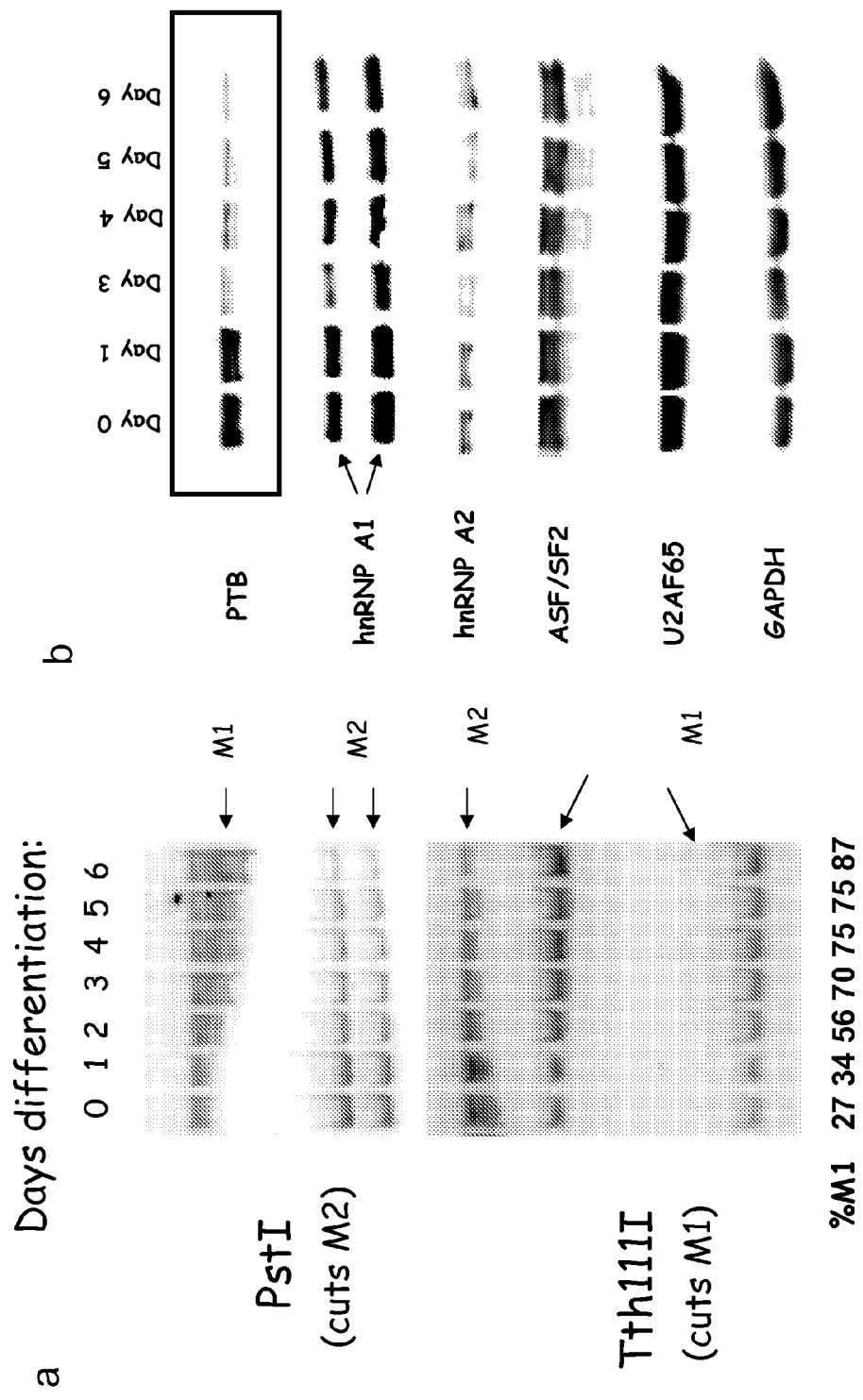
FIGS. 57 *a-b*: Drop in PTB expression coincides with M2 to M1 switch in differentiating C2C12 cells.
Figure 58:
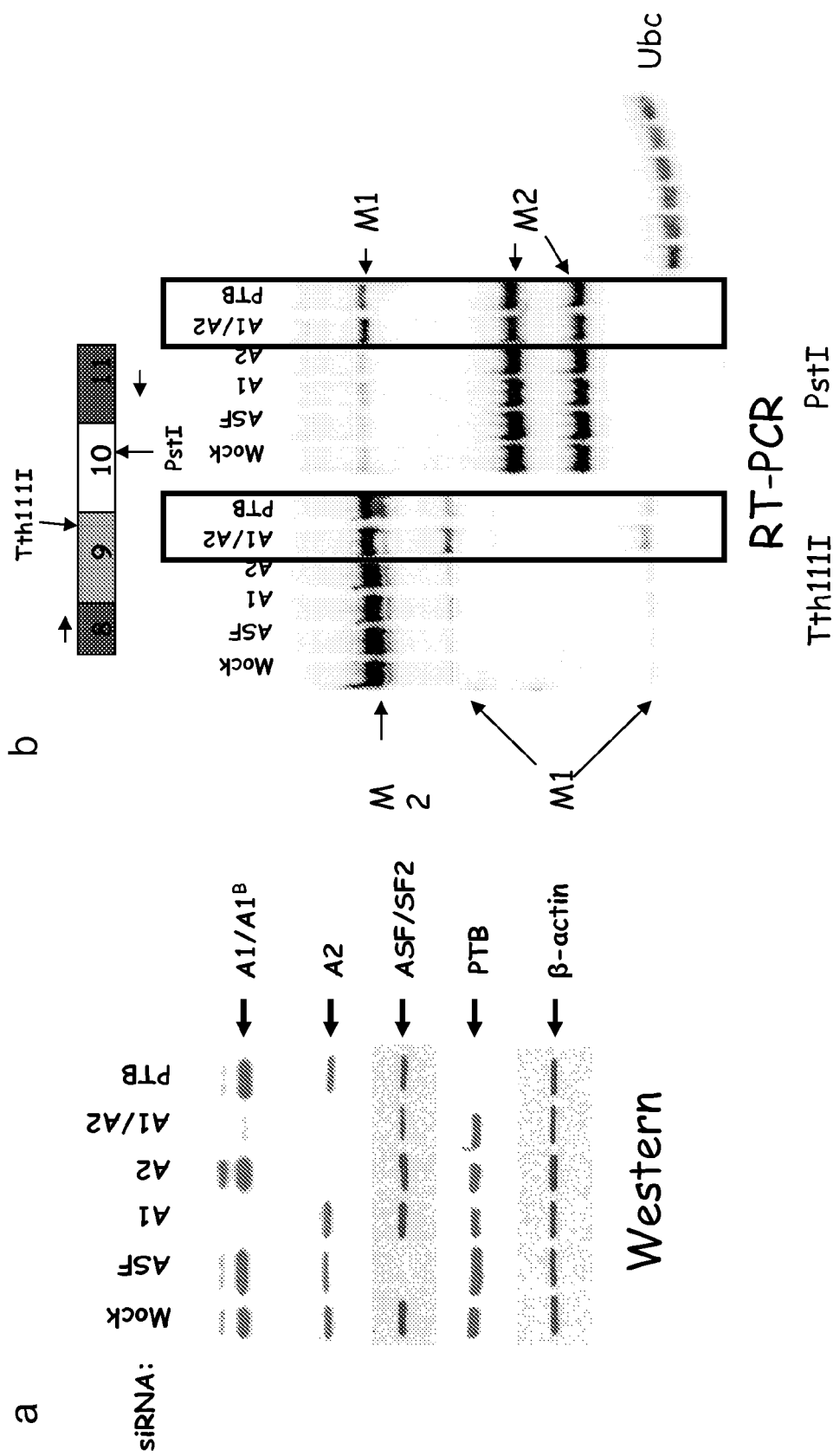
FIGS. 58 *a-b*: siRNA-mediated depletion of hnRNPA1/A2 or PTB increases exon 9 inclusion. Western is shown as FIG. 58 *a*, RT-PCR is shown as FIG. 58 *b*.

Drop in PTB expression coincides with M2 to M1 switch in differentiating C2C12 cells (FIGS. 57 *a-b*).

siRNA-mediated depletion of hnRNPA1/A2 or PTB increases exon 9 inclusion (FIGS. 58 *a-b*).

Figure 59:
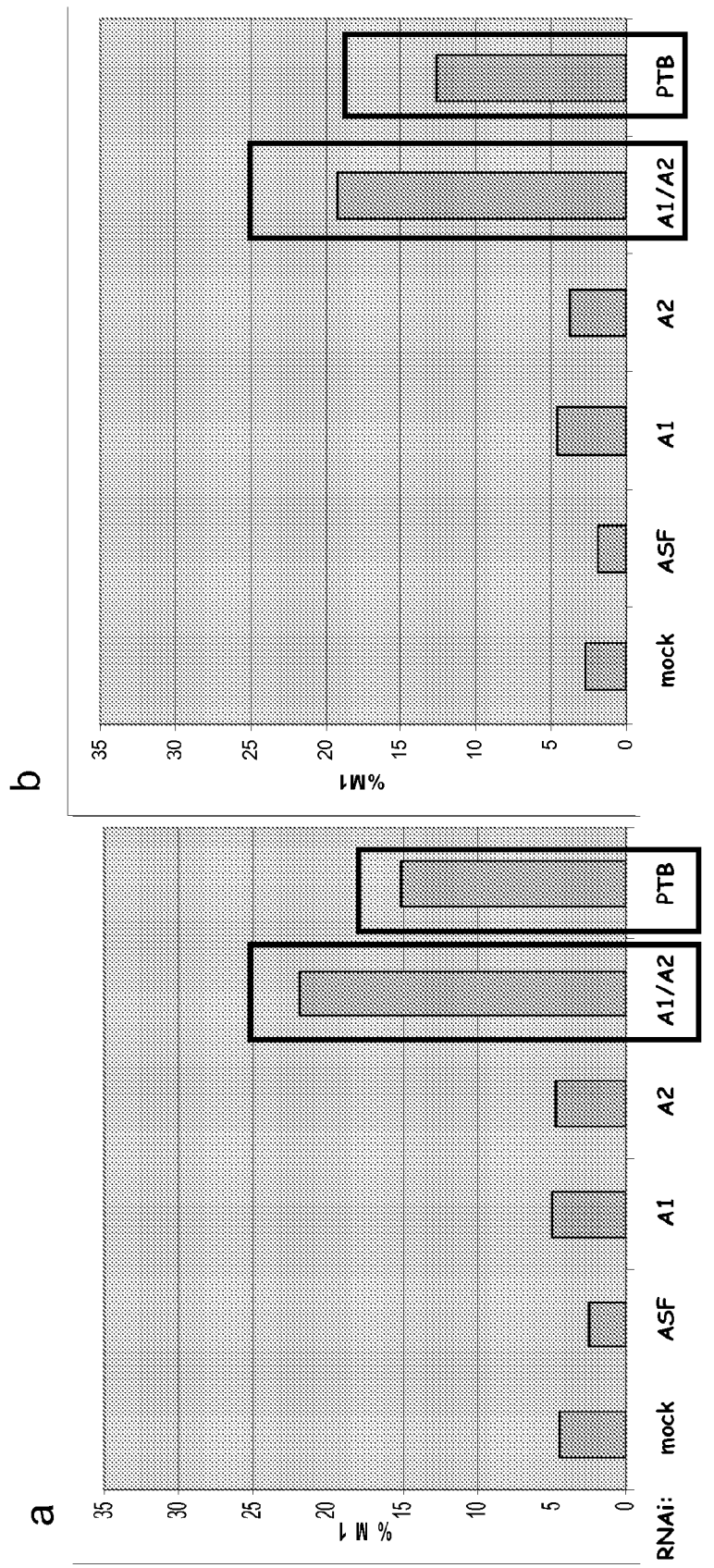
FIGS. 59 *a-b*: Depletion of hnRNPA1/A2 or PTB increases the M1/M2 ratio. Measured with PstI (FIG. 59 *a*) and Tth111I (FIG. 59*b*).
Figure 60:
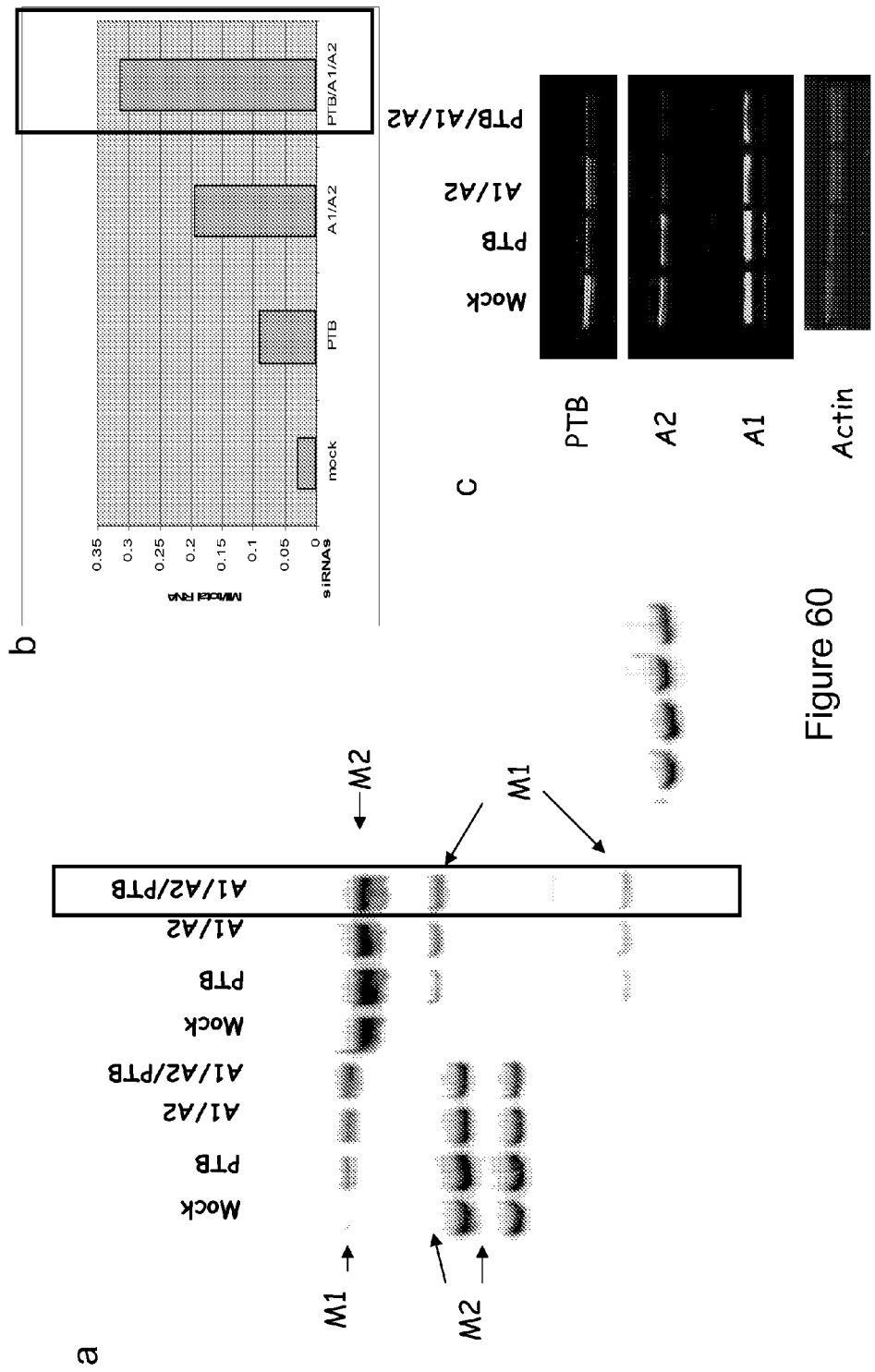
FIGS. 60 *a-c*: hnRNPA1, A2 and PTB knockdown switches PKM2 to PKM1 in HeLa cells.

Depletion of hnRNPA1/A2 or PTB increases the M1/M2 ratio (FIGS. 59 *a-b*).

hnRNPA1, A2 and PTB knockdown switches PKM2 to PKM1 in HeLa cells (FIGS. 60 *a-c*).

Figure 61:
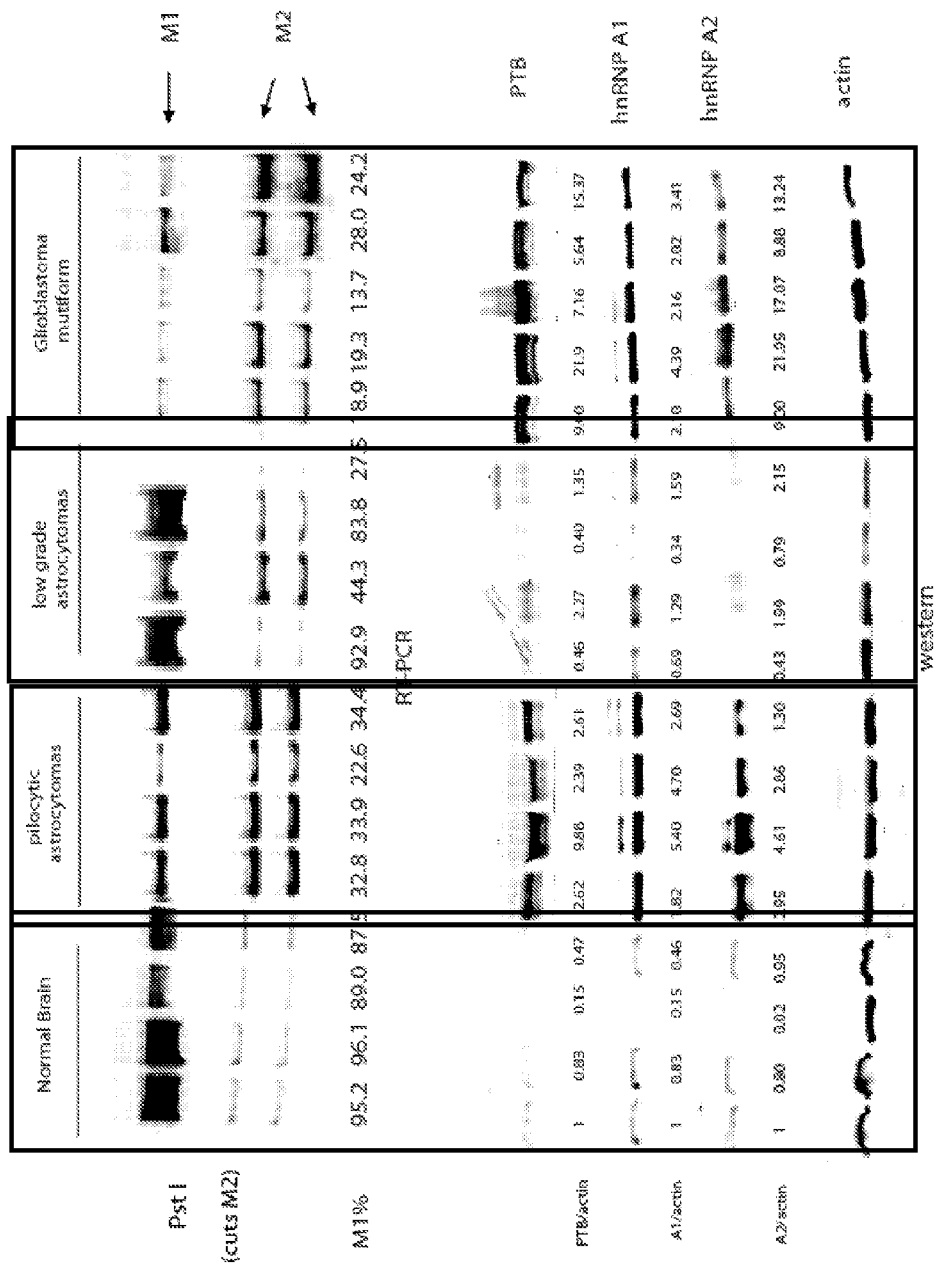
FIG. 61: Upregulation of PTB and hnRTP A1/A2 correlates with PKM2 expression in gliomas.

Upregulation of PTB and hnRTP A1/A2 correlates with PKM2 expression in gliomas (FIG. 61).

Figure 62:
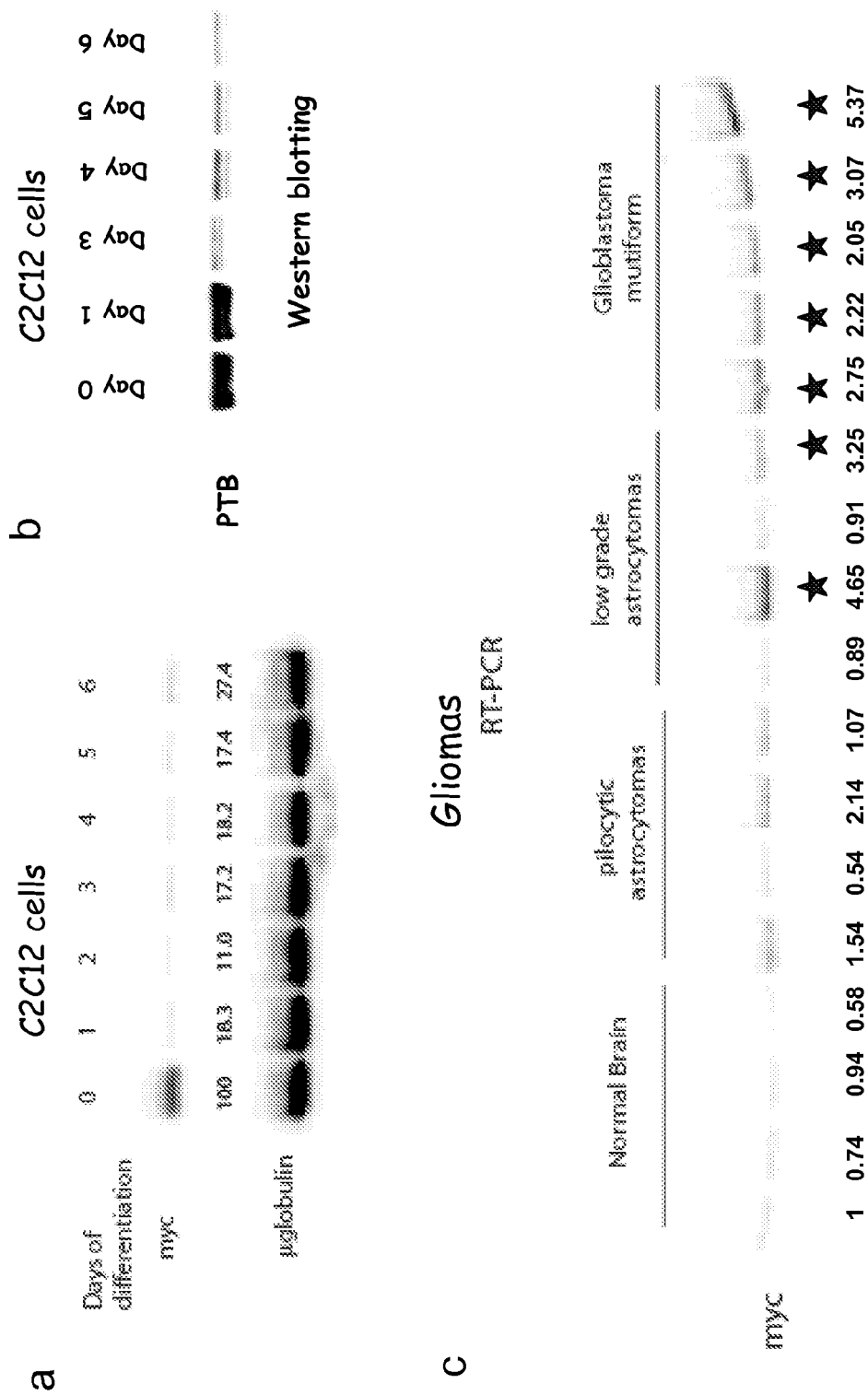
FIGS. 62 *a-c*: Myc expression correlates with PKM2 and hnRNP protein expression in C2C12 cells and gliomas.

Myc expression correlates with PKM2 and hnRNP protein expression in C2C12 cells and gliomas (FIGS. 62 *a-c*).

Figure 63:
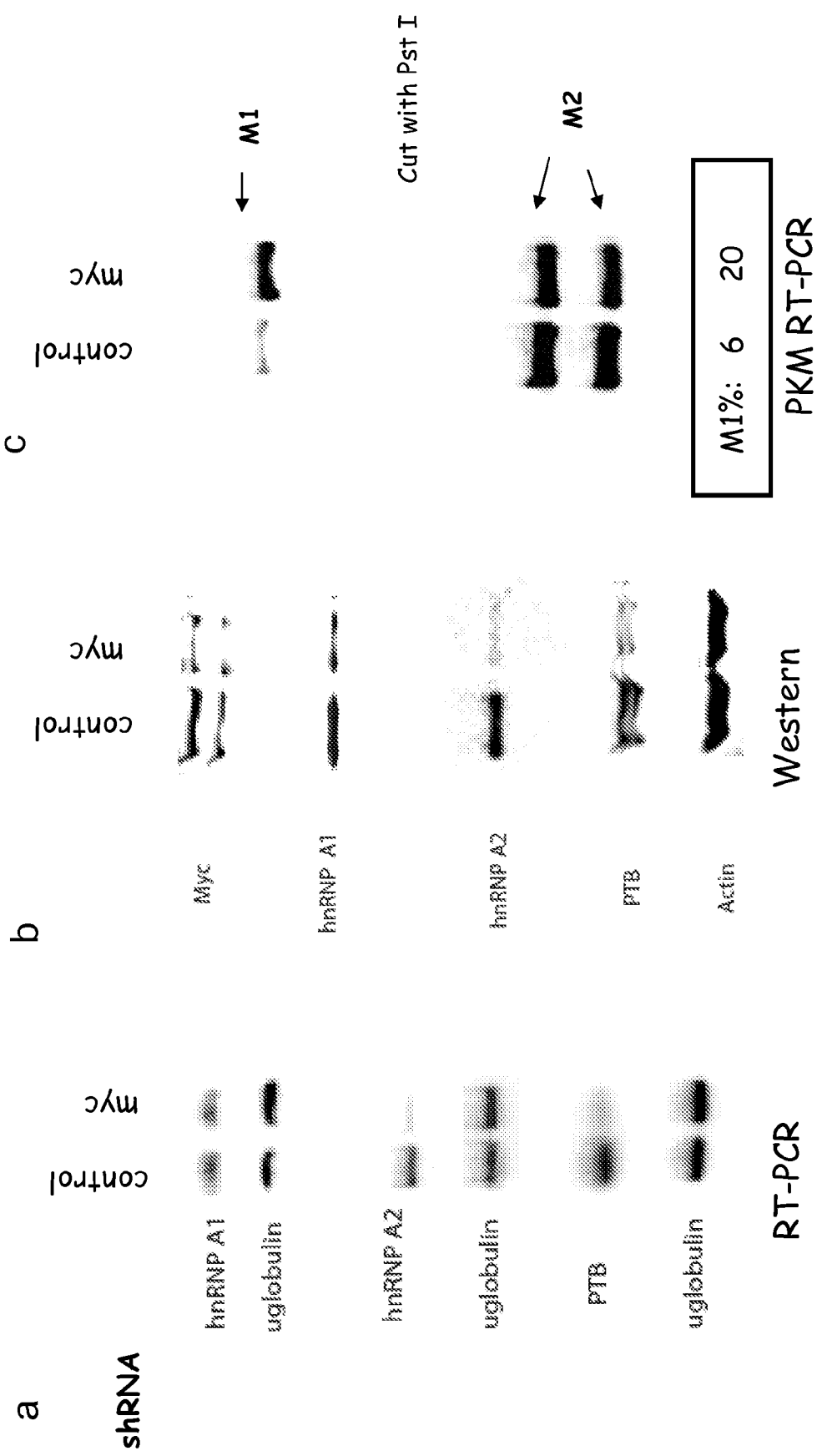
FIGS. 63 *a-c*: Myc shRNA reduces PTB/A1/A2 levels in 3T3 cells and increases PKM1 level. RT-PCR (FIG. 63 *a*), Western (FIG. 63 *b*), PKM RT-PCR (FIG. 63 *c*).

Myc shRNA reduces PTB/A1/A2 levels in 3T3 cells and increases PKM1 level (FIG. 63 *a-c*).

Figure 64:
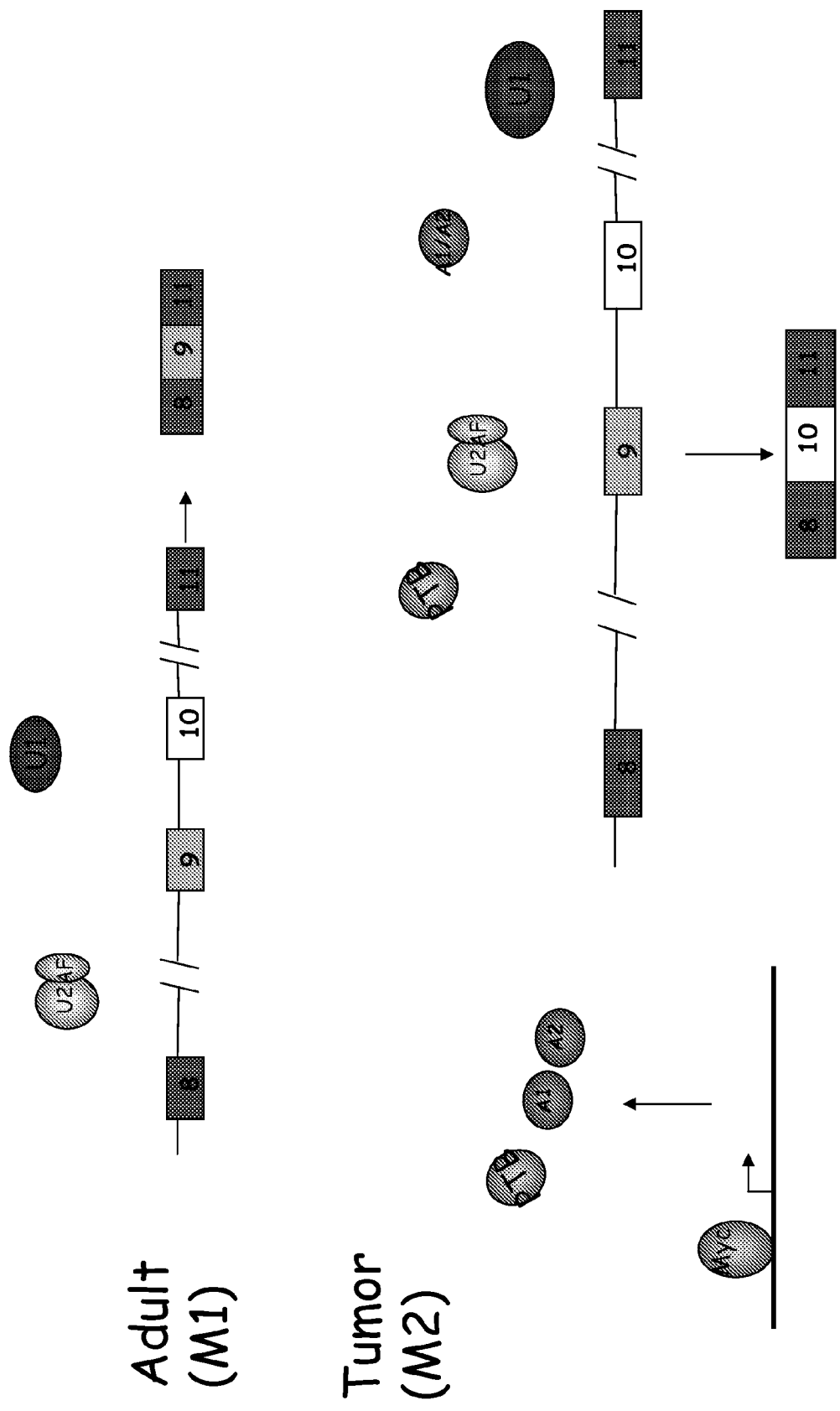
FIG. 64: A model for PTB and hnRNP A1/A2 repression of PKM exon 9 in cancer cells. Top: adult (M1), bottom: tumor (M2).

A model for PTB and hnRNP A1/A2 repression of PKM exon 9 in cancer cells (FIG. 64).

What is claimed is:

1. A method to reduce cell growth of a cancer cell comprising contacting a cancer cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

2. A method to treat cancer comprising administering to a subject in need thereof an effective amount of a combination of inhibitory RNA molecules targeting hnRNPA1, hnRNPA2 and PTB mRNAs, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

3. A method to treat cancer comprising contacting a cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

4. A method to reduce the levels of RNA binding proteins hnRNPA1, hnRNPA2 and PTB in a cell comprising contacting a cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

5. A method to reduce the amount of hnRNPA1, hnRNPA2 and PTB protein bound to pyruvate kinase pre-mRNA in a cell, comprising contacting a cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

6. A method to reduce levels of PKM2 RNA or protein in a cell, comprising contacting a cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

7. A method to increase levels of PKM1 RNA or protein in a cell, comprising contacting a cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

8. A method to reduce the ratio of PKM2/PKM1 RNA or protein in a cell, comprising contacting a cell with an effective amount of a combination of inhibitory RNA molecules targeting hnRNPA1, hnRNPA2 and PTB, wherein the inhibitory RNA molecule targeting hnRNPA1 comprises SEQ ID NO: 9 or is encoded by SEQ ID NO: 64, the inhibitory RNA molecule targeting hnRNPA2 comprises SEQ ID NO: 10 or is encoded by SEQ ID NO: 65, and the inhibitory RNA molecule targeting PTB comprises SEQ ID NO: 11 or is encoded by SEQ ID NO: 63.

9. The method of any of claims 1-8, wherein the inhibitory RNA molecule, which targets hnRNPA1, hnRNPA2 or PTB mRNAs is a siRNA.

10. The method of any of claims 1-8, wherein the inhibitory RNA molecule, which targets hnRNPA1, hnRNPA2 or PTB mRNAs is a shRNA.

11. The method of claim 10, wherein the shRNA is comprised in an RNAi expression vector.

12. The method of any of claims 4-8, wherein the cell is a cancer cell.

13. The method of claim 12, wherein the cancer cell is brain tumor cell, a glioma tumor cell, or a breast cancer cell.

14. The method of any of claims 4-8 wherein the cell expresses PKM2.

15. The method of any of claims 1-8, wherein SEQ ID NOs: 9, 10 and 11 are the sense strand sequence of the inhibitory RNA molecule.

\* \* \* \* \*